(12) United States Patent
Gitler

(10) Patent No.: US 8,969,005 B2
(45) Date of Patent: Mar. 3, 2015

(54) GENE TARGETS ASSOCIATED WITH AMYOTROPHIC LATERAL SCLEROSIS AND METHODS OF USE THEREOF

(75) Inventor: Aaron D. Gitler, Foster City, CA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 13/638,237

(22) PCT Filed: Mar. 28, 2011

(86) PCT No.: PCT/US2011/030178
§ 371 (c)(1),
(2), (4) Date: Nov. 7, 2012

(87) PCT Pub. No.: WO2011/123388
PCT Pub. Date: Oct. 6, 2011

(65) Prior Publication Data
US 2013/0059757 A1 Mar. 7, 2013

Related U.S. Application Data

(60) Provisional application No. 61/318,328, filed on Mar. 28, 2010.

(51) Int. Cl.
*C12Q 1/68* (2006.01)
*C07H 21/04* (2006.01)
*C12N 1/19* (2006.01)
*C12N 5/10* (2006.01)
*C12N 15/79* (2006.01)

(52) U.S. Cl.
CPC ........ *C12Q 1/6883* (2013.01); *C12Q 2600/156* (2013.01); *G01N 2500/02* (2013.01); *G01N 2800/2835* (2013.01); *G01N 2800/50* (2013.01)
USPC ........ 435/6.11; 435/6.1; 435/254.2; 435/348; 536/23.1; 536/24.3

(58) Field of Classification Search
None
See application file for complete search history.

(56) References Cited

FOREIGN PATENT DOCUMENTS

WO 2009/102995 8/2009

OTHER PUBLICATIONS

Panagopoulos et al., "Fusion of the RBP56 and CHN genes in extraskeletal myxoid chondrosarcomas with translocation t(9;17)(q22;q11)," Oncogene 1999, 18:7594-7598.*
Stratagene 1988 catalog (cover and p. 39).*
TRIzol Reagent Package Insert; Rev. Date Dec. 13, 2012 (4 pages).*
Doi, H., et al. "RNA-binding protein TLS is a major nuclear aggregate-interacting protein in huntingtin exon 1 with expanded polyglutamine-expressing cells." J Biol Chem. Mar. 7, 2008;283(10):6489-500. Epub Dec. 31, 2007.
Kwiatkowski, T.J., et al. "Mutations in the FUS/TLS gene on chromosome 16 cause familial amyotrophic lateral sclerosis." Science. Feb. 27, 2009;323(5918)1205-8.
Blair, I.P., et al. "FUS mutations in amyotrophic lateral sclerosis: clinical, pathological, neurophysiological and genetic analysis." J Neurol Neurosurg Psychiatry. Jun. 2010;81(6):639-45. Epub Dec. 3, 2009.
Ticozzi, N., et al. "Mutational analysis reveals the FUS homolog TAF15 as a candidate gene for familial amyotrophic lateral sclerosis." Am J Med Genet B Neuropsychiatr Genet. Apr. 2011;156B(3):285-90. Epub Jan. 13, 2011.
Kovar, H. "Dr. Jekyll and Mr. Hyde: The Two Faces of the FUS/EWS/TAF15 Protein Family." Sarcoma. 2011;2011:837474. Epub Dec. 9, 2010.

* cited by examiner

*Primary Examiner* — Samuel Woolwine
*Assistant Examiner* — Kaijiang Zhang
(74) *Attorney, Agent, or Firm* — Kathleen D. Rigaut; Robert C. Netter, Jr.; Dann, Dorfman, Herrell & Skillman

(57) ABSTRACT

Compositions and methods for diagnosis and treatment of ALS are provided.

6 Claims, 19 Drawing Sheets

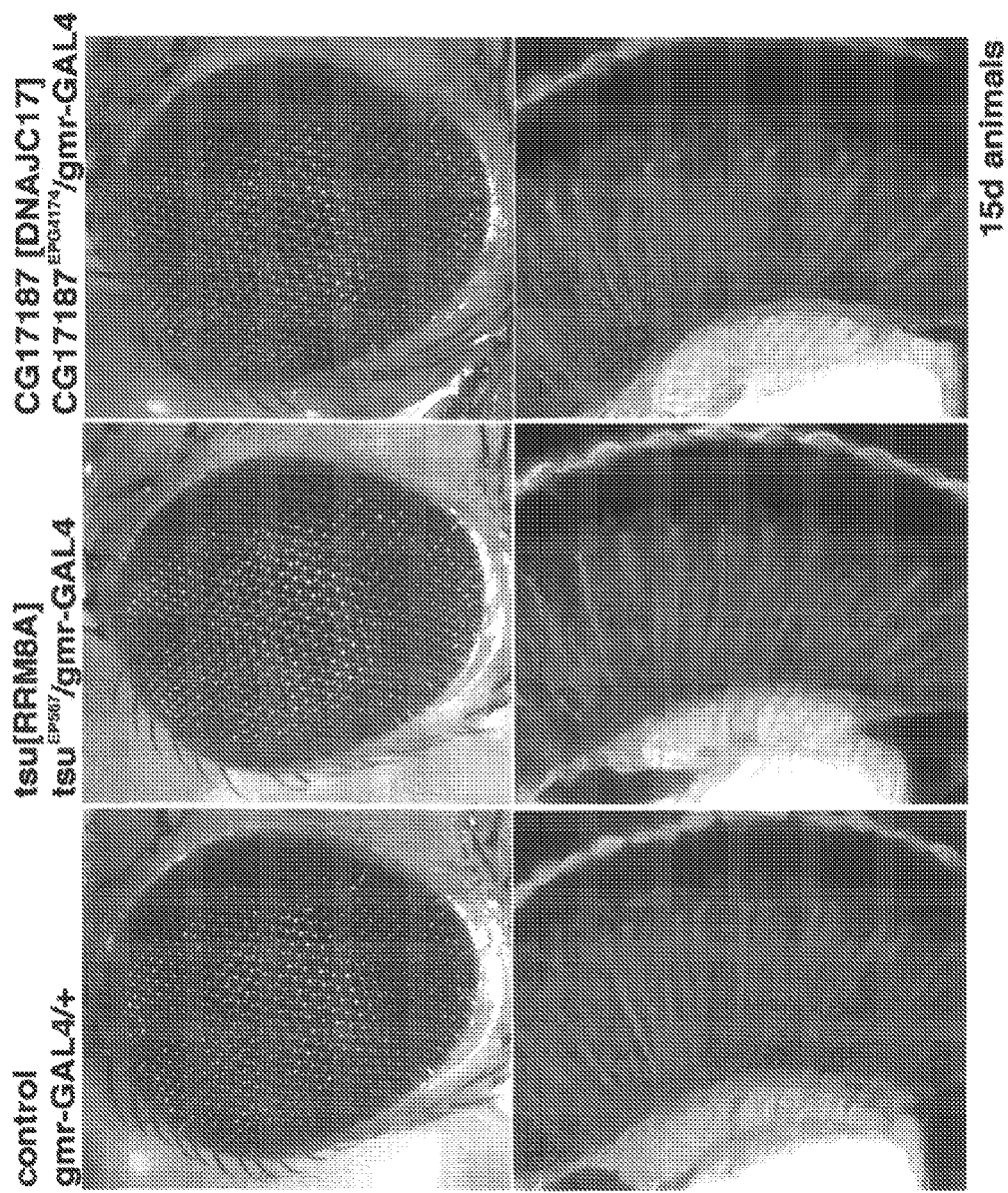

SEQUENCE LISTING

```
<160> NUMBER OF SEQ ID NOS: 15

<210> SEQ ID NO 1
<211> LENGTH: 61
<212> TYPE: DNA
<213> ORGANISM: Artificial Sequence
<220> FEATURE:
<223> OTHER INFORMATION: Primer

<400> SEQUENCE: 1
cccgggacta gtcaccatgg actacaagga cgacgatgac aaaatgtcgg attctggaag      60
t                                                                      61

<210> SEQ ID NO 2
<211> LENGTH: 61
<212> TYPE: DNA
<213> ORGANISM: Artificial Sequence
<220> FEATURE:
<223> OTHER INFORMATION: Primer

<400> SEQUENCE: 2
cacgcggccg cctacagatc ctctttctga gatgagtttt tgttcgtatg gtcggttgcg      60
c                                                                      61

<210> SEQ ID NO 3
<211> LENGTH: 52
<212> TYPE: DNA
<213> ORGANISM: Artificial Sequence
<220> FEATURE:
<223> OTHER INFORMATION: Primer

<400> SEQUENCE: 3
tcaccatgga ctacaaggac gacgatgaca aaatggcgtc cacggattac ag              52

<210> SEQ ID NO 4
```

<211> LENGTH: 60
<212> TYPE: DNA
<213> ORGANISM: Artificial Sequence
<220> FEATURE:
<223> OTHER INFORMATION: Primer

<400> SEQUENCE: 4
cacgcggccg cctacagatc ctcttctgag atgagttttt gttcgtaggg ccgatctctg    60

<210> SEQ ID NO 5
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 6
<223> OTHER INFORMATION: n = g or c

<400> SEQUENCE: 5 tggagnagga    10

<210> SEQ ID NO 6
<211> LENGTH: 11
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 7
<223> OTHER INFORMATION: n = c or t

<400> SEQUENCE: 6
tcctccngcc a    11

<210> SEQ ID NO 7
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 7

Arg Gly Asn Pro Ser Gly Gly Asn Val Gln His Arg Ala Gly Asp
 1               5                  10                  15

Trp Gln Cys Pro Asn Pro Gly Cys Gly Asn Gln Asn Phe Ala Trp Arg
            20                  25                  30

Thr Glu Cys Asn Gln Cys Lys Ala Pro Lys Pro Glu Gly Phe Leu Pro
        35                  40                  45

Pro Pro Phe Pro Pro Pro Gly Gly Asp Arg Gly Arg
    50                  55                  60

<210> SEQ ID NO 8
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 8

Arg Gly Asn Pro Ser Gly Gly Asn Val Gln His Arg Ala Gly Asp
 1               5                  10                  15

Trp Gln Cys Pro Asn Pro Gly Cys Gly Asn Gln Asn Phe Ala Trp Arg
            20                  25                  30

```
Thr Glu Cys Asn Gln Cys Lys Ala Pro Lys Pro Glu Gly Phe Leu Pro
        35                  40                  45

Pro Pro Phe Leu Pro Pro Gly Gly Asp Arg Gly Arg
    50                  55                  60

<210> SEQ ID NO 9
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 9

Arg Gly Ser Pro Val Ser Gly Asn Val Gln His Arg Ala Gly Asp Trp
  1               5                  10                  15

Gln Cys Pro Asn Pro Gly Cys Gly Asn Gln Asn Phe Ala Trp Arg Thr
                20                  25                  30

Glu Cys Asn Gln Cys Lys Ala Pro Lys Pro Asp Gly Pro Phe Pro Pro
        35                  40                  45

Phe Pro Pro Gln Gly Gly Glu Arg Gly Arg
    50                  55

<210> SEQ ID NO 10
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 10

Arg Gly Gly Pro Thr Gly Gly Asn Met Gln Gln Arg Ala Gly Asp Trp
  1               5                  10                  15

Gln Cys Pro Asn Ala Gly Cys Gly Asn Gln Asn Phe Ala Trp Arg Met
                20                  25                  30

Glu Cys Asn Gln Cys Lys Ala Pro Lys Pro Glu Gly Phe Gly Pro Pro
        35                  40                  45

Pro Phe Pro Pro Gly Gly Asp Arg Gly Arg
    50                  55

<210> SEQ ID NO 11
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 5
<223> OTHER INFORMATION: n = g or a

<400> SEQUENCE: 11 tcagnaggag                                                          10

<210> SEQ ID NO 12
<211> LENGTH: 9
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 5
<223> OTHER INFORMATION: n = c or t
```

```
<400> SEQUENCE: 12 aggtngtgg                                                                    9

<210> SEQ ID NO 13
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 13

Trp Val Cys Pro Asn Pro Ser Cys Gly Asn Met Asn Phe Ala Arg Arg
 1               5                  10                  15

Asn Ser Cys Asn Gln Cys Asn Glu Pro Arg Pro Glu Asp Ser Arg Pro
             20                  25                  30

Ser Gly Gly Asp Phe Arg Gly Arg Gly Tyr Gly Gly Glu Arg Gly Tyr
         35                  40                  45

Arg Gly Arg Gly Gly Arg Gly Gly Asp Arg Gly
     50                  55

<210> SEQ ID NO 14
<211> LENGTH: 60
<212> TYPE: PRT
<213> ORGANISM: Artificial Sequence
<220> FEATURE:
<223> OTHER INFORMATION: Synthetic Sequence

<400> SEQUENCE: 14

Trp Val Cys Pro Asn Pro Ser Cys Gly Asn Met Asn Phe Ala Arg Arg
 1               5                  10                  15

Asn Ser Cys Asn Gln Cys Gly Glu Pro Arg Pro Glu Asp Ser Arg Pro
             20                  25                  30

Ser Gly Gly Asp Phe Arg Gly Arg Gly Tyr Gly Gly Glu Arg Gly
         35                  40                  45

Tyr Arg Gly Arg Gly Gly Arg Gly Gly Asp Arg Gly
     50                  55                  60

<210> SEQ ID NO 15
<211> LENGTH: 54
<212> TYPE: PRT
<213> ORGANISM: Artificial Sequence
<220> FEATURE:
<223> OTHER INFORMATION: Synthetic Sequence

<400> SEQUENCE: 15

Trp Val Cys Pro Asn Pro Ser Cys Gly Asn Val Asn Phe Ala Arg Arg
 1               5                  10                  15

Asp Ser Cys Asn Gln Cys Ser Glu Pro Arg Pro Glu Asp Ser Arg His
             20                  25                  30

Gly Gly Asp Arg Gly Arg Gly Gly Tyr Gly Gly Phe Arg Gly Arg Gly
         35                  40                  45

Arg Gly Gly Asp Arg Gly
     50
```

GENE TARGETS ASSOCIATED WITH AMYOTROPHIC LATERAL SCLEROSIS AND METHODS OF USE THEREOF

This application is a §371 Application of PCT/US2011/30178 filed Mar. 28, 2011 which in turn claims priority to U.S. Provisional Application No. 61/318,328, filed Mar. 28, 2010, the entire disclosure if each being incorporated herein by reference as though set forth in full.

Pursuant to 35 U.S.C. §202(c) it is acknowledged that the U.S. Government has rights in the invention described, which was made in part with funds from the National Institutes of Health, Grant Numbers 1DP2OD004417-01 and 1RO1NS065317.

FIELD OF THE INVENTION

The present invention relates to the fields of medicine, protein folding and neurobiology. More specifically, the invention provides a series of genes and alterations therein associated with pathogenesis of amyotrophic lateral sclerosis (ALS). These molecules have utility in diagnostic assays and also in screening assays for identifying agents useful for the treatment of disorders associated with aberrant protein aggregation, particularly in (ALS).

BACKGROUND OF THE INVENTION

Several publications and patent documents are cited throughout the specification in order to describe the state of the art to which this invention pertains. Each of these citations is incorporated by reference herein as though set forth in full.

The United States and other countries around the world are experiencing a demographic sea change owing to the rapidly growing elderly and 'Baby Boomer' populations (Trojanowski, (2008) Neurosignals 16: 5-10). Our astonishing biomedical advances in the last half-century have greatly increased our life expectancy. But as a consequence of living longer, our population now faces an increase in the incidence of neurodegenerative diseases. These truly disastrous disorders include Alzheimer's, Huntington's, Parkinson's, amyotrophic lateral sclerosis (ALS) and the frontal temporal dementias (Forman et al. (2004) Nat. Med. 10:1055-1063).

In the future, personalized genome sequencing will become routine, empowering us to define the genetic basis of many human diseases. Currently, however, complete genome sequencing for individuals to discover rare pathogenic mutations is still too costly and time consuming. Thus, more creative approaches are needed for disease gene discovery; moreover, even once genes are revealed, the need for innovative approaches to elucidate causality remains critical.

ALS, also known as Lou Gehrig's disease, is a devastating adult-onset neurodegenerative disease that attacks upper and lower motor neurons (Cleveland and Rothstein, 2001). A progressive and ultimately fatal muscle paralysis ensues, usually causing death within 2 to 5 years of disease onset. ALS is mostly sporadic, but approximately 10% of cases are familial. Pathogenic mutations in several genes have been linked to familial and sporadic ALS, including SOD1, TARDBP, FUS/TLS, VAPB, OPTN and others (Van Damme and Robberecht, 2009). Two of these genes, TARDBP (which encodes TDP-43) and FUS/TLS (FUS) are notable because they encode related RNA-binding proteins (Lagier-Tourenne and Cleveland, 2009). Moreover, both of these proteins have been identified as components of pathological inclusions in neurons of ALS patients (Kwiatkowski et al., 2009; Neumann et al., 2006; Vance et al., 2009). Indeed, an emerging concept suggested by the association of FUS and TDP-43 to ALS is that defects in RNA metabolism might contribute to disease pathogenesis. Accordingly, genes encoding proteins involved in RNA metabolism may provide a new avenue to pursue in the development of efficacious therapeutic targets useful for the treatment of these devastating neurological disorders.

SUMMARY OF THE INVENTION

We have identified several RNA binding proteins in a functional yeast screen which appear to play a role in TDP-43 mediated cellular toxicity and aberrant protein aggregation. These data have resulted in methods for predicting an increased risk of an individual for developing amyotrophic lateral sclerosis (ALS) disease. In one embodiment, the method entails obtaining a nucleic acid sample encoding EWSR1 from said individual and determining whether or not said EWSR1 comprises a mutation selected from the group consisting of a missense mutation in exon 16 (1532 G>C giving rise to a Gly511Ala alteration), and a missense mutation in exon 17 (1655 C>T giving rise to a Pro522Leu alteration) relative to wild-type EWSR1 encoding nucleic acids, wherein the presence of at least one mutation in said EWSR1 encoding nucleic acid when compared to wild type EWSR1 encoding nucleic acids obtained from patients not having ALS is indicative of an increased risk of developing ALS. In another embodiment of the invention, the method entails obtaining a nucleic acid sample encoding TAF15 from said individual and determining whether or not said TAF15 comprises a mutation selected from the group consisting of a missense mutation in exon 14 (1172 G>A giving rise to a Gly391Glu alteration) and in exon 15 (1222C>T giving rise to a Arg408Cys) relative to wild-type TAF15 encoding nucleic acids, wherein the presence of said at least one mutation in said TAF15 encoding nucleic acid when compared to wild type TAF15 encoding nucleic acids obtained from patients not having ALS is indicative of an increased risk of ALS. In preferred embodiments the methods described above are useful for predicting an increased risk for development of early onset ALS.

Diagnostic kits for performing the methods mentioned above comprising reagents suitable for isolation of DNA, and reagents suitable for detection of said mutation containing EWSR1 and TAF15 nucleic acid also form an embodiment of the invention.

In yet another aspect, the invention entails a method identifying agents which inhibit TDP-43 associated complex formation with at least one RNA binding protein listed in Table 1. Particularly preferred targets include EWSR1, TAF15, TIA1, DAZ1, DAZ2, DAZ3, DAZAP1, HNRNPA0, and RBM14. An exemplary method comprises providing a cell which expresses TDP-43 and said RNA binding protein, the expression being associated with increased cellular toxicity and cytoplasmic aggregate formation. Contacting the cell with an effective amount of an agent; and measuring cellular toxicity and/or aggregate formation in the presence of said agent relative to a non-treated control cell, wherein a decrease in cellular toxicity identifies an agent which reduces TDP-43-RNA binding protein mediated cellular toxicity and cytoplasmic aggregate formation. Agents identified using these screening methods are also encompassed within the present invention.

Also provided are isolated nucleic acids encoding the altered EWSR and TAF15 proteins described herein. Such isolated nucleic acids can be affixed to a solid support, or introduced into a host cell for screening agents that may have efficacy for the treatment of ALS.

DETAILED DESCRIPTION OF THE INVENTION

Figure 1:
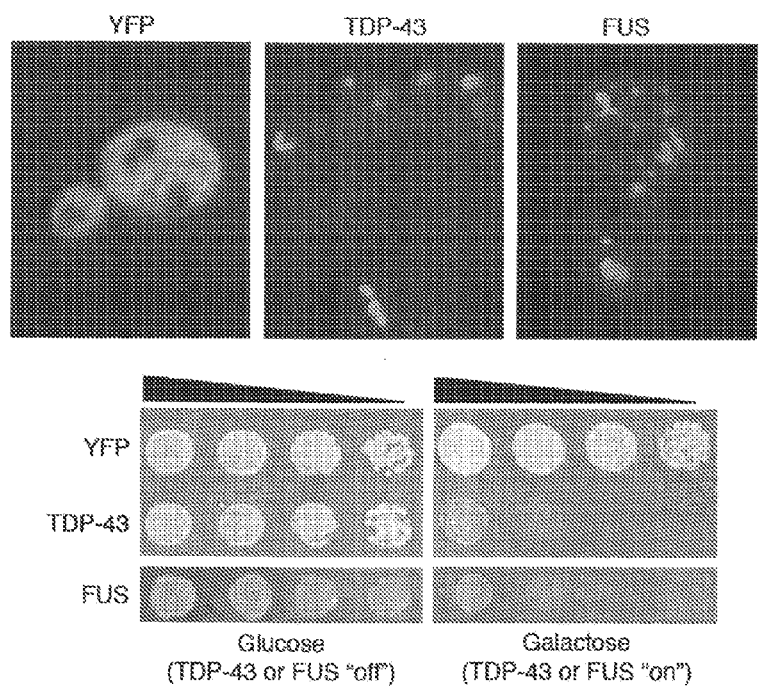
FIG. 1. A yeast functional screen identifies human RRM proteins with properties similar to FUS and TDP-43. (a) When expressed in yeast, TDP-43 and FUS form multiple cytoplasmic aggregates (top) and are toxic (bottom). (b) We designed a yeast functional screen to identify additional human RRM proteins that aggregate and are toxic in yeast. A library of 132 different human ORFs encoding the proteins as YFP fusions was individually transformed into yeast cells. (c) Examples of various localization patterns in yeast cells of human RRM proteins. Some proteins were localized diffusely throughout the cytoplasm (TUT1 and DND1) and others were localized diffusely in the nucleus (PPIE and DNAJC17). Some formed multiple foci in the nucleus (RBM39) and several others resembled FUS and TDP-43, which formed multiple cytoplasmic foci (EWSR1, HNRNPA0, DAZ1). (d) Spotting assays to assess the toxicity of human RRM proteins. Transformants were grown on synthetic media containing either glucose (control, RRM gene "off") or galactose (to induce expression of candidate ORFs, RRM gene "on"). Some proteins were very toxic when overexpressed (DAZ1, ELAV1, FUS, TDP-43) while others were moderately toxic (EWSR1) and others were not toxic (PPIE and DNAJC17). See Table 1 and Table 2 for toxicity and aggregation scores.
Figure 1:
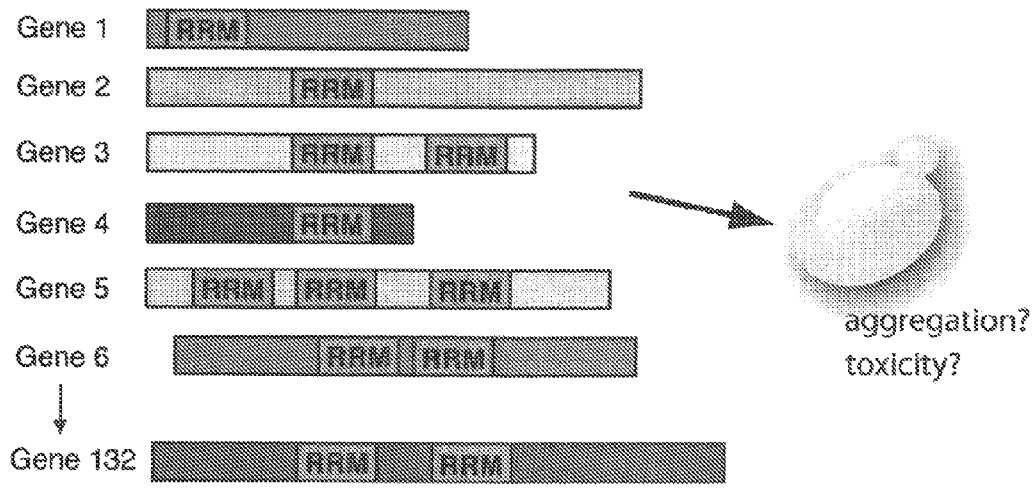
Figure 1:
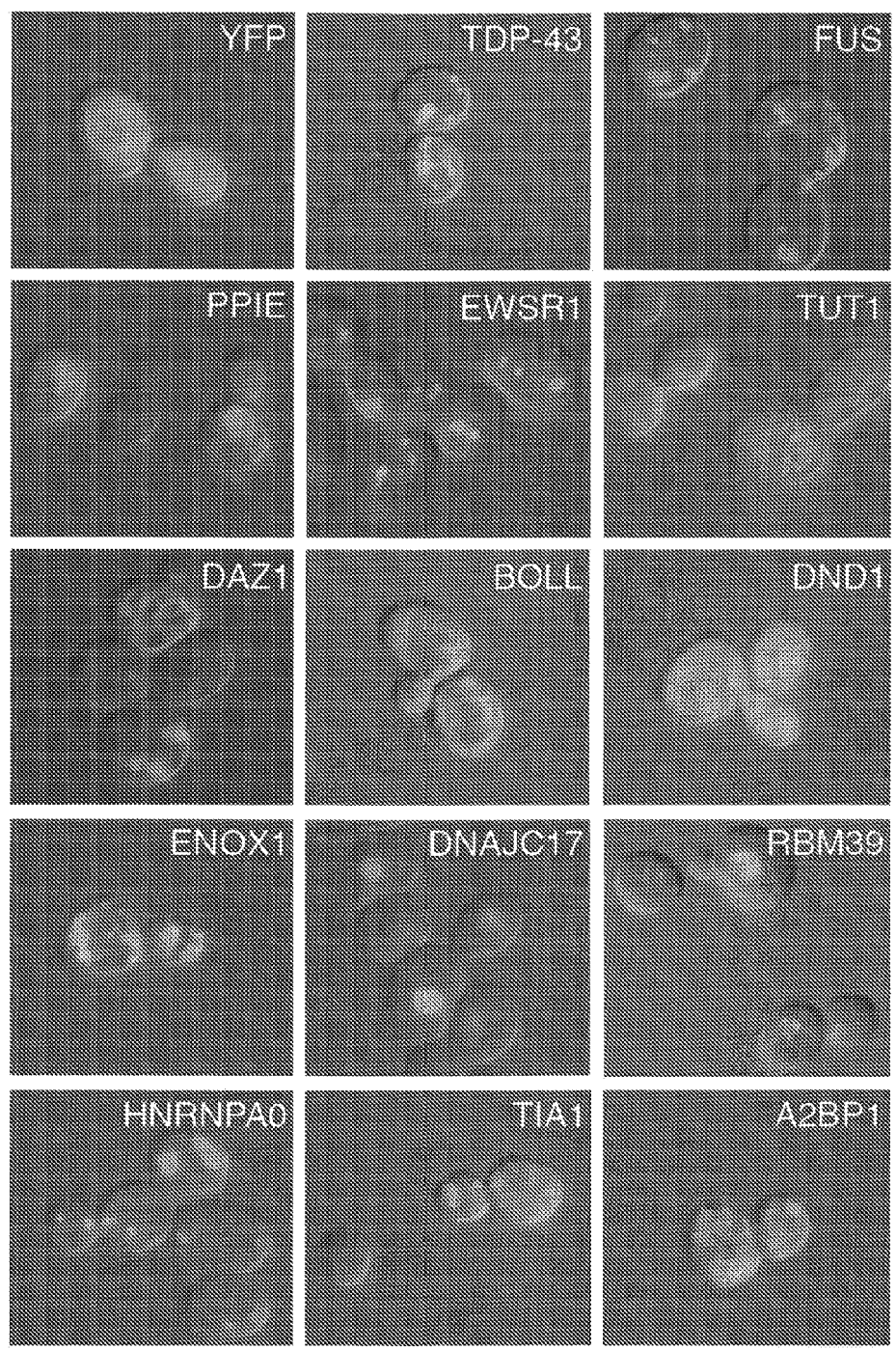
Figure 1:
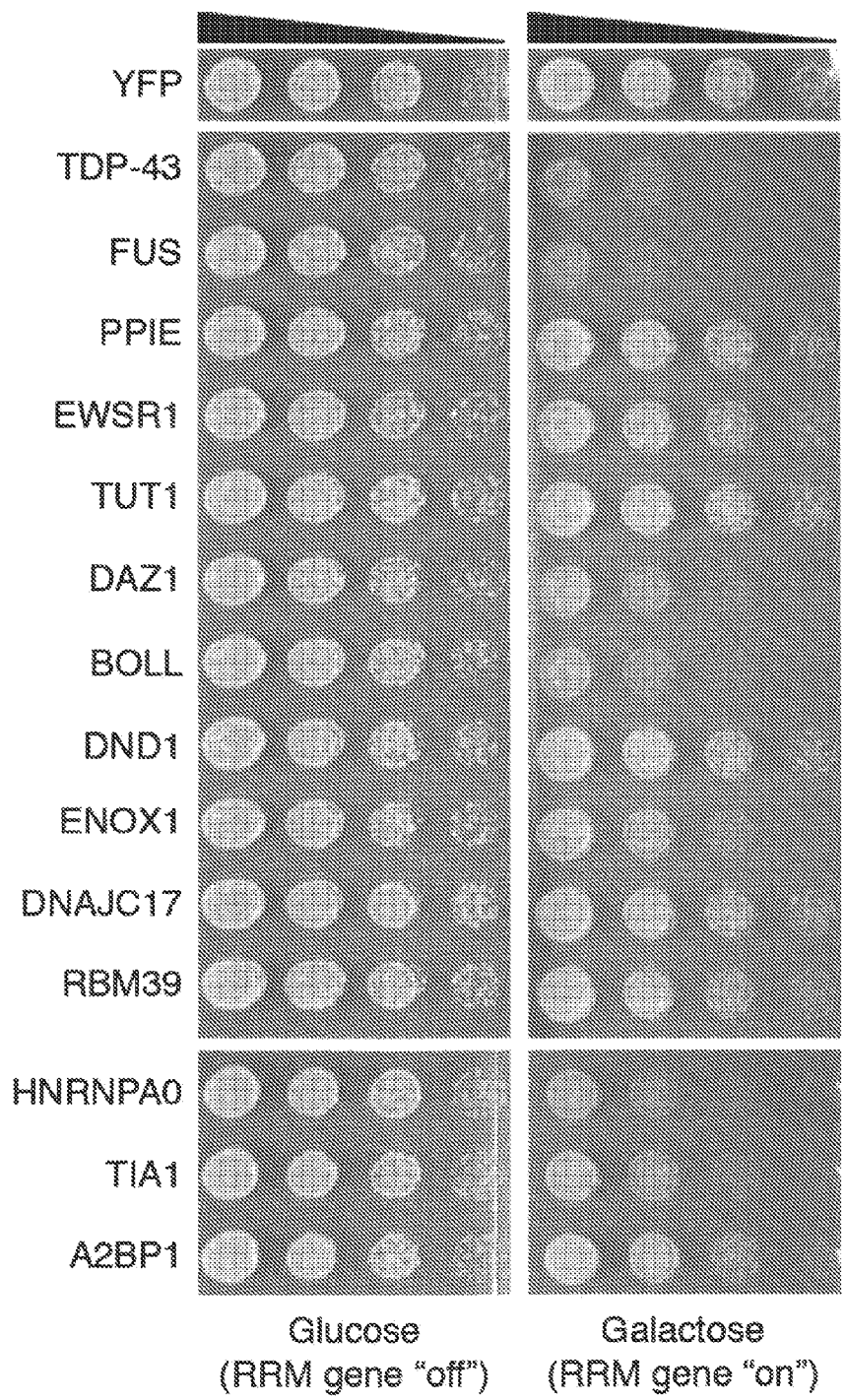

Amyotrophic lateral sclerosis (ALS) is a devastating human neurodegenerative disease. The causes of ALS are poorly understood, although mutations in two related RNA-binding proteins, TDP-43 and FUS/TLS, have been linked to the disease. Both proteins aggregated and caused toxicity in yeast cells. Including FUS/TLS and TDP-43, the human proteome contains at least 226 RNA-binding proteins. In accordance with the present invention, a yeast functional screen was designed to identify new genes associated with the pathogenesis of ALS. To find additional proteins with properties like TDP-43 and FUS/TLS we expressed 133 RNA-binding proteins in yeast and identified 35 that formed aggregates and were toxic. Further computational analysis revealed the presence of a prion-like domain in FUS, TDP-43 and 8 others. We sequenced two of these genes, EWSR1 (Ewing sarcoma breakpoint region 1) and TAF15 (RNA polymerase II, TATA box binding protein (TBP)-associated factor, 68 kDa), in 600 ALS patients and identified three mutations (G511A, P552L, G584S) in EWSR1 and two mutations in TAF15 (R388H and G391E). None of these variants were found in over 800 control individuals.

Functional evidence reveals that EWSR1 and TAF15 have similar in vitro and in vivo properties as TDP-43 and FUS, can confer neurodegeneration in *Drosophila*, and we show that disease-associated variants affect localization of the respective proteins in motor neurons, a disease relevant cell type. The additional genes identified in the yeast functional screen, coupled with prion domain prediction analysis, now provide a powerful resource to facilitate ALS disease gene discovery which in turn can lead to the development of therapeutics that have efficacy for the treatment of this deadly disease.

Definitions

"Amyotrophic lateral sclerosis (ALS)" is a progressive neurodegenerative disease that affects nerve cells in the brain and the spinal cord. Motor neurons reach from the brain to the spinal cord and from the spinal cord to the muscles throughout the body. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

A "proteinopathy" is a disease which is characterized by accumulation of toxic insoluble protein aggregates in cells. Exemplary disorders, include, without limitation, ALS, FTD, FTLD-U, Alzheimer's disease, Huntington's disease, Parkinson's disease, and other motor neuron diseases.

Ewing sarcoma breakpoint region 1 (EWSR1) encodes a multifunctional protein that is involved in various cellular processes, including gene expression, cell signaling, and RNA processing and transport. The protein includes an N-terminal transcriptional activation domain and a C-terminal RNA-binding domain. Chromosomal translocations between this gene and various genes encoding transcription factors result in the production of chimeric proteins that are involved in tumorigenesis. Mutations in this gene, specifically a t(11;22)(q24;q12) translocation, are known to cause Ewing sarcoma as well as neuroectodermal and various other tumors. Alternative splicing of this gene results in multiple transcript variants.

TAF15 (RNA polymerase II, TATA box binding protein (TBP)-associated factor) is a 68 kDa single strand DNA/RNA binding protein and forms part of theTFIID and RNA polymerase II complex of proteins which assemble on the promoter to form a pre-initiation complex (PIC); TFIID is composed of a TATA-box-binding protein (TBP) and a number of TBP-associated factors (TAFIIS). TAF15 shows homology with EWSR1 and FUS.

When the terms "prevent," "preventing," or "prevention" are used herein in connection with a given treatment for ALS, they mean that the treated subject either does not develop a clinically observable level ALS at all, or the condition develops more slowly and/or to a lesser degree in the subject than it would have absent the treatment. These terms are not limited solely to a situation in which the subject experiences no aspect ALS whatsoever. For example, a treatment will be said to have "prevented" ALS if it is given to a subject at risk of developing a ALS and results in the subject's experiencing fewer and/or milder symptoms of the proteinopathy than otherwise expected. A treatment can "prevent" ALS when the subject displays only mild overt symptoms of ALS. "Prevention" does not imply that there must have been no symptoms of ALS in any cell of a subject.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the TDP-43 or genetic modifier encoding nucleic acid molecule such that the latter is transcribed into mRNA. Host cell machinery then translates mRNA into a polypeptide. As mentioned hereinbelow, a variety of transgenic organisms are contemplated for use in the screening assays of the invention.

Those skilled in the art will recognize that a nucleic acid vector can contain nucleic acid elements other than the promoter element and the genetic modulator encoding nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, zebrafish, worm, insect and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism" or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

Methods of Using Nucleic Acids Encoding Mutated RNA Binding Proteins in Assays for Diagnosing an Increased Risk of ALS The identification of mutations in EWSR1 and TAF15 encoding nucleic acids and their association with ALS facilitates the development of a diagnostic assay for identifying patients having an increased risk of developing ALS. Mutation containing EWSR1 and TAF15 nucleic acids, including those described in Example I may be used for a variety of purposes in accordance with the present invention. DNA, RNA, or fragments of these nucleic acids may be used as probes to detect the presence of and/or expression of the same in patient samples. Such assays include but are not limited to: (1) in situ hybridization; (2) Southern hybridization (3) northern hybridization; and (4) assorted amplification reactions such as polymerase chain reactions (PCR).

Assays for detecting mutation containing EWSR1 and TAF15 nucleic acids may be conducted on any type of biological sample, including but not limited to body fluids (including blood, urine, serum, gastric lavage), any type of cell (such as brain cells, white blood cells, mononuclear cells) or body tissue.

In most embodiments for screening for the presence of nucleic acids encoding mutated EWSR1 and TAF15, nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art. Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Reagents for performing both techniques are commercially available from Qiagen Inc. (USA). Also encompassed by the present invention are methods for high throughput sequencing DNA isolated from patients. Such methods are well known to those of skill in the art.

Kits and Articles of Manufacture

Any of the aforementioned products can be incorporated into a kit which can contain nucleic acids encoding mutation containing EWSR1 and TAF15 molecules or other such markers immobilized on a Gene Chip. PCR primers and other suitable reagents can be designed using the following GenBank Accession Nos. EWSR1 mRNA: NM_013986.3 EWSR1 protein: NP_053733.2; TAF15 mRNA: NM_139215.1 and TAF15 protein NP_631961.1—for sequence information. One embodiment of the kit comprises primers and reagents suitable for performance of PCR. Other reagents can include oligonucleotides, polypeptides with and without the mutations described above for use as controls, an antibody, a label, marker, or reporter, a pharmaceutically acceptable carrier, instructions for use, a container, a vessel for administration, an assay substrate, or any combination thereof.

Screening Assays for Identifying Agents which Modulate Cellular Toxicity and Aberrant Protein Aggregation Having Efficacy for the Treatment of ALS The methods described herein include methods (also referred to herein as "screening assays") for identifying compounds that modulate (i.e., increase or decrease) complex formation mediated by the RNA binding proteins identified herein (e.g., Table I, particularly ESWR1 and TAF15). Such compounds include, e.g., polypeptides, peptides, antibodies, peptidomimetics, peptoids, small inorganic molecules, small non-nucleic acid organic molecules, nucleic acids (e.g., antisense nucleic acids, siRNA, oligonucleotides, synthetic oligonucleotides), carbohydrates, or other agents that bind to the target proteins and have a stimulatory or inhibitory effect thereon. Compounds thus identified can be used to modulate the expression or activity of these proteins in a therapeutic protocol.

In general, screening assays involve assaying the effect of a test agent on expression or activity of a target nucleic acid or target protein in a test sample (i.e., a sample containing the target nucleic acid or target protein). Expression or activity in the presence of the test compound or agent can be compared to expression or activity in a control sample (i.e., a sample containing the target protein that is incubated under the same conditions, but without the test compound). A change in the expression or activity of the target nucleic acid or target protein in the test sample compared to the control indicates that the test agent or compound modulates expression or activity of the target nucleic acid or target protein and is a candidate agent.

Compounds to be screened or identified using any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of test compounds through the use of the various libraries herein permits subsequent modification of the test compound "hit" or "lead" to optimize the capacity of the "hit" or "lead" to prevent or suppress aberrant TDP-43-RNA binding protein complex formation.

In one embodiment, assays are provided for screening candidate or test molecules that are substrates of a target protein or a biologically active portion thereof in a cell. In another embodiment, the assays are for screening candidate or test compounds that disrupt complex formation between EWSR1 TAF15 and other proteins.

In one embodiment, a cell-based assay is employed in which a cell, such as the yeast cells described in Example I, is contacted with a test compound. The ability of the test compound to modulate complex formation between EWSR1 and/or TAF15 and TDP-43 and resulting cellular toxicity is then determined. Other cells of mammalian origin, e.g., rat, mouse, or human are also suitable for this purpose.

The ability of the test compound to bind to a target protein or modulate target protein binding to a compound, e.g., a target protein substrate, can also be evaluated. This can be accomplished, for example, by coupling the compound, e.g., the substrate, with a radioisotope or enzymatic label such that binding of the compound, e.g., the substrate, to the target protein can be determined by detecting the labeled compound, e.g., substrate, in a complex. Alternatively, the target protein can be coupled with a radioisotope or enzymatic label to monitor the ability of a test compound to modulate target protein binding to a target protein substrate in a complex. For example, compounds (e.g., target protein substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound to interact with target protein with or without the labeling of any of the interactants can be evaluated. For example, a microphysiometer can be used to detect the interaction of a compound with a target protein without the labeling of either the compound or the target protein (McConnell et al., Science 257:1906-1912, 1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and a target protein.

In yet another embodiment, a cell-free assay is provided in which a target protein or biologically active portion thereof is contacted with a test compound and the ability of the test compound to bind to the target protein or biologically active portion thereof is evaluated. In general, biologically active portions of target proteins to be used in assays described herein include fragments that participate in interactions with other molecules, e.g., fragments with high surface probability scores.

Cell-free assays involve preparing a reaction mixture of the target proteins and the test compound under conditions and for a time sufficient to allow the two components to interact and bind, thus forming a complex that can be removed and/or detected. The ability of a target protein to bind to a target molecule can be determined using real-time Biomolecular Interaction Analysis (BIA) (e.g., Sjolander et al., Anal. Chem., 63:2338-2345, 1991, and Szabo et al., Curr. Opin. Struct. Biol., 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In several of these assays, the target proteins or the test substance is anchored onto a solid phase. The target protein/test compound complexes anchored on the solid phase can be detected at the end of the reaction. Generally, the target proteins are anchored onto a solid surface, and the test compound (which is not anchored) can be labeled, either directly or indirectly, with detectable labels discussed herein. It may be desirable to immobilize either the target protein, an anti-target protein antibody, or its target molecule to facilitate separation of complexed from uncomplexed forms of one or both of the proteins, as well as to accommodate automation of the assay. Binding of a test compound to a target protein, or interaction of a target protein with a target molecule in the presence and absence of a test compound, can be accomplished in any vessel suitable for containing the reactants. Examples of such vessels include microliter plates, test tubes, and micro-centrifuge tubes. In one embodiment, a fusion protein can be provided that adds a domain that allows one or both of the proteins to be bound to a matrix. For example, glutathione-S-transferase/target protein fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein. The mixture is then incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target protein binding or activity determined using standard techniques.

Other techniques for immobilizing a target protein on matrices include using conjugation of biotin and streptavidin. Biotinylated target protein can be prepared from biotin-NHS (N-hydroxy-succinimide) using techniques known in the art (e.g., biotinylation kit, Pierce Chemicals, Rockford, IU.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The complexes anchored on the solid surface can be detected in a number of ways. Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with target protein, but which do not interfere with binding of the target protein to its target molecule. Such antibodies can be derivatized to the wells of the plate, and unbound target protein trapped in the wells by antibody conjugation. Methods for detecting such complexes, in addition to those described above for the GST-immobilized complexes, include immunodetection of complexes using antibodies reactive with the target protein or target molecule, as well as enzyme-linked assays which rely on detecting an enzymatic activity associated with the target protein.

Alternatively, cell-free assays can be conducted in a liquid phase. In such an assay, the reaction products are separated from unreacted components, by any of a number of standard techniques, including but not limited to: differential centrifugation (see, for example, Rivas and Minton, Trends Biochem. Sci., 18:284-7, 1993); chromatography (gel filtration chromatography, ion-exchange chromatography); electrophoresis (e.g., Ausubel et al., eds. Current Protocols in Molecular Biology 1999, J. Wiley: New York.); and immunoprecipitation (see, for example, Ausubel et al., eds., 1999, Current Protocols in Molecular Biology, J. Wiley: New York). Such resins and chromatographic techniques are known to one skilled in the art (e.g., Heegaard, J. Mol. Recognit, 11: 141-148, 1998; Hage et al., J. Chromatogr. B. Biomed. Sci. Appl, 699:499-525, 1997). Further, fluorescence energy transfer may also be conveniently utilized, as described herein, to detect binding without further purification of the complex from solution.

The assay can include contacting the target protein or a biologically active portion thereof with a known compound that binds to the target protein to form an assay mixture, contacting the assay mixture with a test compound, and determining the ability of the test compound to interact with the target protein, wherein determining the ability of the test compound to interact with the target protein includes determining the ability of the test compound to preferentially bind to the target protein or biologically active portion thereof, or to modulate the activity of a target molecule, as compared to the known compound.

A target protein can, in vivo, interact with one or more cellular or extracellular macromolecules, such as proteins. For the purposes of this discussion, such cellular and extracellular macromolecules are referred to herein as "binding partners." Compounds that disrupt such interactions are useful for regulating the activity thereof. Such compounds can include, but are not limited, to molecules such as antibodies, peptides, and small molecules. In general, target proteins for use in identifying agents that disrupt interactions are the target proteins identified herein. To identify compounds that interfere with the interaction between the target protein and its binding partner(s), a reaction mixture containing the target protein and the binding partner is prepared, under conditions and for a time sufficient, to allow the two products to form a complex. To test an inhibitory agent, the reaction mixture is provided in the presence (test sample) and absence (control sample) of the test compound. The test compound can be initially included in the reaction mixture, or can be added at a time subsequent to the addition of the target gene and its cellular or extracellular binding partner. Control reaction mixtures are incubated without the test compound or with a control compound. The formation of complexes between the target protein and the cellular or extracellular binding partner is then detected. The formation of a complex in the control reaction, and less formation of complex in the reaction mixture containing the test compound, indicates that the compound interferes with the interaction of the target protein and the interactive binding partner. Such compounds are candidate compounds for inhibiting the expression or activity or a target protein. Additionally, complex formation within reaction mixtures containing the test compound and normal target protein can also be compared to complex formation within reaction mixtures containing the test compound and mutant target gene product. This comparison can be important in those cases wherein it is desirable to identify compounds that disrupt interactions of mutant but not normal target protein.

Binding assays can be carried out in a liquid phase or in heterogenous formats. In one type of heterogeneous assay system, either the target protein or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

In another embodiment, modulators of target expression (RNA or protein) are identified. For example, a cell or cell-free mixture is contacted with a test compound and the expression of target mRNA (e.g., EWSR1 encoding mRNA) or protein evaluated relative to the level of expression of target mRNA or protein in the absence of the test compound. When expression of target mRNA or protein is greater in the presence of the test compound than in its absence, the test compound is identified as a stimulator (candidate compound) of target mRNA or protein expression. Alternatively, when expression of target mRNA or protein is less (statistically significantly less) in the presence of the test compound than in its absence, the test compound is identified as an inhibitor (candidate compound) of target mRNA or protein expression. The level of target mRNA or protein expression can be determined by methods described herein and methods known in the art such as Northern blot or Western blot for detecting target mRNA or protein.

In another aspect, the methods described herein pertain to a combination of two or more of the assays described herein. For example, a modulating agent can be identified using a cell-based or a cell-free assay, and the ability of the agent to modulate the activity of a target protein can be confirmed in vivo, e.g., in an animal such as an animal model for ALS.

This invention further pertains to novel agents identified by the above-described screening assays. Accordingly, it is within the scope of this invention to further use an agent (compound) identified as described herein (e.g., a target protein modulating agent, an anti sense nucleic acid molecule, an siRNA, a target protein-specific antibody, or a target protein-binding partner) in an appropriate animal model to determine the efficacy, toxicity, side effects, or mechanism of action, of treatment with such an agent. Furthermore, novel agents identified by the above-described screening assays can be used for treatments as described herein.

Compounds that modulate target protein expression or activity (target protein modulators) can be tested for their ability to affect metabolic effects associated with the target protein, e.g., with decreased expression or activity of target protein using methods known in the art and methods described herein. For example, the ability of a compound to modulate EWSR1 and/or TAF15/TDP-43 complex formation and associated toxicity can be tested using an in vitro or in vivo model for ALS.

The compounds identified above can be synthesized by any chemical or biological method. The compounds identified above can also be pure, or may be in a heterologous composition (e.g., a pharmaceutical composition), and can be prepared in an assay-, physiologic, or pharmaceutically-acceptable diluent or carrier (see below).

Pharmaceutical Compositions

A compound that is found to prevent or suppress aberrant TDP-43-EWSR1 and/or TAF15 complex formation and cytotoxicity in a cell can be formulated as a pharmaceutical composition, e.g., for administration to a subject to treat ALS.

A pharmaceutical composition typically includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The compound can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X). In one embodiment, a compound that prevents or suppresses aberrant TDP-43-RNA binding protein complex formation and cytotoxicity in a cell can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C. The pharmaceutical compositions may be in a variety of forms. These include, for example, liquid, semi-solid and solid dosage forms, such as liquid solutions {e.g., injectable and infusible solutions), dispersions or suspensions, tablets, capsules, pills, powders, liposomes and suppositories. The preferred form can depend on the intended mode of administration and therapeutic application. Typically compositions for the agents described herein will be in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating a compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of a compound plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the compound can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978. A compound identified as one that prevents or suppresses aberrant TDP-43-RNA binding protein complex formation and cytotoxicity in a cell can be modified, e.g., with a moiety that improves its stabilization and/or retention in circulation, e.g., in blood, serum, or other tissues, e.g., by at least 1.5, 2, 5, 10, or 50 fold. The modified compound can be evaluated to assess whether it can reach treatment sites of interest.

For example, the compound can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, a compound can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the compound is used in combination with a second agent (e.g., any additional therapies for a proteinopathy such as a decongestant or Rilutek®), the two agents can be formulated separately or together. For example, the respective pharmaceutical compositions can be mixed, e.g., just prior to administration, and administered together or can be administered separately, e.g., at the same or different times as elaborated below.

The following materials and methods are provided to facilitate the practice of the present invention.

Plasmids, Yeast Strains and Media

The yeast strain used in the human RRM screen and follow-up analyses was BY4741 [genotype, Mata his3Δ1 leu2Δ0 met15Δ0 ura3Δ0]. Strains were manipulated and media prepared using standard techniques (Guthrie and Fink, 2002). EWSR1 and TAF15 expression constructs were generated by Gateway® cloning (Invitrogen), starting with entry clones in pDONR221 and shuttled from entry clones into a modified PGW vector (for motor neuron transfection experiments), created by incorporating the Gateway B cassette into the Sma1 site of the PGW vector using the Gateway conversion kit (Invitrogen). ALS patient mutations in EWSR1 and TAF15 were introduced by site-directed mutagenesis using the QuickChange Site Directed Mutagenesis kit (Stratagene).

Human RNA Binding Protein Plasmid Library

We constructed a library of yeast expression plasmids containing 133 unique human RRM-containing open reading frames (ORFs). The ORFs were obtained from the human ORFeome collection (Open Biosystems) as Gateway® entry clones in plasmid pDONR223. We selected 133 unique clones contained within the library predicted to encode RRM-domain proteins (PFAM ID PF00076). ORFs from the entry clones were shuttled into the 2-micron galactose-inducible yeast expression plasmid pAG426Gal-ccdB-EYFP by Gateway® LR cloning reaction (Alberti et al., 2007) to generate C-terminally tagged RRM-protein-YFP fusions. Restriction digest and DNA sequencing were used to confirm the integrity of each expression construct.

Yeast Transformation and Spotting Assays

The PEG/lithium acetate method was used to transform yeast with each plasmid DNA from the RRM ORF library (Ito et al., 1983). For spotting assays, yeast cells were grown overnight at 30° C. in liquid media containing raffinose (SRaf/-Ura) until log or mid-log phase. Cultures were then normalized for $OD_{600}$, serially diluted and spotted onto synthetic solid media containing glucose or galactose lacking uracil, and were grown at 30° C. for 2-3 d.

Microscopy

For fluorescence microscopy experiments, single colony isolates of the yeast strains were grown to mid-log phase in SRaf/-Ura media at 30° C. Cultures were spun down and resuspended in the same volume of SGal/-Ura to induce expression of the TDP-43 constructs. Cultures were induced with galactose for 4-6 h and processed for microscopy. Images were obtained using an Olympus IX70 inverted microscope and a Photometrics CoolSnap HQ 12-bit CCD camera.

Prion-prediction Algorithm

Proteins were parsed into prion-like and non-prion-like regions using a Hidden Markov Model developed to identify regions that have the unusual amino acid composition characteristic of yeast prions (Alberti et al., 2009; Cushman et al., 2010). Prion-like regions of length≥60 were given a prion-domain score, defined as the maximum log-likelihood for the prion-like state vs. the non-prion-like state over any 60 consecutive amino acids within the regions (Alberti et al., 2009). Among the 21,873 human genes analyzed (Ensembl GrCh37.59), 246 had prion-like regions of length>60, and were ranked by prion-domain score. For genes with multiple transcripts, the longest one was used, with the one with lowest Ensembl Transcript ID used in case of ties.

Sequencing EWSR1 and TAF15 Genes in ALS Patients and Controls

Genomic DNA from non-Latino Caucasian individuals with sporadic ALS (N=552) was obtained from the Coriell Institute for Medical Research (Coriell, Camden, N.J.) distributed in 96-well plates NDPT025, NDPT026, NDPT030, NDPT100, NDPT103, and NDPT106. Additional genomic DNA samples from patients verified to meet El Escorial criteria for definite or probable ALS by a neurologist (N=258) or with neuropathologic findings consistent with ALS (N=88) were obtained from the University of Pennsylvania (PENN) Center for Neurodegenerative Disease Research (CNDR). All subjects were collected with PENN Institutional Review Board approval. The racial background of the PENN subjects was 90% non-Latino Caucasian, 5% Black, and 5% mixed or other. The PENN subjects were 57% male and had an average age of onset of 57 years (8-89) and an average duration of disease of 4 years (range 1-46). A family history of ALS (FALS) was present in 29 of 250 patients (11.6%) for which family history was available. Mutations in SOD1 and FUS/TLS were excluded in all the familial ALS cases and TAR-DBP mutations excluded in all PENN cases. All cases with potentially pathogenic variants in EWSR1 and TAF15 were also sequenced for TARDBP, FUS, and SOD1.

679 neurologically normal control samples from Coriell were distributed in 96-well plates NDPT084, NDPT090, NDPT093, NDPT094, NDPT095, NDPT096, NDPT098, and NDPT099. An additional 90 neurologically normal control samples were obtained from the Children's Hospital of Philadelphia (CHOP). 179 DNA samples from cognitively normal individuals>60 years of age were obtained from the National Cell Repository for Alzheimer's Disease (NCRAD, Indianapolis, Ind.).

We sequenced exons 15-18 of EWSR1 and exons 13-16 of TAF15, which encode the C-terminal domains of EWSR1 and TAF15, respectively. EWSR1 was sequenced in 817 ALS cases (N=514 Coriell and N=303 PENN) and 1,082 controls. TAF15 was sequenced in 610 ALS cases (N=406 Coriell and N=204 PENN) and 982 controls. Bidirectional sequencing was performed by separately amplifying EWSR1 exons 15-16, 17, and 18 and TAF15 exons 13-15 and 16 from samples using the polymerase chain reaction (PCR). PCR primers and cycling conditions used for amplification and sequencing are available upon request. Amplicons were purified, processed and sequenced using Big-Dye® Terminator v3.1 sequencing (Applied Biosystems). All variants identified were confirmed by repeat sequencing. Sequence analysis was performed using Sequencher DNA Software.

SNP Genotyping

DNA samples from 4811 de-identified healthy control subject of European ancestry who were recruited from the Children's Hospital of Philadelphia (CHOP) Health Care Networks (parents of children cared for at CHOP) were screened for mutations in the EWSR and TAF15 genes, using a custom designed TaqMan SNP genotyping assay from Applied Biosystems. PCR and reporter primer sequences are available upon request.

A total of 10 ng of DNA was used as a template for the PCR reactions. Samples were run on the 7900HT analyzer from Applied Biosystems, after pooling three samples per run to expedite the screening process. Along with the pooled samples, each 384-well plate contained a positive and non-template control (NTC). Subsequent end-point allelic discrimination was performed, using SDSv2.4 software from Applied Biosystems. To ensure mutations were captured from the pooled approach, a test plate was run with mixtures of 1 heterozygous (het) positive and 1 homozygous (hom) negative sample; 1 het pos and 2 hom neg; and 1 het pos and 3 hom neg. The positive alleles were detected in all pools and a mixture of 3 unknowns was ultimately chosen for the study.

Genetic Analysis of EWSR1 and TAF15 Genes in ALS Replication Series from Mayo Clinic The Mayo Clinic ALS replication series consisted of 105 unrelated ALS patients (56 males, 49 females) from a consecutive clinical case series seen at Mayo Clinic Florida by the ALS Center in the period 2008-2010 and 20 pathologically confirmed ALS patients selected from the Mayo Clinic Florida Brain Bank (7 males, 13 females). All patients agreed to be in the study and biological samples were obtained after informed consent. Mutations in SOD1, FUS/TLS or TAR-DBP were previously excluded in all patients included in this patient series (add reference to DeJesus-Hernandez et al., Human Mutation, 2010). The average age of onset in our clinical patient population was 57.2±10.6 years (range 17-78 years), while the average age at death in pathologically confirmed samples was 68.9±12.1 years (range 46-83 years). 16.0% of patients showed a positive family history of ALS defined as having at least one affected relative within 3 generations. DNA samples of 812 healthy control individuals (range 51-99 years) were also ascertained at the Department of Neurology at Mayo Clinic Florida and 92 autopsy samples of neurologically normal individuals were selected from the Mayo Clinic Florida Brain Bank. The racial background of all ALS patients and controls was non-Latino Caucasian.

For all 125 ALS patient included in this replication series PCR amplification was performed for exons 17-18 of EWSR1 and exons 15-16 of TAF15, using primers designed to flanking intronic sequences using Qiagen products (Qiagen, Valencia, Calif., USA) (PCR conditions and primer sequences available on request). PCR products were purified using the Ampure system (Agencourt Bioscience Corporation, Beverly, Mass., USA) and sequenced using Big dye terminator V.3.1 products (Applied Biosystems, Foster City, Calif., USA). Sequencing products were purified using the CleanSEQ method (Agencourt) and analyzed on an ABI 3730 DNA analyzer (Applied Biosystems). Sequence analysis was performed using Sequencher software (Gene Codes, Ann Arbor, Mich., USA). All variants identified were confirmed by repeat sequencing. The Gly473Glu variant in TAF15 was further genotyped in the 904 control individuals from Mayo Clinic using a custom designed TaqMan SNP genotyping assay (ABI).

EWSR1 and TAF15 Protein Purification

TDP-43 and FUS were purified as described (Johnson et al., 2009; Sun et al., 2010). EWSR1 and TAF15 were expressed and purified from *E. coli* as GST-tagged proteins. EWSR1 and TAF15 were cloned into GV13 to yield GST-TEV-EWSR1 or GST-TEV-TAF15, and overexpressed in *E. coli* BL21 Star (Invitrogen). Protein was purified over a glutathione-sepharose column (GE) according to manufacturer's instructions. GST-EWSR1 and GST-TAF15 were eluted from the glutathione sepharose with 50 mM Tris-HCl pH 7.4, 100 mM potassium acetate, 200 mM trehalose, 0.5 mM EDTA and 20 mM glutathione. After purification, proteins were concentrated to 10 µM or greater using Amicon Ultra-4 centrifugal filter units (10 kDa molecular weight cut-off; Millipore). Protein was then filtered through a 0.22 µm filter to remove any aggregated material. After filtration, the protein concentration was determined by Bradford assay (Bio-Rad) and the proteins were used immediately for aggregation reactions.

EWSR1 and TAF15 In Vitro Aggregation Assays

Filtered, purified GST-EWSR1 and GST-TAF15 proteins were used immediately for aggregation assays. Aggregation was initiated by the addition of TEV protease (Invitrogen) to EWSR1 or TAF15 (3 µM) in assembly buffer (AB): 50 mM TrisHCl pH 7.4, 100 mM potassium acetate, 200 mM trehalose, 0.5 mM EDTA and 20 mM glutathione. Aggregation reactions were incubated at 25° C. for 0-90 min with agitation at 700 rpm in an Eppendorf Thermomixer. No aggregation occurred unless TEV protease was added to separate GST from EWSR1 or TAF15. Turbidity was used to assess aggregation by measuring absorbance at 395 nm. For sedimentation analysis, reactions were centrifuged at 16,100 g for 20 min at 25° C. Supernatant and pellet fractions were then resolved by SDS-PAGE and stained with Coomassie Brilliant Blue, and the amount in either fraction determined by densitometry in comparison to known quantities of EWSR1 or TAF15. For electron microscopy (EM) of in vitro aggregation reactions, protein samples (20 µl of a 3 µM solution) were adsorbed onto glow-discharged 300-mesh Formvar/carbon-coated copper grid (Electron Microscopy Sciences) and stained with 2% (w/v) aqueous uranyl acetate. Excess liquid was removed, and grids were allowed to air dry. Samples were viewed using a JEOL 1010 transmission electron microscope.

*Drosophila* Experiments

Transgenic flies expressing human EWSR1 and TAF15 were generated by standard techniques using the pUAST vector. TDP-43 transgenic flies are described in (Elden et al., 2010). To direct transgene expression to the eye, gmr-GAL4 driver was used. To direct expression to motor neurons, D42-GAL4 driver was used. Locomotor activity was assessed using a climbing assay as described in (Elden et al.).

EWSR1 and TAF15 Plasmids and Cell Culture

TAF15 and EWS wild type and mutants were amplified by PCR using the following primers: hTAF15 specific primers (Forward, hTAF15SpeIKozMFlagf 5'-CCC GGG ACT AGT CAC CAT GGA CTA CAA GGA CGA CGA TGA CAA AAT GTC GGA TTC TGG AAG T-3' (SEQ ID NO: 1); Reverse, hTAF15MycNotIr 5'CAC GCG GCC GCC TAC AGA TCC TCT TTC TGA GAT GAG TTT TTG TTC GTA TGG TCG GTT GCG C-3' (SEQ ID NO: 2)), hEWS specific primers (Forward, hEWSKozMFlagf 5'-TCA CCA TGG ACT ACA AGG ACG ACG ATG ACA AAA TGG CGT CCA CGG ATT ACA G-3' (SEQ ID NO: 3); Reverse, hEWSMycNotIr 5'-CAC GCG GCC GCC TAC AGA TCC TCT TCT GAG ATG AGT TTT TGT TCG TAG GGC CGA TCT CTG-3' (SEQ ID NO: 4)). PCR amplified fragments were cloned into the pEN-Tmcs entry vector using T4 DNA ligase (Promega) and recombined by LR-clonase (Invitrogen) into pSILK-Neo destination vector (Signaling-gateway) to obtain pSILK-TAF15/EWS wild type and mutants plasmids. Mouse embryonic stem cells (ES) were maintained in ES medium (DMEM, 15% FBS, 1× Penicillin/streptomycin, 1× Glutamax, 1× Non-essential amino acid, 1× Sodium Pyruvate, 0.1 mM beta-mercaptoethanol, 1000 u/ml LIF, 25 µM PD98059) on a gelatinized plate without feeder cells. For differentiation, the protocol of Wichterle, H. and colleagues was followed (Wichterle et al., 2009). Briefly, 1×10⁶ ES cells were cultured with ADFNK medium (45% Advanced DMEM/F12, 45% Neurobasal medium, 10% knockout serum replacement, 1× Penicillin/streptomycin, 1×L-Glutamine, 0.1 mM beta-mercaptoethanol) for five days to form embryonic bodies (EBs)-small floating aggregates of ES cells. EBs were utilized for neurons culture on day 6 of differentiation. ES cells differentiated into neuron were dissociated into single cells and plated on a Poly-L-lysine/laminin coated 12-well chamber or Nunc 8-well chambers with ADFNB+ GDNF medium (49% Advanced DMEM/F12, 49% Neurobasal medium, 2% B27 supplement, 1× Penicillin/streptomycin, 1×L-Glutamine, 5 ng/ml GDNF).

Lentivirus Production and Transduction

The pSLIK expression lentivector was transfected along with lentivirus packaging and pseudotyping plasmids into 293T cells using Lipofectamine 2000 reagent (Invitrogen) following manufacturer's instructions. 293T cells were cultured in DMEM (GIBCO Invitrogen) and 10% Fetal plex serum (Gemini). Plasmids were cotransfected by using 6 μg of pSLIK plasmid, 4.5 μg of the packaging plasmid psPAX2 (Addgene) and 3 μg of the vesicular stomatitis virus (VSV) G envelope plasmid pMD2 (Addgene) diluted in Opti-MEM (Gibco Invitrogen). The viral supernatant was collected 48 h after transfection, passed through 0.45 μm-pore size filters and concentrated by ultracentrifugation onto a 20% sucrose gradients using SW41 rotor (Beckman) at 20,000 rpm for 2 hrs at 4° C. Viral pellets were resuspended in ADFNB medium and stored in aliquots at −80° C. For transduction, cells were mixed with the virus at a low MOI to ensure<30% infection frequency such that the majority of transduced cells contained single viral integrants. Four micrograms of polybrene/ml (Sigma) was included and cells were plated on either a 12-well chamber or Nunc 8-well chambers (56815-1PAK; Fisher). To induce protein expression, 1 μg/ml Doxycycline (DOX; Milipore) was added to the cells 24 hrs after transduction and for five days.

Immunofluorescence Analysis

For immunostaining, neurons were washed 3× with 1×PBS, fixed for 30 min with 3.7% paraformaldehyde, permeabilized using 0.1% Triton X-100 for 10 min, blocked with 3% BSA in PBS for 15 min and incubated overnight at 4° C. with primary antibodies as follows: anti-TAF15 (1:3,000; Bethyl, A300-A308), anti-EWS (1:4,000; Santa cruz, sc-28327), anti-FLAG M2 (1:5,000; Sigma, F1804-IMG). Cells were washed 3× with 1×PBS and incubated with either Alexa-Fluor 555 goat anti-rabbit IgG (1:1,000; MolecularProbes, A21429) or Alexa-Fluor 555 goat anti-mouse IgG (1:1,000; MolecularProbes, A21424). Cells were mounted with prolong plus DAPI (Invitrogen) and were visualized with an Olympus BX-60 microscope. Images were recorded with a Spot Digital camera.

Cell Fractionation and Immunoblot Analysis

For Western blot analysis, 5×10$^5$ cells of neurons, transduced with pSLIK lentivectors expressing TAF15 or EWS wild type and mutants and induced with 1 μg/ml DOX for 5 days, were lysed using RIPA buffer (0.1% SDS, 0.5% Deoxycholate, 1% NP-40, 150 mM NaCl, 50 mM Tris-HCl pH 8.0) for 10 mM on ice and centrifuged at 13,000 rpm for 10 min to obtain the soluble fractions. Pellets were lysed with Urea buffer (7M Urea, 2M Thiourea, 4% CHAPS, 30 mM Tris pH 8.5) and were sonicated to obtain the insoluble fractions. Cell lysates were separated by Nu-PAGE (4-12% gradient gels; Invitrogen), transferred to nitrocellulose membranes and analyzed by Western blotting with ECL plus detection reagents (GE Healthcare). Primary antibodies used were as follows: anti-FLAG M2 (1:10,000; Sigma), anti-GAPDH (1:20,000; Sigma). A secondary anti-mouse Ig HRP antibody was used at a dilution of 1:10,000. Membranes were developed using X-ray film (Kodak).

Mouse Primary Motor Neuron Transfection and Immunofluorescence

Primary neuron cultures were transfected after 5 days in vitro using Lipofectamine LTX with PLUS reagent (Invitrogen) according to the manufacturers protocol in media lacking antibiotics. Media was replaced 12 hours following transfection with media containing antibiotics. Cells were harvested for immunoflourescence 96 hours after transfection, briefly, cultures were washed in PBS and fixed in 4% paraformaldehyde 15 min, then washed in 1×PBS 4×. Cells were blocked for 1 h in blocking solution (2% Fetal Bovine Serum, 0.02% Triton X-100, 1×PBS), and then incubated 1 h in primary antibody at RT. Cells were then washed 3× in PBS, then incubated with secondary antibody 1 h RT. Cells were then washed with blocking solution and mounted in Vectashield mounting media with DAPI (Vector). Antibodies used were: α-EWSR1 mouse antibody (Santa Cruz), 1:1000; α-TAF15 rabbit antibody (Bethyl Laboratories), α-Doublecortin goat antibody (Santa Cruz) 1:500; Cy-3 conjugated α-mouse IgG (Jackson Immunoresearch), 1:250; and Cy-3 conjugated α-rabbit IgG (Jackson Immunoresearch), 1:250; and Cy-2 conjugated α-goat IgG (Jackson Immunoresearch), 1:250. Cells were visualized by light microscopy. Localization of endogenous, or transfected wild-type or mutant EWSR1 was quantified using blinded analysis of random fields of cells. The number of neurons with EWSR1 staining in processes was divided by the total number of neurons counted to yield the percent of neurons with EWSR1 in neuronal processes. More than 50 neurons were analyzed for each condition. Neurons were identified using morphology and doublecortin staining.

Immunohistochemistry

Formalin-fixed, paraffin-embedded human spinal cord sections were deparaffinized before pretreatment using heat antigen retrieval with Bull's Eye Decloaker (BioCare Medical). Endogenous peroxidase was then blocked with 3% hydrogen peroxide in PBS for 10 minutes. After washing with 0.1% PBST blocking was performed with 10% goat serum, 0.5% PBST for 30-60 minutes at 25° C. Sections were incubated with mouse anti-EWSR1 (1:125; Santa Cruz Biotechnology) or rabbit anti-TAF15 (1:250; Bethyl Laboratories) in 0.1% PBST overnight at 4° C. After washing with 0.1% PBST, sections were incubated with biotinylated goat anti-mouse or rabbit IgG (1:200; Vector Laboratories) for 1 hour at 25° C. After washing with 0.1% PBST, sections were then incubated with Vectastain ABC (Vector Laboratories) for 45 minutes. After washing with 0.1% PBST followed by 0.1M Tris (pH 7.5) and 0.3M NaCl. Peroxidase activity was then detected with DAB (Sigma). Detailed immunohistochemistry protocols are available on the world wide web at med.PENN.edu/mcrc/histology_core/.

Statistical Analysis

Two-tailed Fisher's exact tests were used to evaluate genetic association between EWSR1 and TAF15 sequence variants and ALS.

The following examples are provided to illustrate certain embodiments of the invention. They are not intended to limit the invention in any way.

EXAMPLE 1

A Yeast Functional Screen Identifies New ALS Disease Genes

Here we report a simple yeast functional screen to identify human proteins with similar properties as TDP-43 and FUS, combined with genetic analysis in human ALS patients, for mutations in two genes from this screen, EWSR1 and TAF15. We show that EWSR1 and TAF15 have similar in vitro and in vivo properties as TDP-43 and FUS and the disease-associated variants affect localization in motor neurons. The identification of mutations in two additional RNA binding proteins underscores a key role for RNA metabolism defects in ALS and suggests that this class of aggregation-prone RNA binding proteins might contribute very broadly to the disease. Having established the effectiveness of this approach in predicting new ALS disease genes, the yeast functional screen promises to facilitate ALS disease gene discovery.

TDP-43 and FUS are both RNA recognition motif (RRM)-containing proteins (RRM proteins) (Lagier-Tourenne and Cleveland, 2009) and both form cytoplasmic inclusions and are toxic when expressed in yeast (FIG. 1a and (Johnson et al., 2008; Johnson et al., 2009)). Including FUS and TDP-43, there are least 213 RRM proteins (PFAM ID PF00076) present in the human proteome (Table 2). This raised the question of whether other human RRM proteins would show properties like TDP-43 and FUS (e.g. aggregation-prone and toxic in yeast), and, if so, could these properties predict that these genes are potential ALS disease genes? We therefore designed a simple yeast functional screen to identify such genes (FIG. 1b). Of the 213 human RRM proteins, we were able to obtain a gene clone for 132. We cloned these 132 different human RRM-containing open reading frames (ORFs) into yeast expression vectors as YFP fusion proteins, under the control of a galactose-inducible promoter, and individually transformed them into yeast cells. We have previously found that the addition of the YFP tag to TDP-43 and FUS does not affect the aggregation or toxicity properties ((Johnson et al., 2008; Johnson et al., 2009; Sun et al., 2010) and data not shown). Fluorescence microscopy was used to determine the localization of each protein (nuclear, cytoplasmic, diffuse, foci; FIG. 1c and Table 2) and spotting assays were used to assess toxicity (FIG. 1d and Table 2). Some proteins localized to the nucleus (39/132) whereas others were diffusely localized in the cytoplasm (27/132). Interestingly, several others formed multiple foci in the cytoplasm in a pattern strikingly similar to that of FUS and TDP-43 (52/132). Of the proteins that accumulated in the cytoplasm, 35 were also toxic, including FUS and TDP-43 (Table 1). Thus, 35 of 132 human RRM proteins behave like FUS and TDP-43 in yeast cells.

TABLE 1

Human RRM proteins with similar properties as FUS and TDP-43 when expressed in yeast.

| Name | Description | Toxicity Score (1-4) | Prion domain score | Prion domain rank |
|---|---|---|---|---|
| 1. BOLL | boule-like (*Drosophila*) | 2 | | |
| 2. CPSF6 | cleavage and polyadenylation specific factor | 2.5 | | |
| 3. DAZ1 | deleted in azoospermia 1 | 2.5 | 14 | 143 |
| 4. DAZ2 | deleted in azoospermia 2 | 3 | 14 | 143 |
| 5. DAZ3 | deleted in azoospermia 3 | 3.5 | 15 | 136 |
| 6. DAZAP1 | DAZ associated protein 1 | 2 | 12 | 198 |
| 7. ELAVL1 | ELAV (embryonic lethal, abnormal vision)-like 1 | 1 | | |
| 8. ELAVL2 | ELAV (embryonic lethal, abnormal vision)-like 2 | 1 | | |
| 9. ELAVL3 | ELAV (embryonic lethal, abnormal vision)-like 3 | 2.5 | | |
| 10. ELAVL4 | ELAV (embryonic lethal, abnormal vision)-like 4 | 1 | | |
| 11. ENOX1 | ecto-NOX disulfide-thiol exchanger 1 | 2.5 | | |
| 12. EWSR1 | Ewing sarcoma breakpoint region 1 | 3.5 | 32 | 25 |
| 13. FUS | fusion (involved in malignant liposarcoma) | 1.5 | 38 | 13 |
| 14. G3BP1 | Ras-GTPase-activating protein | 2 | | |
| 15. HNRNPA0 | heterogeneous nuclear ribonucleoprotein | 1 | 21 | 81 |
| 16. HNRNPM | heterogeneous nuclear ribonucleoprotein | 3 | | |
| 17. IGF2BP2 | IGF-II mRNA-binding protein 2 | 2.5 | | |
| 18. IGF2BP3 | IGF-II mRNA-binding protein 3 | 2.5 | | |
| 19. MSI2 | musashi homolog 2 | 2 | | |
| 20. RALYL | RNA binding protein-like | 2.5 | | |
| 21. RBM12B | RNA binding motif protein | 3.5 | | |
| 22. RBM14 | RNA binding motif protein | 2 | 16 | 117 |
| 23. RBM4 | RNA binding motif protein | 3 | | |
| 24. RBM41 | RNA binding motif protein | 2.5 | | |
| 25. RBM4B | RNA binding motif protein | 2.5 | | |
| 26. RBM5 | RNA binding motif protein | 3 | | |
| 27. RBM9 | RNA binding motif protein | 3.5 | | |
| 28. RBMS1 | RNA binding motif, single stranded interacting protein | 2 | | |
| 29. RBMS2 | RNA binding motif, single stranded interacting protein | 2 | | |
| 30. RBPMS | RNA binding motif, single stranded interacting protein | 3 | | |
| 31. ROD1 | regulator of differentiation | 1 | | |
| 32. SNRPA | small nuclear ribonucleoprotein polypeptide | 2 | | |
| 33. SNRPB2 | small nuclear ribonucleoprotein polypeptide | 2 | | |
| 34. TARDBP | TAR DNA binding protein (TDP-43) | 1.5 | 27 | 43 |
| 35. TIA1 | cytotoxic granule-associated RNA binding protein | 2 | 23 | 55 |

A list of 35 human RRM proteins that formed cytoplasmic aggregates and were toxic when expressed in yeast.

Toxicity was scored from 1 (most toxic) to 4 (not toxic).

Prion domain score, based on [10,11], indicates the maximum log-likelihood for prion-like amino acid composition vs. non-prion-like amino acid composition in any 60 consecutive amino acid window contained in a region parsed as prion-like by the Hidden Markov Model.

No prion score inindicates that no region of length ≥60 was parsed as prion-like.

Prion domain rank is out of 21,873 human proteins.

TABLE 2

| Gene Name | Ensembl Gene ID | Chromosome | Description |
| --- | --- | --- | --- |
| ELAVL1 | ENSG00000066044 | 19 | ELAV (embryonic lethal, abnormal vision, *Drosophila*)-like 1 (Hu antigen R) [Source: HGNC Symbol; Acc: 3312] |
| ELAVL2 | ENSG00000107105 | 9 | ELAV (embryonic lethal, abnormal vision, *Drosophila*)-like 2 (Hu antigen B) [Source: HGNC Symbol; Acc: 3313] |
| ELAVL4 | ENSG00000162374 | 1 | ELAV (embryonic lethal, abnormal vision, *Drosophila*)-like 4 (Hu antigen D) [Source: HGNC Symbol; Acc: 3315] |
| HNRNPA0 | ENSG00000177733 | 5 | heterogeneous nuclear ribonucleoprotein A0 [Source: HGNC Symbol; Acc: 5030] |
| ROD1 | ENSG00000119314 | 9 | ROD1 regulator of differentiation 1 (*S. pombe*) [Source: HGNC Symbol; Acc: Acc: 10253] |
| FUS | ENSG00000089280 | 16 | fused in sarcoma [Source: HGNC Symbol; Acc: 4010] |
| TARDBP | ENSG00000120948 | 1 | TAR DNA binding protein [Source: HGNC Symbol; Acc: 11571] |
| BOLL | ENSG00000152430 | 2 | bol, boule-like (*Drosophila*) [Source: HGNC Symbol; Acc: 14273] |
| DAZAP1 | ENSG00000071626 | 19 | DAZ associated protein 1 [Source: HGNC Symbol; Acc: 2683] |
| G3BP1 | ENSG00000145907 | 5 | GTPase activating protein (SH3 domain) binding protein 1 [Source: HGNC Symbol; Acc: 30292] |
| MSI2 | ENSG00000153944 | 17 | musashi homolog 2 (*Drosophila*) [Source: HGNC Symbol; Acc: 18585] |
| RBM14 | ENSG00000239306 | 11 | RNA binding motif protein 14 [Source: HGNC Symbol; Acc: 14219] |
| RBMS1 | ENSG00000153250 | 2 | RNA binding motif, single stranded interacting protein 1 [Source: HGNC Symbol; Acc: 9907] |
| RBMS2 | ENSG00000076067 | 12 | RNA binding motif, single stranded interacting protein 2 [Source: HGNC Symbol; Acc: 9909] |
| SNRPA | ENSG00000077312 | 19 | small nuclear ribonucleoprotein polypeptide A [Source: HGNC Symbol; Acc: 11151] |
| SNRPB2 | ENSG00000125870 | 20 | small nuclear ribonucleoprotein polypeptide B" [Source: HGNC Symbol; Acc: 11155] |
| TIA1 | ENSG00000116001 | 2 | TIA1 cytotoxic granule-associated RNA binding protein [Source: HGNC Symbol; Acc: 11802] |
| CPSF6 | ENSG00000111605 | 12 | microRNA 1279 [Source: HGNC Symbol; Acc: 35357] |
| DAZ1 | ENSG00000188120 | Y | deleted in azoospermia 1 [Source: HGNC Symbol; Acc: 2682] |
| ELAVL3 | ENSG00000196361 | 19 | ELAV (embryonic lethal, abnormal vision, *Drosophila*)-like 3 (Hu antigen C) [Source: HGNC Symbol; Acc: 3314] |
| ENOX1 | ENSG00000120658 | 13 | ecto-NOX disulfide-thiol exchanger 1 [Source: HGNC Symbol; Acc: 25474] |
| IGF2BP2 | ENSG00000073792 | 3 | insulin-like growth factor 2 mRNA binding protein 2 [Source: HGNC Symbol; Acc: 28867] |
| IGF2BP3 | ENSG00000136231 | 7 | insulin-like growth factor 2 mRNA binding protein 3 [Source: HGNC Symbol; Acc: 28868] |
| RALYL | ENSG00000184672 | 8 | RALY RNA binding protein-like [Source: HGNC Symbol; Acc: 27036] |
| RBM41 | ENSG00000089682 | X | RNA binding motif protein 41 [Source: HGNC Symbol; Acc: 25617] |
| RBM4B | ENSG00000173914 | 11 | RNA binding motif protein 4B [Source: HGNC Symbol; Acc: 28842] |
| DAZ2 | ENSG00000205944 | Y | deleted in azoospermia 2 [Source: HGNC Symbol; Acc: 15964] |
| HNRNPM | ENSG00000099783 | 19 | heterogeneous nuclear ribonucleoprotein M [Source: HGNC Symbol; Acc: 5046] |
| RBM4 | ENSG00000173933 | 11 | RNA binding motif protein 4 [Source: HGNC Symbol; Acc: 9901] |
| RBM5 | ENSG00000003756 | 3 | RNA binding motif protein 5 [Source: HGNC Symbol; Acc: 9902] |
| RBPMS | ENSG00000157110 | 8 | RNA binding protein with multiple splicing [Source: HGNC Symbol; Acc: 19097] |
| DAZ3 | ENSG00000187191 | Y | deleted in azoospermia 3 [Source: HGNC Symbol; Acc: 15965] |
| EWSR1 | ENSG00000182944 | 22 | Ewing sarcoma breakpoint region 1 [Source: HGNC Symbol; Acc: 3508] |
| RBM12B | ENSG00000183808 | 8 | RNA binding motif protein 12B [Source: HGNC Symbol; Acc: 32310] |
| RBM9 | ENSG00000100320 | 22 | RNA binding motif protein 9 [Source: HGNC Symbol; Acc: 9906] |
| A1CF | ENSG00000148584 | 10 | APOBEC1 complementation factor [Source: HGNC Symbol; Acc: 24086] |
| AC005774.2 | ENSG00000078328 | 16 | Fox-1 homolog A (Ataxin-2-binding protein 1)(Hexaribonucleotide-binding protein 1) [Source: UniProtKB/Swiss-Prot; Acc: O9] |
| HNRPDL | ENSG00000152795 | 4 | heterogeneous nuclear ribonucleoprotein D-like [Source: HGNC Symbol; Acc: 5037] |
| MYEF2 | ENSG00000104177 | 15 | myelin expression factor 2 [Source: HGNC Symbol; Acc: 17940] |
| PABPC1 | ENSG00000070756 | 8 | poly(A) binding protein, cytoplasmic 1 [Source: HGNC Symbol; Acc: 8554] |
| PABPC5 | ENSG00000174740 | X | poly(A) binding protein, cytoplasmic 5 [Source: HGNC Symbol; Acc: 13629] |
| PSPC1 | ENSG00000121390 | 13 | paraspecide component 1 [Source: HGNC Symbol; Acc: 20320] |
| RBM11 | ENSG00000185272 | 21 | RNA binding motif protein 11 [Source: HGNC Symbol; Acc: 9897] |
| RBM15 | ENSG00000162775 | 1 | RNA binding motif protein 15 [Source: HGNC Symbol; Acc: 14959] |
| RBM28 | ENSG00000106344 | 7 | RNA binding motif protein 28 [Source: HGNC Symbol; Acc: 21863] |
| RBM3 | ENSG00000102317 | X | RNA binding motif (RNP1, RRM) protein 3 [Source: HGNC Symbol; Acc: 9900] |
| RBM47 | ENSG00000163694 | 4 | RNA binding motif protein 47 [Source: HGNC Symbol; Acc: 30358] |
| RNPS1 | ENSG00000205937 | 16 | RNA binding protein S1, serine-rich domain [Source: HGNC Symbol; Acc: 10080] |
| SFRS1 | ENSG00000136450 | 17 | splicing factor, arginine/serine-rich 1 [Source: HGNC Symbol; Acc: 10780] |
| SFRS13B | ENSG00000154548 | 6 | splicing factor, arginine/serine-rich 13B [Source: HGNC Symbol; Acc: 21220] |
| SFRS7 | ENSG00000115875 | 2 | splicing factor, arginine/serine-rich 7, 35 kDa [Source: HGNC Symbol; Acc: 10789] |
| ZNF638 | ENSG00000075292 | 2 | zinc finger protein 638 [Source: HGNC Symbol; Acc: 17894] |
| RBM46 | ENSG00000151962 | 4 | RNA binding motif protein 46 [Source: HGNC Symbol; Acc: 28401] |
| AC008073.5 | ENSG00000115128 | 2 | Pre-mRNA branch site protein p14 (SF3b 14 kDa subunit) [Source: UniProtKB/Swiss-Prot; Acc: Q9Y384] |
| BRUNOL6 | ENSG00000140488 | 15 | CUGBP, Elav-like family member 6 [Source: HGNC Symbol; Acc: 14059] |
| CELF5 | ENSG00000161082 | 19 | CUGBP, Elav-like family member 5 [Source: HGNC Symbol; Acc: 14058] |
| CIRBP | ENSG00000099622 | 19 | cold inducible RNA binding protein [Source: HGNC Symbol; Acc: 1982] |
| CPEB3 | ENSG00000107864 | 10 | cytoplasmic polyadenylation element binding protein 3 [Source: HGNC Symbol; Acc: 21746] |
| CUGBP2 | ENSG00000048740 | 10 | CUGBP, Elav-like family member 2 [Source: HGNC Symbol; Acc: 2550] |
| DND1 | ENSG00000183403 | 5 | dead end homolog 1 (zebrafish) [Source: HGNC Symbol; Acc: 23799] |
| EIF4B | ENSG00000063046 | 12 | eukaryotic translation initiation factor 4B [Source: HGNC Symbol; Acc: 3285] |
| ESRP1 | ENSG00000104413 | 8 | epithelial splicing regulatory protein 1 [Source: HGNC Symbol; Acc: 25966] |
| HNRNPA1 | ENSG00000135486 | 12 | heterogeneous nuclear ribonucleoprotein A1-like 3 [Source: HGNC Symbol; Acc: 31015] |
| HNRNPF | ENSG00000169813 | 10 | heterogeneous nuclear ribonucleoprotein F [Source: HGNC Symbol; Acc: 5039] |
| HNRNPR | ENSG00000125944 | 1 | heterogeneous nuclear ribonucleoprotein R [Source: HGNC Symbol; Acc: 5047] |
| NCBP2 | ENSG00000114503 | 3 | nuclear cap binding protein subunit 2, 20 kDa [Source: HGNC Symbol; Acc: 7659] |
| PTBP1 | ENSG00000011304 | 19 | polypyrimidine tract binding protein 1 [Source: HGNC Symbol; Acc: 9583] |
| RAVER1 | ENSG00000161847 | 19 | rlbonucleoprotein, PTB-binding 1 [Source: HGNC Symbol; Acc: 30296] |
| RBM15B | ENSG00000179837 | 3 | RNA binding motif protein 15B [Source: HGNC Symbol; Acc: 24303] |
| RBM26 | ENSG00000139746 | 13 | RNA binding motif protein 26 [Source: HGNC Symbol; Acc: 20327] |
| RBM42 | ENSG00000126254 | 19 | RNA binding motif protein 42 [Source: HGNC Symbol; Acc: 28117] |
| RRP7A | ENSG00000189306 | 22 | ribosomal RNA processing 7 homolog B (S. cerevisiae) [Source: HGNC Symbol; Acc: 30454] |

TABLE 2-continued

| Symbol | Ensembl ID | Chr | Description |
|---|---|---|---|
| SF3B4 | ENSG00000143368 | 1 | splicing factor 3b, subunit 4, 49 kDa [Source: HGNC Symbol; Acc: 10771] |
| SFRS2 | ENSG00000161547 | 17 | splicing factor, arginine/serine-rich 2 [Source: HGNC Symbol; Acc: 10783] |
| SYNCRIP | ENSG00000135316 | 6 | synaptotagmin binding, cytoplasmic RNA interacting protein [Source: HGNC Symbol; Acc: 16918] |
| TRNAU1AP | ENSG00000180098 | 1 | tRNA selenocysteine 1 associated protein 1 [Source: HGNC Symbol; Acc: 30813] |
| TUT1 | ENSG00000149016 | 11 | terminal uridylyl transferase 1, U6 snRNA-specific [Source: HGNC Symbol; Acc: 26184] |
| U2AF1 | ENSG00000160201 | 21 | U2 small nuclear RNA auxiliary factor 1 [Source: HGNC Symbol; Acc: 12453] |
| U2AF2 | ENSG00000063244 | 19 | U2 small nuclear RNA auxiliary factor 2 [Source: HGNC Symbol; Acc: 23156] |
| NONO | ENSG00000147140 | X | non-POU domain containing, octamer-binding [Source: HGNC Symbol; Acc: 7871] |
| RBMY1F | ENSG00000169800 | Y | RNA binding motif protein, Y-linked, family 1, member F [Source: HGNC Symbol; Acc: 23974] |
| AC004381.6 | ENSG00000005189 | 16 | Putative RNA exonuclease NEF-sp (EC 3.1.—.—) [Source: UniProtKB/Swiss-Prot; Acc: Q96IC2] |
| C14orf156 | ENSG00000119705 | 14 | SRA stem-loop-interacting RNA-binding protein, mitochondrial Precursor [Source: UniProtKB/Swiss-Prot; Acc: Q9GZT3] |
| CPEB4 | ENSG00000113742 | 5 | cytoplasmic polyadenylation element binding protein 4 [Source: HGNC Symbol; Acc: 21747] |
| CSTF2T | ENSG00000177613 | 10 | cleavage stimulation factor, 3' pre-RNA, subunit 2, 64 kDa, tau variant [Source: HGNC Symbol; Acc: 17086] |
| DAZ4 | ENSG00000205916 | Y | deleted in azoospermia 4 [Source: HGNC Symbol; Acc: 15966] |
| EIF3G | ENSG00000130811 | 19 | eukaryotic translation initiation factor 3, subunit G [Source: HGNC Symbol; Acc: 3274] |
| ESRP2 | ENSG00000103067 | 16 | epithelial splicing regulatory protein 2 [Source: HGNC Symbol; Acc: 26152] |
| HNRNPA3 | ENSG00000170144 | 2 | heterogeneous nuclear ribonucleoprotein A3 [Source: HGNC Symbol; Acc: 24941] |
| HTATSF1 | ENSG00000102241 | X | HIV-1 Tat specific factor 1 [Source: HGNC Symbol; Acc: 5276] |
| PUF60 | ENSG00000179950 | 8 | poly-U binding splicing factor 60 KDa [Source: HGNC Symbol; Acc: 17042] |
| RBM33 | ENSG00000184863 | 7 | RNA binding motif protein 33 [Source: HGNC Symbol; Acc: 27223] |
| RDBP | ENSG00000204356 | 6 | Negative elongation factor E (NELF-E)(RNA-binding protein RD) [Source: UniProtKB/Swiss-Prot; Acc: P18615] |
| PTBP2 | ENSG00000117569 | 1 | polypyrimidine tract binding protein 2 [Source: HGNC Symbol; Acc: 17662] |
| G3BP2 | ENSG00000138757 | 4 | GTPase activating protein (SH3 domain) binding protein 2 [Source: HGNC Symbol; Acc: 30291] |
| HNRNPC | ENSG00000092199 | 14 | heterogeneous nuclear ribonucleoprotein C (C1/C2) [Source: HGNC Symbol; Acc: 5035] |
| RBMX | ENSG00000147274 | X | RNA binding motif protein, X-linked [Source: HGNC Symbol; Acc: 9910] |
| CPSF7 | ENSG00000149532 | 11 | cleavage and polyadenylation specific factor 7, 59 kDa [Source: HGNC Symbol; Acc: 30098] |
| RBM39 | ENSG00000131051 | 20 | RNA binding motif protein 39 [Source: HGNC Symbol; Acc: 15923] |
| SFRS11 | ENSG00000116754 | 1 | splicing factor, arginine/serine-rich 11 [Source: HGNC Symbol; Acc: 10782] |
| SFRS12 | ENSG00000153914 | 5 | splicing factor, arginine/serine-rich 12 [Source: HGNC Symbol; Acc: 17882] |
| SFRS4 | ENSG00000116350 | 1 | splicing factor, arginine/serine-rich 4 [Source: HGNC Symbol; Acc: 10786] |
| SFRS5 | ENSG00000100650 | 14 | splicing factor, arginine/serine-rich 5 [Source: HGNC Symbol; Acc: 10787] |
| RBM34 | ENSG00000188739 | 1 | RNA binding motif protein 34 [Source: HGNC Symbol; Acc: 28965] |
| TRA2A | ENSG00000164548 | 7 | transformer 2 alpha homolog (*Drosophila*) [Source: HGNC Symbol; Acc: 16645] |
| RBM7 | ENSG00000076053 | 11 | RNA binding motif protein 7 [Source: HGNC Symbol; Acc: 9904] |
| ZCRB1 | ENSG00000139168 | 12 | zinc finger CCHC-type and RNA binding motif 1 [Source: HGNC Symbol; Acc: 29620] |
| HNRNPA2B1 | ENSG00000122566 | 7 | heterogeneous nuclear ribonucleoprotein A2/B1 [Source: HGNC Symbol; Acc: 5033] |
| HNRNPD | ENSG00000138668 | 4 | heterogeneous nuclear ribonucleoprotein D (AU-rich element RNA binding protein 1, 37 kDa) [Source: HGNC Symbol; Acc: 50] |
| DNAJC17 | ENSG00000104129 | 15 | DnaJ (Hsp40) homolog, subfamily C, member 17 [Source: HGNC Symbol; Acc: 25556] |
| EIF4H | ENSG00000106682 | 7 | eukaryotic translation initiation factor 4H [Source: HGNC Symbol; Acc: 12741] |
| ENOX2 | ENSG00000165675 | X | ecto-NOX disulfide-thiol exchanger 2 [Source: HGNC Symbol; Acc: 2259] |
| HNRPLL | ENSG00000143889 | 2 | heterogeneous nuclear ribonucleoprotein L-like [Source: HGNC Symbol; Acc: 25127] |
| MKI67IP | ENSG00000155438 | 2 | MKI67 (FHA domain) interacting nucleolar phosphoprotein [Source: HGNC Symbol; Acc: 17838] |
| PABPC3 | ENSG00000151846 | 13 | poly(A) binding protein, cytoplasmic 3 [Source: HGNC Symbol; Acc: 8556] |
| POLDIP3 | ENSG00000100227 | 22 | polymerase (DNA-directed), delta interacting protein 3 [Source: HGNC Symbol; Acc: 23782] |
| PPIE | ENSG00000084072 | 1 | peptidylprolyl isomerase E (cyclophilin E) [Source: HGNC Symbol; Acc: 9258] |
| PPIL4 | ENSG00000131013 | 6 | peptidylprolyl isomerase (cyclophilin)-like 4 [Source: HGNC Symbol; Acc: 15702] |
| RBM10 | ENSG00000182872 | X | RNA binding motif protein 10 [Source: HGNC Symbol; Acc: 9896] |
| RBM12 | ENSG00000244462 | 20 | RNA binding motif protein 12 [Source: HGNC Symbol; Acc: 9898] |
| RBM16 | ENSG00000213079 | 6 | RNA binding motif protein 16 [Source: HGNC Symbol; Acc: 20959] |
| RBM17 | ENSG00000134453 | 10 | RNA binding motif protein 17 [Source: HGNC Symbol; Acc: 16944] |
| RBM19 | ENSG00000122965 | 12 | RNA binding motif protein 19 [Source: HGNC Symbol; Acc: 29098] |
| RBM22 | ENSG00000086589 | 5 | RNA binding motif protein 22 [Source: HGNC Symbol; Acc: 25503] |
| RBM23 | ENSG00000100461 | 14 | RNA binding motif protein 23 [Source: HGNC Symbol; Acc: 20155] |
| RBM45 | ENSG00000155636 | 2 | RNA binding motif protein 45 [Source: HGNC Symbol; Acc: 24468] |
| RBM8A | ENSG00000131795 | 1 | RNA binding motif protein 8A [Source: HGNC Symbol; Acc: 9905] |
| RBMY1A1 | ENSG00000234414 | Y | RNA binding motif protein, Y-linked, family 1, member C [Source: HGNC Symbol; Acc: 9914] |
| SFRS13A | ENSG00000188529 | 1 | splicing factor, arginine/serine-rich 13A [Source: HGNC Symbol; Acc: 16713] |
| SFRS6 | ENSG00000124193 | 20 | splicing factor, arginine/serine-rich 6 [Source: HGNC Symbol; Acc: 10788] |
| SNRNP35 | ENSG00000184209 | 12 | small nuclear ribonucleoprotein 35 kDa (U11/U12) [Source: HGNC Symbol; Acc: 30852] |
| ZRSR2 | ENSG00000169249 | X | zinc finger (CCCH type), RNA-binding motif and serine/argiinine rich 2 [Source: HGNC Symbol; Acc: 23019] |
| AC015631.1 | ENSG00000250177 | 4 | Polyadenylate-binding protein 4-like (Poly(A)-binding protein 4-like)(PABP-4-like) |
| AC021224.2 | ENSG00000215492 | 18 | Putative uncharacterized protein ENSP00000383298 [Source: UniProtKB/TrEMBL; Acc: C9JCD7] |
| AC021534.1 | ENSG00000167281 | 17 | Fox-1 homolog C [Source: UniProtKB/Swiss-Prot; Acc: A6NFN3] |
| AC021593.2 | ENSG00000078687 | 17 | Trinucleotide repeat-containing gene 6C protein [Source: UniProtKB/Swiss-Prot; Acc: Q9HCJ0] |
| AC027139.2 | ENSG00000215042 | 15 | |
| AC132219.2 | ENSG00000231942 | 8 | |
| CELF1 | ENSG00000149187 | 11 | CUGBP, Elav-like family member 1 [Source: HGNC Symbol; Acc: 2549] |
| CELF4 | ENSG00000101489 | 18 | CUGBP, Elav-like family member 4 [Source: HGNC Symbol; Acc: 14015] |
| CNOT4 | ENSG00000080802 | 7 | CCR4-NOT transcription complex, subunit 4 [Source: HGNC Symbol; Acc: 7880] |
| CPEB2 | ENSG00000137449 | 4 | cytoplasmic polyadenylation element binding protein 2 [Source: HGNC Symbol; Acc: 21745] |
| CSTF2 | ENSG00000101811 | X | cleavage stimulation factor, 3' pre-RNA, subunit 2, 64 kDa [Source: HGNC Symbol; Acc: 2484] |
| DAZL | ENSG00000092345 | 3 | deleted in azoospermia-like [Source: HGNC Symbol; Acc: 2685] |
| EIF3B | ENSG00000106263 | 7 | eukaryotic translation initiation factor 3, subunit B [Source: HGNC Symbol; Acc: 3280] |
| GRSF1 | ENSG00000132463 | 4 | G-rich RNA sequence binding factor 1 [Source: HGNC Symbol; Acc: 4610] |
| HNRNPA1L2 | ENSG00000139675 | 13 | heterogeneous nuclear ribonucleoprotein A1-like 2 [Source: HGNC Symbol; Acc: 27067] |

TABLE 2-continued

| | | | |
|---|---|---|---|
| HNRNPAB | ENSG00000197451 | 5 | heterogeneous nuclear ribonucleoprotein A/B [Source: HGNC Symbol; Acc: 5034] |
| HNRNPCL1 | ENSG00000179172 | 1 | heterogeneous nuclear ribonucleoprotein C-like 1 [Source: HGNC Symbol; Acc: 29295] |
| HNRNPH1 | ENSG00000169045 | 5 | heterogeneous nuclear ribonucleoprotein H1 (H) [Source: HGNC Symbol; Acc: 5041] |
| HNRNPH2 | ENSG00000126945 | X | heterogeneous nuclear ribonucleoprotein H2 (H') [Source: HGNC Symbol; Acc: 5042] |
| HNRNPH3 | ENSG00000096746 | 10 | heterogeneous nuclear ribonucleoprotein H3 (2H9) [Source: HGNC Symbol; Acc: 5043] |
| HNRNPL | ENSG00000104824 | 19 | heterogeneous nuclear ribonucleoprotein L [Source: HGNC Symbol; Acc: 5045] |
| IGF2BP1 | ENSG00000159217 | 17 | insulin-like growth factor 2 mRNA binding protein 1 [Source: HGNC Symbol; Acc: 28866] |
| LARP7 | ENSG00000174720 | 4 | La ribonucleoprotein domain family, member 7 [Source: HGNC Symbol; Acc: 24912] |
| MSI1 | ENSG00000135097 | 12 | musashi homolog 1 (*Drosophila*) [Source: HGNC Symbol; Acc: 7330] |
| MTHFSD | ENSG00000103248 | 16 | methenyltetrahydrofolate synthetase domain containing [Source: HGNC Symbol; Acc: 25778] |
| NCBP2L | ENSG00000170935 | X | nuclear cap binding protein subunit 2-like [Source: HGNC Symbol; Acc: 31795] |
| NCL | ENSG00000115053 | 2 | nucleolin [Source: HGNC Symbol; Acc: 7667] |
| NOL8 | ENSG00000198000 | 9 | nucleolar protein 8 [Source: HGNC Symbol; Acc: 23387] |
| PABPC1L | ENSG00000101104 | 20 | poly(A) binding protein, cytoplasmic 1-like [Source: HGNC Symbol; Acc: 15797] |
| PABPC1L2A | ENSG00000186288 | X | poly(A) binding protein, cytoplasmic 1-like 2A [Source: HGNC Symbol; Acc: 27989] |
| PABPC1L2B | ENSG00000184388 | X | poly(A) binding protein, cytoplasmic 1-like 2B [Source: HGNC Symbol; Acc: 31852] |
| PABPC4 | ENSG00000090621 | 1 | poly(A) binding protein, cytoplasmic 4 (inducible form) [Source: HGNC Symbol; Acc: 8557] |
| PABPN1 | ENSG00000100836 | 14 | poly(A) binding protein, nuclear 1 [Source: HGNC Symbol; Acc: 8565] |
| PABPN1L | ENSG00000205022 | 16 | poly(A) binding protein, nuclear 1-like (cytoplasmic) [Source: HGNC Symbol; Acc: 37237] |
| PPARGC1A | ENSG00000109819 | 4 | peroxisome proliferator-activated receptor gamma, coactivator 1 alpha [Source: HGNC Symbol; Acc: 9237] |
| PPARGC1B | ENSG00000155846 | 5 | peroxisome proliferator-activated receptor gamma, coactivator 1 beta [Source: HGNC Symbol; Acc: 30022] |
| PPRC1 | ENSG00000148840 | 10 | peroxisome proliferator-activated receptor gamma, coactivator-related 1 [Source: HGNC Symbol; Acc: 30025] |
| RALY | ENSG00000125970 | 20 | RNA binding protein, autoantigenic (hnRNP-associated with lethal yellow homolog (mouse)) |
| RAVER2 | ENSG00000162437 | 1 | ribonucleoprotein, PTB-binding 2 [Source: HGNC Symbol; Acc: 25577] |
| RBM18 | ENSG00000119446 | 9 | RNA binding motif protein 18 [Source: HGNC Symbol; Acc: 28413] |
| RBM24 | ENSG00000112183 | 6 | RNA binding motif protein 24 [Source: HGNC Symbol; Acc: 21539] |
| RBM25 | ENSG00000119707 | 14 | RNA binding motif protein 25 [Source: HGNC Symbol; Acc: 23244] |
| RBM27 | ENSG00000091009 | 5 | RNA binding motif protein 27 [Source: HGNC Symbol; Acc: 29243] |
| RBM38 | ENSG00000132819 | 20 | RNA binding motif protein 38 [Source: HGNC Symbol; Acc: 15818] |
| RBM44 | ENSG00000177483 | 2 | RNA binding motif protein 44 [Source: HGNC Symbol; Acc: 24756] |
| RBMS2P1 | ENSG00000213250 | 12 | RNA binding motif, single stranded interacting protein 2 pseudogene 1 [Source: HGNC Symbol; Acc: 30994] |
| RBMS3 | ENSG00000144642 | 3 | RNA binding motif, single stranded interacting protein 3 [Source: HGNC Symbol; Acc: 13427] |
| RBMX2 | ENSG00000134597 | X | RNA binding motif protein, X-linked 2 [Source: HGNC Symbol; Acc: 24282] |
| RBMXL1 | ENSG00000213516 | 1 | RNA binding motif protein, X-linked-like 1 [Source: HGNC Symbol; Acc: 25073] |
| RBMXL2 | ENSG00000170748 | 11 | RNA binding motif protein, X-linked-like 2 [Source: HGNC Symbol; Acc: 17886] |
| RBMXL3 | ENSG00000175718 | X | RNA binding motif protein, X-linked-like 3 [Source: HGNC Symbol; Acc: 26859] |
| RBMY1B | ENSG00000242875 | Y | RNA binding motif protein, Y-linked, family 1, member B [Source: HGNC Symbol; Acc: 23914] |
| RBMY1D | ENSG00000244395 | Y | RNA binding motif protein, Y-linked, family 1, member D [Source: HGNC Symbol; Acc: 23915] |
| RBMY1E | ENSG00000242389 | Y | RNA binding motif protein, Y-linked, family 1, member E [Source: HGNC Symbol; Acc: 23916] |
| RBMY1J | ENSG00000226941 | Y | RNA binding motif protein, Y-linked, family 1, member J [Source: HGNC Symbol; Acc: 23917] |
| RBPMS2 | ENSG00000166831 | 15 | RNA binding protein with multiple splicing 2 [Source: HGNC Symbol; Acc: 19098] |
| RNPC3 | ENSG00000185946 | 1 | RNA-binding region (RNP1, RRM) containing 3 [Source: HGNC Symbol; Acc: 18666] |
| RP11-658F2.1 | ENSG00000248643 | 11 | Transcriptional coactivator CoAZ [Source: UniProtKB/TrEMBL; Acc: B0LM41] |
| SAFB | ENSG00000160633 | 19 | scaffold attachment factor B [Source: HGNC Symbol; Acc: 10520] |
| SAFB2 | ENSG00000130254 | 19 | scaffold attachment factor B2 [Source: HGNC Symbol; Acc: 21605] |
| SART3 | ENSG00000075856 | 12 | squamous cell carcinoma antigen recognized by T cells 3 [Source: HGNC Symbol; Acc: 16860] |
| SETD1A | ENSG00000099381 | 16 | SET domain containing 1A [Source: HGNC Symbol; Acc: 29010] |
| SETD1B | ENSG00000139718 | 12 | SET domain containing 1B [Source: HGNC Symbol; Acc: 29187] |
| SFPQ | ENSG00000116560 | 1 | splicing factor proline/glutamine-rich [Source: HGNC Symbol; Acc: 10774] |
| SFRS15 | ENSG00000156304 | 21 | splicing factor, arginine/serine-rich 15 [Source: HGNC Symbol; Acc: 19304] |
| SFRS2B | ENSG00000180771 | 11 | splicing factor, arginine/serine-rich 2B [Source: HGNC Symbol; Acc: 16988] |
| SFRS3 | ENSG00000112081 | 6 | splicing factor, arginine/serine-rich 3 [Source: HGNC Symbol; Acc: 10785] |
| SFRS9 | ENSG00000111786 | 12 | splicing factor, arginine/serine-rich 9 [Source: HGNC Symbol; Acc: 10791] |
| SLTM | ENSG00000137776 | 15 | SAFB-like, transcription modulator [Source: HGNC Symbol; Acc: 20709] |
| SNRNP70 | ENSG00000104852 | 19 | small nuclear ribonucleoprotein 70 kDa (U1) [Source: HGNC Symbol; Acc: 11150] |
| SPEN | ENSG00000065526 | 1 | spen homolog, transcriptional regulator (*Drosophila*) [Source: HGNC Symbol; Acc: 17575] |
| SR140 | ENSG00000163714 | 3 | U2-associated protein SR140 (140 kDa Ser/Arg-rich domain protein) [Source: UniProtKB/Swiss-Prot; Acc: O15042] |
| SSB | ENSG00000138385 | 2 | Sjogren syndrome antigen B (autoantigen La) [Source: HGNC Symbol; Acc: 11316] |
| TAF15 | ENSG00000172660 | 17 | TAF15 RNA polymerase II, TATA box binding protein (TBP)-associated factor, 68 kDa [Source: HGNC Symbol; Acc: 11547] |
| TDRD10 | ENSG00000163239 | 1 | tudor domain containing 10 [Source: HGNC Syrnbol; Acc: 25316] |
| THOC4 | ENSG00000183684 | 17 | THO complex 4 [Source: HGNC Symbol; Acc: 19071] |
| TIAL1 | ENSG00000151923 | 10 | TIA1 cytotoxic granule-associated RNA binding protein-like 1 [Source: HGNC Symbol; Acc: 11804] |
| TNRC4 | ENSG00000159409 | 1 | CUGBP, Elav-like family member 3 [Source: HGNC Symbol; Acc: 11967] |
| TRA2B | ENSG00000136527 | 3 | transformer 2 beta homolog (*Drosophila*) [Source: HGNC Symbol; Acc: 10781] |
| UHMK1 | ENSG00000152332 | 1 | U2AF homology motif (UHM) kinase 1 [Source: HGNC Symbol; Acc: 19683] |
| ZRSR1 | ENSG00000212643 | 5 | zinc finger (CCCH type), RNA-binding motif and serine/arginine rich 1 [Source: HGNC Symbol; Acc: 12456] |

| Gene Name | Prion Domain Score | Prion Domain Rank | Prion Domain Rank Among RRM Proteins | Tested in Yeast Screen | Toxicity in Yeast Screen (1.4) | Localiztion in Yeast Screen |
|---|---|---|---|---|---|---|
| ELAVL1 | — | — | — | yes | 1 | cytoplasm, multiple foci |
| ELAVL2 | — | — | — | yes | 1 | cytoplasm, multiple foci |

TABLE 2-continued

| | | | | | | |
|---|---|---|---|---|---|---|
| ELAVL4 | — | — | — | yes | 1 | cytoplasm, multiple foci |
| HNRNPA0 | 20.6 | 81 | 16 | yes | 1 | cytoplasm, multiple foci |
| ROD1 | — | — | — | yes | 1 | cytoplasm, multiple foci |
| FUS | 37.6 | 13 | 1 | yes | 1.5 | cytoplasm, multiple foci |
| TARDBP | 26.5 | 43 | 10 | yes | 1.5 | cytoplasm, multiple foci |
| BOLL | — | — | — | yes | 2 | cytoplasm, multiple foci |
| DAZAP1 | 11.7 | 198 | 30 | yes | 2 | cytoplasm, multiple foci |
| G3BP1 | — | — | — | yes | 2 | cytoplasm, multiple foci |
| MSI2 | — | — | — | yes | 2 | cytoplasm, multiple foci |
| RBM14 | 16.1 | 117 | 18 | yes | 2 | cytoplasm, multiple foci |
| RBMS1 | — | — | — | yes | 2 | cytoplasm, multiple foci |
| RBMS2 | — | — | — | yes | 2 | cytoplasm, multiple foci |
| SNRPA | — | — | — | yes | 2 | cytoplasm, multiple foci |
| SNRPB2 | — | — | — | yes | 2 | cytoplasm, multiple foci |
| TIA1 | 23.2 | 55 | 11 | yes | 2 | cytoplasm, multiple foci |
| CPSF6 | — | — | — | yes | 2.5 | cytoplasm, multiple foci |
| DAZ1 | 14.1 | 143 | 23 | yes | 2.5 | cytoplasm, multiple foci |
| ELAVL3 | — | — | — | yes | 2.5 | cytoplasm, multiple foci |
| ENOX1 | — | — | — | yes | 2.5 | cytoplasm, multiple foci |
| IGF2BP2 | — | — | — | yes | 2.5 | cytoplasm, multiple foci |
| IGF2BP3 | — | — | — | yes | 2.5 | cytoplasm, multiple foci |
| RALYL | — | — | — | yes | 2.5 | cytoplasm, multiple foci |
| RBM41 | — | — | — | yes | 2.5 | cytoplasm, multiple foci |
| RBM4B | — | — | — | yes | 2.5 | cytoplasm, multiple foci |
| DAZ2 | 14.1 | 143 | 23 | yes | 3 | cytoplasm, multiple foci |
| HNRNPM | — | — | — | yes | 3 | cytoplasm, multiple foci |
| RBM4 | — | — | — | yes | 3 | cytoplasm, multiple foci |
| RBM5 | — | — | — | yes | 3 | cytoplasm, multiple foci |
| RBPMS | — | — | — | yes | 3 | cytoplasm, multiple foci |
| DAZ3 | 14.6 | 136 | 21 | yes | 3.5 | cytoplasm, multiple foci |
| EWSR1 | 32.4 | 25 | 3 | yes | 3.5 | cytoplasm, multiple foci |
| RBM12B | — | — | — | yes | 3.5 | cytoplasm, multiple foci |
| RBM9 | — | — | — | yes | 3.5 | cytoplasm, multiple foci |
| A1CF | — | — | — | yes | 4 | cytoplasm, multiple foci |
| AC005774.2 | — | — | — | yes | 4 | cytoplasm, multiple foci |
| HNRPDL | 31.5 | 28 | 4 | yes | 4 | cytoplasm, multiple foci |
| MYEF2 | — | — | — | yes | 4 | cytoplasm, multiple foci |
| PABPC1 | — | — | — | yes | 4 | cytoplasm, multiple foci |
| PABPC5 | — | — | — | yes | 4 | cytoplasm, multiple foci |
| PSPC1 | 10 | 226 | 31 | yes | 4 | cytoplasm, multiple foci |
| RBM11 | — | — | — | yes | 4 | cytoplasm, multiple foci |
| RBM15 | — | — | — | yes | 4 | cytoplasm, multiple foci |
| RBM28 | — | — | — | yes | 4 | cytoplasm, multiple foci |
| RBM3 | — | — | — | yes | 4 | cytoplasm, multiple foci |
| RBM47 | — | — | — | yes | 4 | cytoplasm, multiple foci |
| RNPS1 | — | — | — | yes | 4 | cytoplasm, multiple foci |
| SFRS1 | — | — | — | yes | 4 | cytoplasm, multiple foci |
| SFRS13B | — | — | — | yes | 4 | cytoplasm, multiple foci |
| SFRS7 | — | — | — | yes | 4 | cytoplasm, multiple foci |
| ZNF638 | — | — | — | yes | 4 | cytoplasm, multiple foci |
| RBM46 | — | — | — | yes | 3 | cytoplasm, diffuse |
| AC008073.5 | — | — | — | yes | 4 | cytoplasm, diffuse |
| BRUNOL6 | — | — | — | yes | 4 | cytoplasm, diffuse |
| CELF5 | — | — | — | yes | 4 | cytoplasm, diffuse |
| CIRBP | — | — | — | yes | 4 | cytoplasm, diffuse |
| CPEB3 | — | — | — | yes | 4 | cytoplasm, diffuse |
| CUGBP2 | — | — | — | yes | 4 | cytoplasm, diffuse |
| DND1 | — | — | — | yes | 4 | cytoplasm, diffuse |
| EIF4B | — | — | — | yes | 4 | cytoplasm, diffuse |
| ESRP1 | — | — | — | yes | 4 | cytoplasm, diffuse |
| HNRNPA1 | 28.2 | 38 | 7 | yes | 4 | cytoplasm, diffuse |
| HNRNPF | — | — | — | yes | 4 | cytoplasm, diffuse |
| HNRNPR | — | — | — | yes | 4 | cytoplasm, diffuse |
| NCBP2 | — | — | — | yes | 4 | cytoplasm, diffuse |
| PTBP1 | — | — | — | yes | 4 | cytoplasm, diffuse |
| RAVER1 | — | — | — | yes | 4 | cytoplasm, diffuse |
| RBM15B | — | — | — | yes | 4 | cytoplasm, diffuse |
| RBM26 | — | — | — | yes | 4 | cytoplasm, diffuse |
| RBM42 | — | — | — | yes | 4 | cytoplasm, diffuse |
| RRP7A | — | — | — | yes | 4 | cytoplasm, diffuse |
| SF384 | — | — | — | yes | 4 | cytoplasm, diffuse |
| SFRS2 | — | — | — | yes | 4 | cytoplasm, diffuse |
| SYNCRIP | — | — | — | yes | 4 | cytoplasm, diffuse |
| TRNAU1AP | — | — | — | yes | 4 | cytoplasm, diffuse |
| TUT1 | — | — | — | yes | 4 | cytoplasm, diffuse |
| U2AF1 | — | — | — | yes | 4 | cytoplasm, diffuse |
| U2AF2 | — | — | — | yes | 4 | cytoplasm, diffuse |
| NONO | — | — | — | yes | 4 | ER membrane |
| RBMY1F | — | — | — | yes | 3 | no expression |
| AC004381.6 | — | — | — | yes | 4 | no expression |

TABLE 2-continued

| | | | | | | |
|---|---|---|---|---|---|---|
| C14orf156 | — | — | — | yes | 4 | no expression |
| CPEB4 | — | — | — | yes | 4 | no expression |
| CSTF2T | 14 | 148 | 25.5 | yes | 4 | no expression |
| DAZ4 | 14.1 | 143 | 23 | yes | 4 | no expression |
| EIF3G | — | — | — | yes | 4 | no expression |
| ESRP2 | — | — | — | yes | 4 | no expression |
| HNRNPA3 | 27.2 | 41 | 9 | yes | 4 | no expression |
| HTATSF1 | — | — | — | yes | 4 | no expression |
| PUF60 | — | — | — | yes | 4 | no expression |
| RBM33 | 12.9 | 172 | 28 | yes | 4 | no expression |
| RDBP | — | — | — | yes | 4 | no expression |
| PTBP2 | — | — | — | yes | 1.5 | nucleus, multiple foci |
| G3BP2 | — | — | — | yes | 2 | nucleus, multiple foci |
| HNRNPC | — | — | — | yes | 2.5 | nucleus, multiple foci |
| RBMX | — | — | — | yes | 3 | nucleus, multiple foci |
| CPSF7 | — | — | — | yes | 4 | nucleus, multiple foci |
| RBM39 | — | — | — | yes | 4 | nucleus, multiple foci |
| SFRS11 | — | — | — | yes | 4 | nucleus, multiple foci |
| SFRS12 | — | — | — | yes | 4 | nucleus, multiple foci |
| SFRS4 | — | — | — | yes | 4 | nucleus, multiple foci |
| SFRS5 | — | — | — | yes | 4 | nucleus, multiple foci |
| RBM34 | — | — | — | yes | 1 | nucleus, diffuse |
| TRA2A | — | — | — | yes | 2 | nucleus, diffuse |
| RBM7 | — | — | — | yes | 3 | nucleus, diffuse |
| ZCRB1 | — | — | — | yes | 3 | nucleus, diffuse |
| HNRNPA2B1 | 29.9 | 32 | 6 | yes | 3.5 | nucleus, diffuse |
| HNRNPD | 30.6 | 30 | 5 | yes | 3.5 | nucleus, diffuse |
| DNAJC17 | — | — | — | yes | 4 | nucleus, diffuse |
| EIF4H | — | — | — | yes | 4 | nucleus, diffuse |
| ENOX2 | — | — | — | yes | 4 | nucleus, diffuse |
| HNRPLL | — | — | — | yes | 4 | nucleus, diffuse |
| MKI67IP | — | — | — | yes | 4 | nucleus, diffuse |
| PABPC3 | — | — | — | yes | 4 | nucleus, diffuse |
| POLDIP3 | — | — | — | yes | 4 | nucleus, diffuse |
| PPIE | — | — | — | yes | 4 | nucleus, diffuse |
| PPIL4 | — | — | — | yes | 4 | nucleus, diffuse |
| RBM10 | — | — | — | yes | 4 | nucleus, diffuse |
| RBM12 | — | — | — | yes | 4 | nucleus, diffuse |
| RBM16 | — | — | — | yes | 4 | nucleus, diffuse |
| RBM17 | — | — | — | yes | 4 | nucleus, diffuse |
| RBM19 | — | — | — | yes | 4 | nucleus, diffuse |
| RBM22 | — | — | — | yes | 4 | nucleus, diffuse |
| RBM23 | — | — | — | yes | 4 | nucleus, diffuse |
| RBM45 | — | — | — | yes | 4 | nucleus, diffuse |
| RBM8A | — | — | — | yes | 4 | nucleus, diffuse |
| RBMY1A1 | — | — | — | yes | 4 | nucleus, diffuse |
| SFRS13A | — | — | — | yes | 4 | nucleus, diffuse |
| SFRS6 | — | — | — | yes | 4 | nucleus, diffuse |
| SNRNP35 | — | — | — | yes | 4 | nucleus, diffuse |
| ZRSR2 | — | — | — | yes | 4 | nucleus, diffuse |
| AC015631.1 | — | — | — | no | NA | NA |
| AC021224.2 | 21.6 | 68 | 14 | no | NA | NA |
| AC021534.1 | — | — | — | no | NA | NA |
| AC021593.2 | 15.4 | 124 | 20 | no | NA | NA |
| AC027139.2 | — | — | — | no | NA | NA |
| AC132219.2 | — | — | — | no | NA | NA |
| CELF1 | — | — | — | no | NA | NA |
| CELF4 | 12.8 | 176 | 29 | no | NA | NA |
| CNOT4 | — | — | — | no | NA | NA |
| CPEB2 | — | — | — | no | NA | NA |
| CSTF2 | 15.7 | 122 | 19 | no | NA | NA |
| DAZL | — | — | — | no | NA | NA |
| EIF3B | — | — | — | no | NA | NA |
| GRSF1 | — | — | — | no | NA | NA |
| HNRNPA1L2 | 22.8 | 57 | 12 | no | NA | NA |
| HNRNPAB | 27.3 | 39 | 8 | no | NA | NA |
| HNRNPCL1 | — | — | — | no | NA | NA |
| HNRNPH1 | 22.3 | 63 | 13 | no | NA | NA |
| HNRNPH2 | 17.5 | 98 | 17 | no | NA | NA |
| HNRNPH3 | 14 | 147 | 25.5 | no | NA | NA |
| HNRNPL | — | — | — | no | NA | NA |
| IGF2BP1 | — | — | — | no | NA | NA |
| LARP7 | — | — | — | no | NA | NA |
| MSI1 | — | — | — | no | NA | NA |
| MTHFSD | — | — | — | no | NA | NA |
| NCBP2L | — | — | — | no | NA | NA |
| NCL | — | — | — | no | NA | NA |
| NOL8 | — | — | — | no | NA | NA |
| PABPC1L | — | — | — | no | NA | NA |
| PABPC1L2A | — | — | — | no | NA | NA |

TABLE 2-continued

| | | | | | | |
|---|---|---|---|---|---|---|
| PABPC1L2B | — | — | — | no | NA | NA |
| PABPC4 | — | — | — | no | NA | NA |
| PABPN1 | — | — | — | no | NA | NA |
| PABPN1L | — | — | — | no | NA | NA |
| PPARGC1A | — | — | — | no | NA | NA |
| PPARGC1B | — | — | — | no | NA | NA |
| PPRC1 | — | — | — | no | NA | NA |
| RALY | — | — | — | no | NA | NA |
| RAVER2 | — | — | — | no | NA | NA |
| RBM18 | — | — | — | no | NA | NA |
| RBM24 | — | — | — | no | NA | NA |
| RBM25 | — | — | — | no | NA | NA |
| RBM27 | — | — | — | no | NA | NA |
| RBM38 | — | — | — | no | NA | NA |
| RBM44 | — | — | — | no | NA | NA |
| RBMS2P1 | — | — | — | no | NA | NA |
| RBMS3 | — | — | — | no | NA | NA |
| RBMX2 | — | — | — | no | NA | NA |
| RBMXL1 | — | — | — | no | NA | NA |
| RBMXL2 | — | — | — | no | NA | NA |
| RBMXL3 | — | — | — | no | NA | NA |
| RBMY1B | — | — | — | no | NA | NA |
| RBMY1D | — | — | — | no | NA | NA |
| RBMY1E | — | — | — | no | NA | NA |
| RBMY1J | — | — | — | no | NA | NA |
| RBPMS2 | — | — | — | no | NA | NA |
| RNPC3 | — | — | — | no | NA | NA |
| RP11-658F2.1 | — | — | — | no | NA | NA |
| SAFB | — | — | — | no | NA | NA |
| SAFB2 | — | — | — | no | NA | NA |
| SART3 | — | — | — | no | NA | NA |
| SETD1A | — | — | — | no | NA | NA |
| SETD1B | — | — | — | no | NA | NA |
| SFPQ | 20.8 | 79 | 15 | no | NA | NA |
| SFRS15 | — | — | — | no | NA | NA |
| SFRS2B | — | — | — | no | NA | NA |
| SFRS3 | — | — | — | no | NA | NA |
| SFRS9 | — | — | — | no | NA | NA |
| SLTM | — | — | — | no | NA | NA |
| SNRNP70 | — | — | — | no | NA | NA |
| SPEN | — | — | — | no | NA | NA |
| SR140 | — | — | — | no | NA | NA |
| SSB | — | — | — | no | NA | NA |
| TAF15 | 33.2 | 22 | 2 | no | NA | NA |
| TDRD10 | — | — | — | no | NA | NA |
| THOC4 | — | — | — | no | NA | NA |
| TIAL1 | 13.5 | 158 | 27 | no | NA | NA |
| TNRC4 | — | — | — | no | NA | NA |
| TRA2B | — | — | — | no | NA | NA |
| UHMK1 | — | — | — | no | NA | NA |
| ZRSR1 | — | — | — | no | NA | NA |

A Table of all 213 human RRM proteins. 132 of these were tested for aggregation and toxicity in yeast.
Prion Domain scores and ranks are given for all RRM proteins.
Rank is out of all 21,873 human proteins.
Toxicity score: 1 = Very toxic, 4 = not toxic

TABLE 3

EWSR1 sequencing

| Chromosomic DNA NC_000022.10 | Genomic DNA NG_023240.1 | Coding DNA NM_001163285.1 | Predicted Protein NP_001156757.1 | [a]ALS Samples (n = 817) |
|---|---|---|---|---|
| g.29694840G > C | g.35843G > C | c.1532G > C | p.G511A | 1.22E-03 (1) |
| g.29695020C > A | g.36023C > A | NC | NC | 1.22E-03 (1) |
| g.29695132A > G | g.36135A > G | NC | NC | 1.22E-03 (1) |
| g.29695189A > G | g.36192A > G | NC | NC | 1.22E-03 (1) |
| g.29695301C > T | g.36304C > T | c.1655C > T | p.P552L | 1.22E-03 (1) |
| g.29695662C > T | g.36665C > T | c.1749C > T | NC | 1.22E-03 (1) |
| g.29695663G > A | g.36666G > A | c.1750G > A | p.G584S | 1.22E-03 (1) |
| g.29694847C > T | g.35850C > T | c.1539C > T | NC | 0 |
| g.29694892A > G | g.35895A > G | NC | NC | 0 |
| g.29694995C > T | g.35998C > T | NC | NC | 0 |
| g.29695032G > A | g.36035G > A | NC | NC | 0 |
| g.29695082A > G | g.36085A > G | NC | NC | 0 |
| g.29695737C > T | g.36740C > T | c.1824C > T | NC | 0 |

TABLE 3-continued

| | | | | | | |
|---|---|---|---|---|---|---|
| g.29695771C > G | g.36774C > G | c.1858C > G | NC | | 0 | |
| g.29695816C > T | g.36819C > T | c.1903C > T | p.R635C | | 0 | |

| Chromosomic DNA NC_000022.10 | [b]Sequenced Controls (n = 1082) | [c]SNP Controls (n = 4608) | ID | Dx | AAO. y | FH | Source |
|---|---|---|---|---|---|---|---|
| g.29694840G > C | 0 | 0 | ND10314 | ALS | 50 | Alzheimer | Coriell |
| g.29695020C > A | 0 | NA | ND10157 | ALS | 51 | No | Coriell |
| g.29695132A > G | 0 | NA | ND903-1 | ALS | 51 | No | CNDR |
| g.29695189A > G | 0 | NA | ND12124 | ALS | 48 | No | CNDR |
| g.29695301C > T | 0 | 0 | ND1038-1 | ALS | 36 | No | CNDR |
| g.29695662C > T | 0 | NA | ND745-1 | ALS | 71 | No | CNDR |
| g.29695663G > A | 0 | 2.17E−04 (1) | ND10828 | ALS | 51 | No | Coriell |
| g.29694847C > T | 9.24E−04 (1) | NA | CHOP1H11 | Healthy | NA | NA | CHOP |
| g.29694892A > G | 2.77E−03 (3) | NA | CHOP1G10 | Healthy | NA | NA | CHOP |
| | | | CHOP2E01 | Healthy | NA | NA | CHOP |
| | | | pl1G09 | Healthy | NA | NA | CNDR |
| g.29694995C > T | 9.24E−04 (1) | NA | ND02652 | Healthy | NA | NA | Coriell |
| g.29695032G > A | 9.24E−04 (1) | NA | ND09739 | Healthy | NA | NA | Coriell |
| g.29695082A > G | 9.24E−04 (1) | NA | CHOP2E05 | Healthy | NA | NA | CHOP |
| g.29695737C > T | 9.24E−04 (1) | NA | CHOP2B02 | Healthy | NA | NA | CHOP |
| g.29695771C > G | 9.24E−04 (1) | NA | ND07270 | Healthy | NA | NA | Coriell |
| g.29695816C > T | 9.24E−04 (1) | NA | ND10777 | Healthy | NA | NA | Coriell |

TAF15 sequencing

| Chromosomic DNA NC_000017.10 | Genomic DNA NG_023279.1 | Coding DNA NM_139215.1 | Predicted Protein NP_631961.1 | [a]ALS Samples (n = 610) | [b]Sequenced Controls (n = 982) |
|---|---|---|---|---|---|
| g.34171358G > A | g.39871G > A | c.1163G > A | p.R388H | 6.56E−03 (4) | 1.02E−03 (1) |
| g.34171367G > A | g.39880G > A | c.1172G > A | p.G391E | 1.64E−03 (1) | 0 |
| g.34171525C > T | g.40038C > T | c.1222C > T | p.R408C | 1.64E−03 (1) | 0 |
| g.34171635C > T | g.40148C > T | c.1332C > T | NC | 1.64E−03 (1) | 0 |
| g.34171749T > C | g.40262T > C | c.1446T > C | NC | 1.64E−03 (1) | 0 |
| g.34171212T > A | g.39725T > A | NC | NC | 0 | 1.02E−03 (1) |
| g.34171216G > A | g.39729G > A | NC | NC | 0 | 1.02E−03 (1) |

| Chromosomic DNA NC_000017.10 | [c]SNP Controls (n = 4608) | ID | Dx | AAO. y | FH | Source |
|---|---|---|---|---|---|---|
| g.34171358G > A | NA | 1995-164 | ALS | NA | NA | CNDR |
| | | 2001-163 | ALS | NA | NA | CNDR |
| | | 2007-029 | ALS | 54 | NA | CNDR |
| | | ND08531 | ALS | 47 | No | Coriell |
| g.34171367G > A | 0 | ND989-1 | ALS | NA | Other ND | CNDR |
| g.34171525C > T | 0 | 2008-162 | ALS | NA | NA | CNDR |
| g.34171635C > T | NA | 2007-127 | ALS | 69 | NA | CNDR |
| g.34171749T > C | NA | ND634-1 | ALS | 57 | Other ND | CNDR |
| g.34171212T > A | NA | ND01658 | Healthy | NA | NA | Coriell |
| g.34171216G > A | NA | CHOP1B06 | Healthy | NA | NA | CHOP |

Abbreviations:
AAO, age at onset;
ALS, amyotrophic lateral sclerosis;
Dx, diagnosis;
FH, family history;
ID, identifier;
NA, not available;
NC, no change.
[a]Frequency in 817 ALS cases for EWSR1 or 610 for TAF15; numbers in parentheses indicate counts.
[b]Frequency in our 1,082 sequenced control cases for EWSR1 and 982 for TAF15; numbers in parentheses indicate counts.
[c]Frequency in our 4,608 SNP genotyped control cases; numbers in parentheses indicate counts. Note that for EWSR1, we identified variant G584S once in an ALS case and once in a SNP genotyped control.
R388H four times in ALS cases and once in sequenced controls. The other missense variants (G511A and P552L for EWSR1; G391E and R408C for TAF15) were not present in the controls (5,690 for EWSR1 and 5,590 for TAF15) nor in publicly available SNP databases.

To focus this list further, we used a bioinformatics approach. In addition to the RRM domain, FUS and TDP-43 share a glycine-rich domain and a bioinformatics-predicted prion-like domain (Cushman et al., 2010). Like prion domains found in fungal prion proteins (e.g. Sup35, Ure2, and Rnq1), these domains are enriched in uncharged polar amino acids (such as asparagine, glutamine and tyrosine) and glycine (Alberti et al., 2009). In TDP-43, the predicted prion domain overlaps the glycine-rich domain; in FUS, a QQSY-rich region defines the prion domain, although there is some overlap with the glycine rich domain. The prion domain is a shared feature that may be important, given the prion-like aggregation propensity of many proteins associated with human neurodegenerative disease (Aguzzi and Rajendran, 2009). Remarkably, using an algorithm to score 21,873 human proteins for likelihood of harboring a prion domain, FUS and TDP-43 ranked 13th and 43rd, respectively. We therefore interrogated the list of human RRM proteins to identify whether others ranked highly using the prion domain prediction algorithm (Alberti et al., 2009). Interestingly, 31 of the 213 human RRM proteins ranked in the top 250 (Table 2). Among these, FUS and TDP-43 ranked $1^{st}$ and $10^{th}$, respectively. Of the 35 proteins that were toxic and formed cytoplasmic inclusions in the cytoplasm in yeast, 10, including FUS and TDP-43, scored highly for a prion-like domain (Table 1). Thus, using the combined yeast screen and prion-like domain analysis, we narrowed the list of RRM proteins by 13-fold (132 human RRM proteins→35 that aggregate and are toxic in yeast→10 that also contain prion domain). Further, that of human RRM proteins, FUS ranks #1 and TDP-43 ranks #10, indicated that the other human RRM proteins with prion domains ranked #2-9 should be a top priority for analysis. We therefore focused on these proteins because they shared similar functional and structural features with FUS and TDP-43: 1) formed cytoplasmic accumulations, 2) were toxic in yeast, and 3) contained a predicted prion-like domain.

Figure 2A:
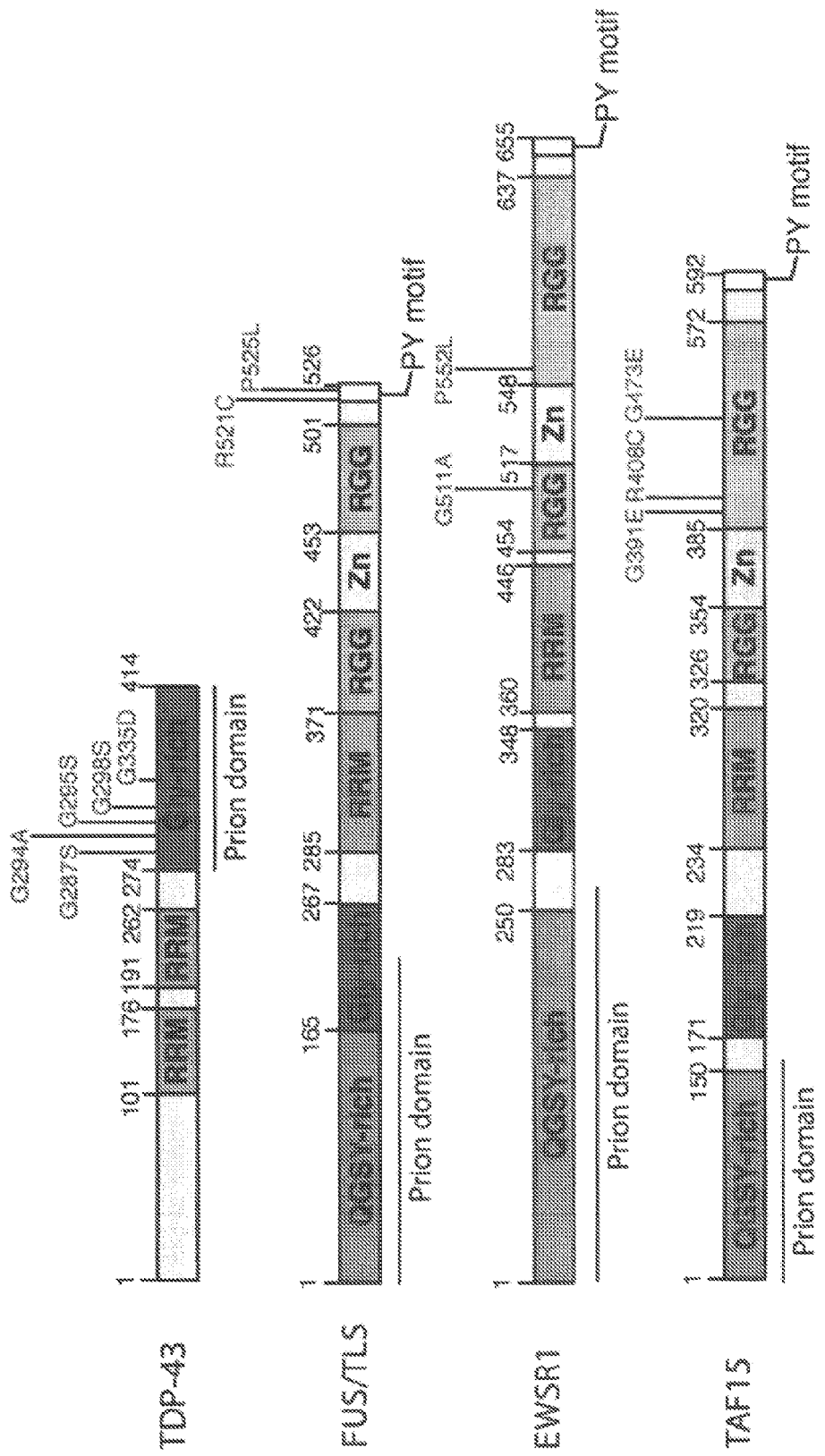
FIG. 2. Missense mutations in EWSR1 and TAF15 in ALS patients. (a) Comparison of FUS, EWSR1, and TAF15 demonstrates similar domain architecture. All three proteins contain a single RRM, a glycine-rich domain, a predicted prion-domain, RGG domains, and a C-terminal PY-motif, which can function as an NLS (Dormann et al., 2010). Mutations in FUS and TDP-43 are selected examples of those similar to variants found in EWSR1 and TAF15. (b,c) DNA sequence analysis of EWSR1 in ALS patients identified 2 missense mutations (shown are electropherograms highlighting the sequence variants). (b) A single base substitution (asterisk; SEQ ID NO: 5) changing the wild-type guanine at 1532 to cytosine (c.1532 G>C), alanine substituting for glycine (p.G511A). (c) Another mutation in an ALS case: c.1655 C>T (SEQ ID NO: 6), leucine substituted for proline (p.P552L). (d) Sequence alignment of amino acids 505 to 564 of EWSR1 from diverse vertebrate species indicates that the mutated residues in EWSR1 are highly conserved. Identical amino acids have a black background, similar amino acids are gray, and mutation sites are red. (Human, mouse, opossum: SEQ ID NO: 7; dog: SEQ ID NO: 8; frog: SEQ ID NO: 9; zebrafish: SEQ ID NO: 10) (e-f) DNA sequence analysis of TAF15 in ALS patients identified 3 missense mutations. (e) A TAF15 mutation in an ALS case: c.1172 G>A, (SEQ ID NO: 11), glutamic acid substituted for glycine (p.G391E). (f) Another TAF15 mutation in an ALS case: c.1222 C>T, (SEQ ID NO: 12) histidine substituted for arginine (p.R408C). An additional TAF15 variant (c.1418G>A, p.Gly473Glu), identified in the ALS cohort from Mayo Clinic is shown in a. (g) Sequence alignment of amino acids 358 to 416 of TAF15 from diverse vertebrate species indicates that the mutated residues in TAF15 are highly conserved. Identical amino acids have a black background, similar amino acids are gray, and mutation sites are red. (Human, mouse, dog: SEQ ID NO: 13; chicken: SEQ ID NO: 14; frog: SEQ ID NO: 15)
Figure 2:
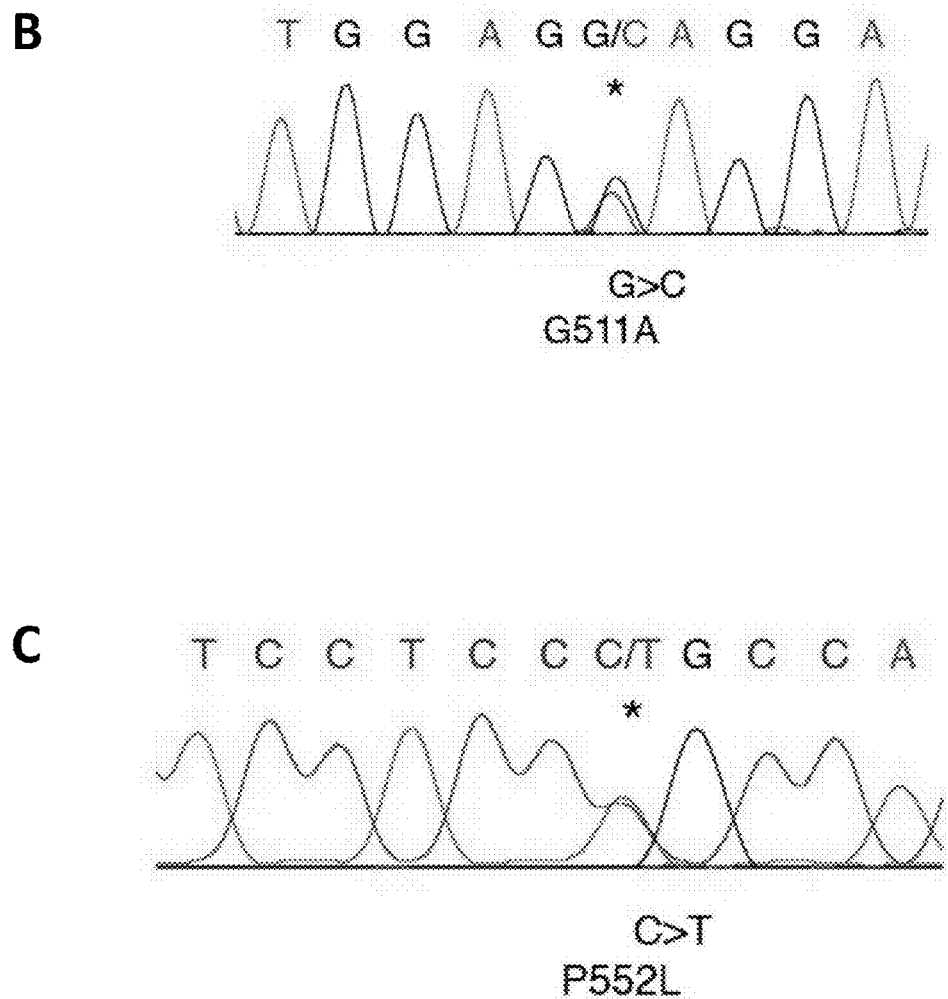
Figure 2:
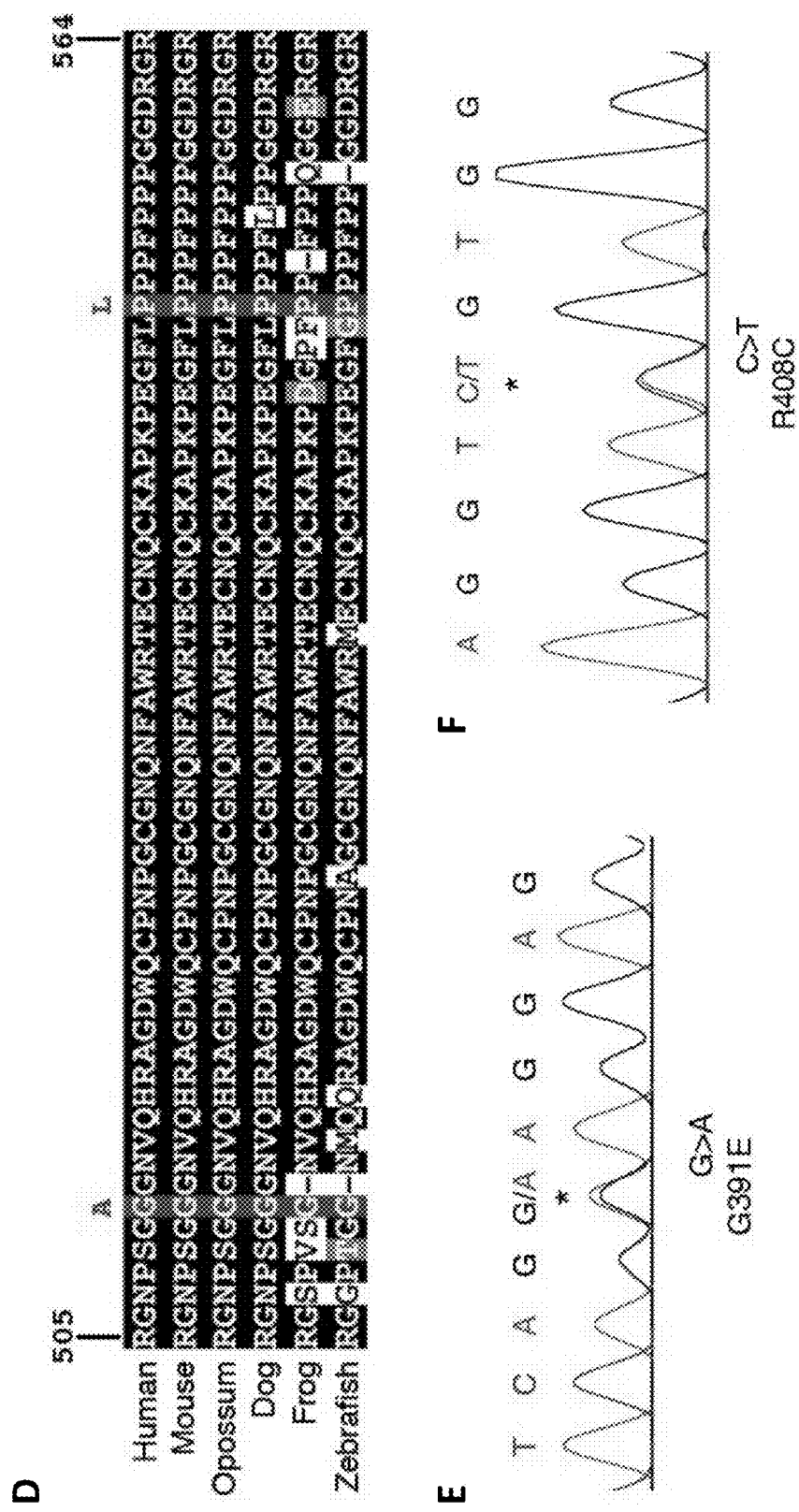

With this list of ten "FUS- and TDP-43-like" proteins in hand, we sought to test the hypothesis that these additional RRM proteins might contribute to ALS. One of these proteins, EWSR1 (Ewing sarcoma breakpoint region 1), in addition to being a homologue of FUS, revealed a localization pattern in yeast remarkably similar to that of TDP-43 and FUS (FIG. 1c). Spotting assays showed that EWSR1 expression was also toxic, albeit not as toxic as TDP-43 and FUS (FIG. 1d). Using the prion domain prediction algorithm, EWSR1 ranked $25^{th}$ out of 21,873 human proteins and $3^{rd}$ out of 213 human RRM proteins (Table 1). Furthermore, EWSR1 contains notably similar domain architecture to FUS: like FUS, EWSR1 contains a single RRM, a glycine-rich region, an N-terminal prion domain, RGG domains, and a C-terminal PY-motif (FIG. 2a). Given these striking commonalities in structure, predicted prion domain, and behavior in yeast, we sought to identify EWSR1 mutations in ALS patients.

Figure 2G:
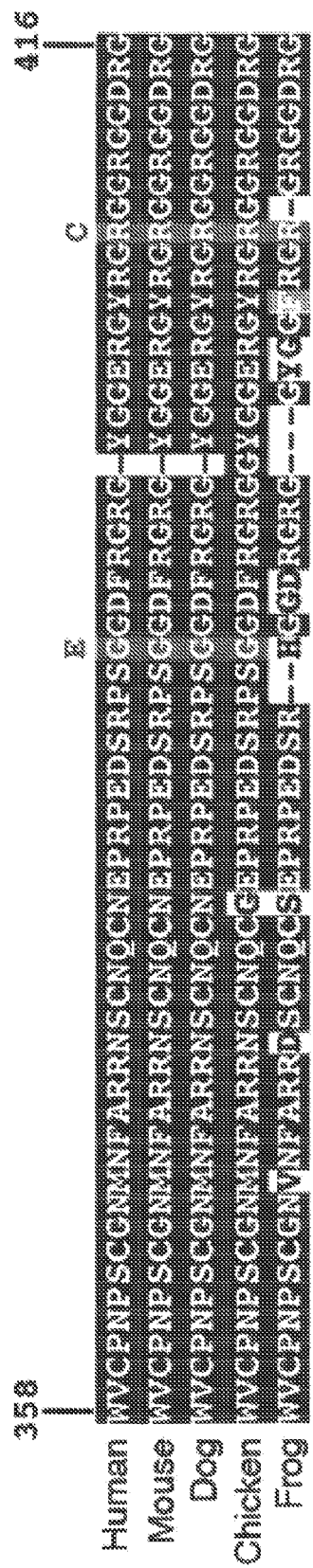

Since almost all known pathogenic mutations in FUS and TDP-43 are located in the C-terminal domains of the proteins (Lagier-Tourenne and Cleveland, 2009), we focused on the last four exons of the EWSR1 gene (exons 15-18; NM_001163285). These exons comprise the RGG- and PY-motif-containing C-terminal domain, which are important for nuclear localization of FUS and EWSR1 (Araya et al., 2003; Dormann et al., 2010; Shaw et al., 2009; Zakaryan and Gehring, 2006). Complete sequencing of these exons was performed in 817 individuals diagnosed with ALS (see Methods for patient and control demographic information) and in 1,082 geographically-matched healthy population control individuals (see Methods for details). We followed up this analysis with Taqman SNP genotyping of any patient-specific mutations in 4,608 healthy individuals (Table 3). This approach identified two patient specific missense variants in EWSR1 in two unrelated ALS patients with sporadic disease (FIG. 2b-d, Table 3). Missense variants were identified in exon 16 (c.1532G>C, p.Gly511Ala) and exon 17 (c.1655C>T, p.Pro522Leu). These individuals had disease onset of 50 years and 36 years, respectively. Neither of these were present in 1,082 sequenced controls nor in the 4,608 targeted SNP genotyped controls, strongly supporting clinical significance of these variants. Overall, these specific genetic variants in EWSR1 were detected in 2 out of 817 ALS cases and 0 out of 5,690 controls (P=0.015). Furthermore, none of these variants were present in public SNP databases (e.g. dbSNP), eight HapMAP individuals sequenced (Ng et al., 2009b), or the 1000 Genomes Project (http://browser.1000genomes.org/index.html). Notably, the two variants are located in highly conserved regions of EWSR1 (FIG. 2d). Since the EWSR1 variants were identified in sporadic ALS cases, familial evidence for segregation with disease was not possible; however TARDBP and FUS mutations have also been confirmed in apparent sporadic ALS cases (Lagier-Tourenne et al., 2010). In addition, the parents of the affected individuals were not available to determine if the mutations occurred de novo or were inherited. Because the yeast expression library of RRM proteins did not contain every human RRM protein, we analyzed additional proteins that were not included in the yeast screen for features similar to TDP-43, FUS, and EWSR1. We gave top priority to TAF15 (RNA polymerase II, TATA box binding protein (TBP)-associated factor, 68 kDa) because it belongs to the same protein family as FUS and EWSR1 (TET family) and is remarkably similar to those two proteins, especially within the RRM, glycine-rich domain, and C-terminal RGG domain- and PY-motif-containing region (FIG. 2a). Curiously, all three genes have been implicated in chromosomal translocations in cancer (Tan and Manley, 2009). Like FUS and EWSR1, TAF15 ranks very high using the prion domain prediction algorithm (ranked $2^{nd}$ out of 213 human RRM proteins). Given these commonalities, we proceeded to sequence exons 13-16 of TAF15 (NM_139215), which encode the C-terminal region analogous to where we found EWSR1 variants and to where many FUS mutations are located. We performed complete sequencing of these exons in 610 individuals diagnosed with ALS (see Methods for patient and control demographic information) and in 982 geographically-matched healthy population control individuals. This analysis was followed up by Taqman SNP genotyping of patient specific mutations in 4,608 healthy individuals (Table 3). In TAF15, we found two patient-specific missense variants (FIG. 2e-g, Table 3), one in exon 14 (c.1172G>A, p.Gly391Glu) and the other in exon 15 (c.1222C>T, p.Arg408Cys). These variants were found in individuals with ages of onset of sporadic ALS of 67 years and 47 years, respectively. As for EWSR1, the TAF15 variants were not found in the large cohort of control individuals (982 control individuals sequenced and 4,608 analyzed by targeted SNP genotyping). Familial segregation studies were not possible. Overall, these specific missense variants in TAF15 were detected in 2 out of 610 ALS cases and 0 out of 5,590 population controls (P=0.01).

In the process of sequencing these genes in ALS cases and controls, we also identified several synonomous and noncoding variants as summarized in Table 3. In addition, we identified two missense variants that were present in both patients and controls (EWSR1 c. 1750G>A, p.G584S and TAF15 c.1163G>A, p.R388H) as well as one variant present only in a single control (EWSR1 c.1903C>T, p.R635C). The presence of these variants in control individuals suggests that these likely represent rare benign variants, although these studies alone cannot not exclude the possibility that they represent disease variants with reduced penetrance. In contrast, the four patient-specific variants in EWSR1 (G511A and P552L) and TAF15 (G391E and R408C) were not found in >5,000 healthy controls, and together with the functional evidence below, strongly suggests that these are disease-specific mutations. Finally, we also analyzed EWSR1 and TAF15 in an independent ALS cohort from the Mayo Clinic. We screened 125 ALS patients and identified one missense variant in TAF15 (c.1418G>A, p.Gly473Glu) in an individual with age of onset of 68. This variant was not present in the 982 sequenced controls or in an additional 904 SNP-genotyped controls. Thus, taken together, we identified 2 missense variants in EWSR1 and 3 missense variants in TAF15 (FIG. 2a) in ALS patients that were not present in a very large number of healthy controls.

Although these studies highlight a potential role for EWSR1 and TAF15 in ALS pathogenesis, we next sought functional evidence that these proteins have properties similar to TDP-43 and FUS. First, do EWSR1 and TAF15 spontaneously aggregate in vitro as do TDP-43 and FUS (Johnson et al., 2009; Li et al., 2010b)? Second, do these proteins confer neurodegeneration when expressed in the nervous system, as for TDP-43 (Elden et al., 2010; Hanson et al., 2010; Li et al., 2010a; Lu et al., 2009; Ritson et al., 2010)? Third, can the ALS-associated variants in EWSR1 and TAF15 perturb protein localization in neurons, as for some ALS-linked TDP-43 and FUS mutations (Barmada et al., 2010; Dormann et al., 2010; Kabashi et al., 2010; Kwiatkowski et al., 2009; Vance et al., 2009)?

Figure 3:
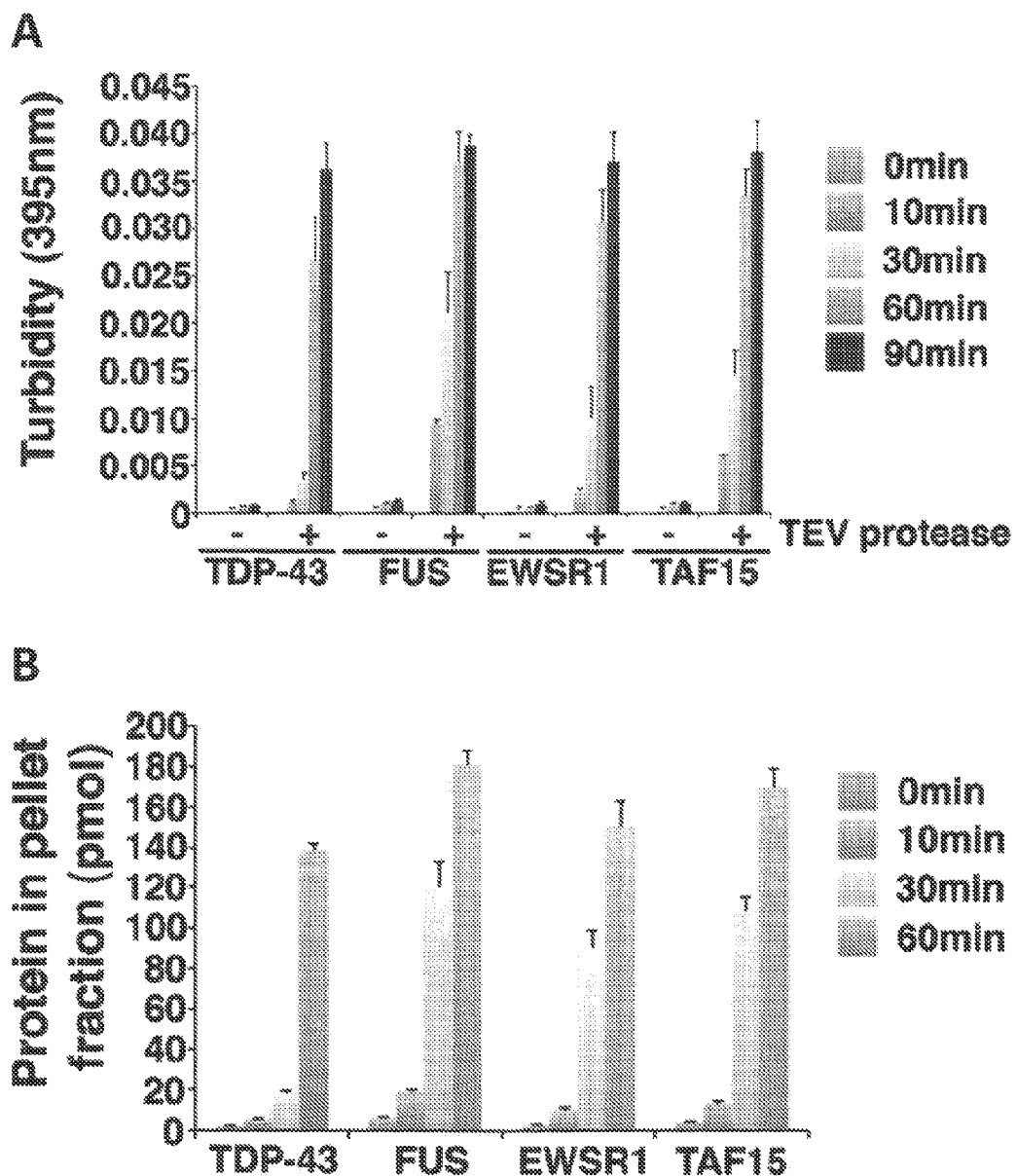
FIG. 3. EWSR1 and TAF15 are aggregation-prone proteins. a) GST-TDP-43, GST-FUS, GST-EWSR-1 or GST-TAF15 (3 μM) were incubated in the presence or absence of TEV protease at 25° C. for 0-90 min with agitation. Note that very little aggregation occurs in the absence of TEV protease. The extent of aggregation was determined by turbidity. Values represent means±SEM (n=3). b) GST-TDP-43, GST-FUS, GST-EWSR1 or GST-TAF15 (3 μM) were incubated in the presence of TEV protease at 25° C. for 0-60 min. At the indicated times, reactions were processed for sedimentation analysis. Pellet and supernatant fractions were resolved by SDS-PAGE and stained with Coomassie Brilliant Blue. The amount of protein in the pellet fraction was determined by densitometry in comparison to known quantities of the appropriate protein. Values represent means±SEM (n=3). A human RRM protein, DND1, which did not aggregate and was not toxic in yeast (FIG. 1 c,d), was also soluble and did not form aggregates in this assay (data not shown). c) GST-TDP-43, GST-FUS, GST-EWSR-1 or GST-TAF15 (3 μM) were incubated in the presence of TEV protease at 25° C. for 0-60 min. At various times, reactions were processed for EM. Small arrows denote small pore-shaped oligomers and large arrows denote linear polymers. Bar, 500 nm. d) Gallery of TDP-43, FUS, EWSR1 and TAF15 oligomers formed during aggregation reactions. Bar, 50 nm.
Figure 3:
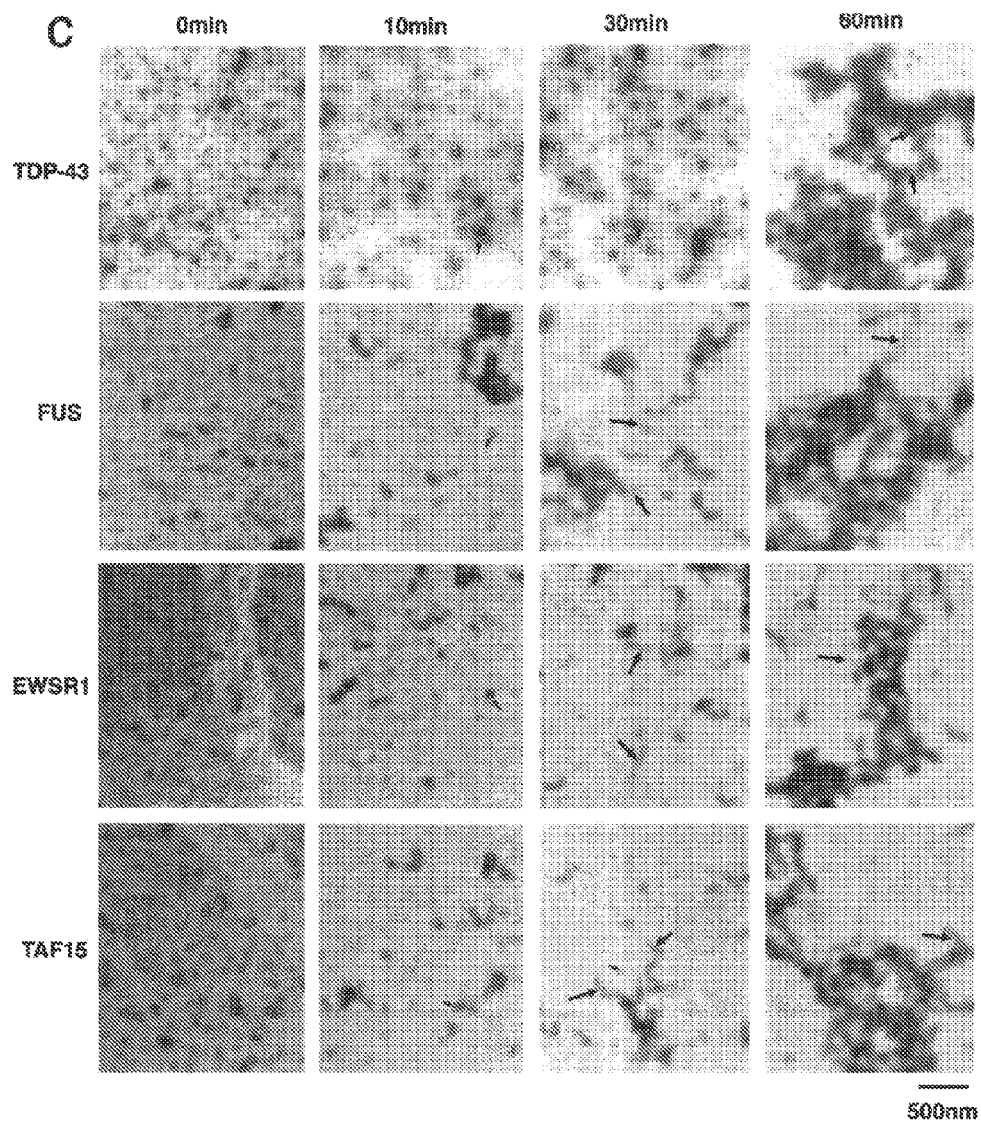
Figure 3D:
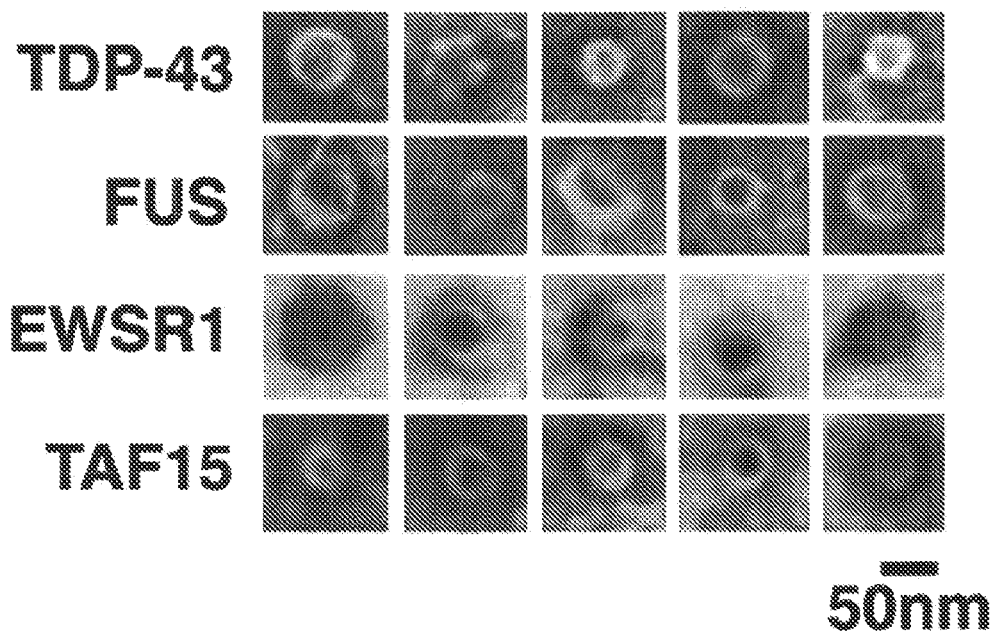

Bacterially expressed glutathione S-transferase (GST) tagged EWSR1 and TAF15 were purified as soluble proteins under native conditions, as previously done for TDP-43 and FUS (Johnson et al., 2009; Sun et al., 2010). Upon addition of Tobacco Etch Virus (TEV) protease to specifically remove the N-terminal GST tag EWSR1 and TAF15 rapidly aggregated at 25° C. with gentle agitation. The proteins aggregated with kinetics similar to FUS and slightly more rapidly than TDP-43, assessed by turbidity (FIG. 3a) and the amount that entered the pellet fraction after centrifugation (FIG. 3B). If TEV protease was omitted, then little aggregation occurred (FIG. 3a, b). Electron microscopy revealed that EWSR1 and TAF15 rapidly accessed oligomeric forms (FIG. 3c), which would frequently adopt a pore-like conformation (FIG. 3c, small arrows; 3d), similar to those formed by TDP-43 and FUS (FIG. 3c, d) (Johnson et al., 2009; Sun et al., 2010). Furthermore, EWSR1 and TAF15 also assembled into linear polymers with a cross-sectional diameter of ~15-20 nm (FIG. 3c, large arrows) that increased in length over time and would often become tangled into large masses by 60 min (FIG. 3c). In general, the morphology of EWSR1 and TAF15 aggregates were more similar to FUS than to TDP-43, which over this time frame formed shorter polymers that would clump together to form large masses (FIG. 3c) (Johnson et al., 2009). Importantly, a human RRM protein, DND1, which did not aggregate and was not toxic in yeast (FIG. 1c, d) also remained soluble and did not aggregate in this in vitro assay (data not shown), providing evidence that in vitro aggregation is not a property shared by all RRM proteins. Thus, similar to TDP-43 and FUS, and concordant with the yeast data, EWSR1 and TAF15 are inherently aggregation-prone proteins.

Figure 4:
FIG. 4. EWSR1 and TAF15 confer neurodegeneration in Drosophila. (a-c) EWSR1 and TAF15 cause neural degeneration and dysfunction in Drosophila. a) Toxicity of various human RRM proteins in the eye. EWSR1 and TAF15 cause degeneration and disruption of the retinal structure, akin to TDP-43 (also see (Elden et al., 2010)). Control is driver line alone gmr-GAL4/+. TDP-43 is gmr-GAL4/UAS-TDP-43-YFP. EWSR1 is gmr-GAL4/UAS-EWSR1. TAF15 is gmr-GAL4/UAS-TAF15 (grown at 29° C.). b,c) Progressive loss of climbing behavior upon expression of TDP-43, EWSR1 and TAF15 in the nervous system (elav, b) or selectively in motor neurons (D42, c). d) Upregulation of other RRM proteins does not cause neurodegeneration in Drosophila. As a specificity control for the neurodegenerative phenotype conferred by upregulation of TDP-43, EWSR1, and TAF15 in Drosophila (see FIG. 4a), we tested the effects of upregulating the fly counterparts of two other human RRM proteins in the eye using the GAL4-UAS system. The human homologues fail to aggregate or confer toxicity in yeast—neither fly counterpart conferred neurodegeneration in Drosophila.
Figure 4:
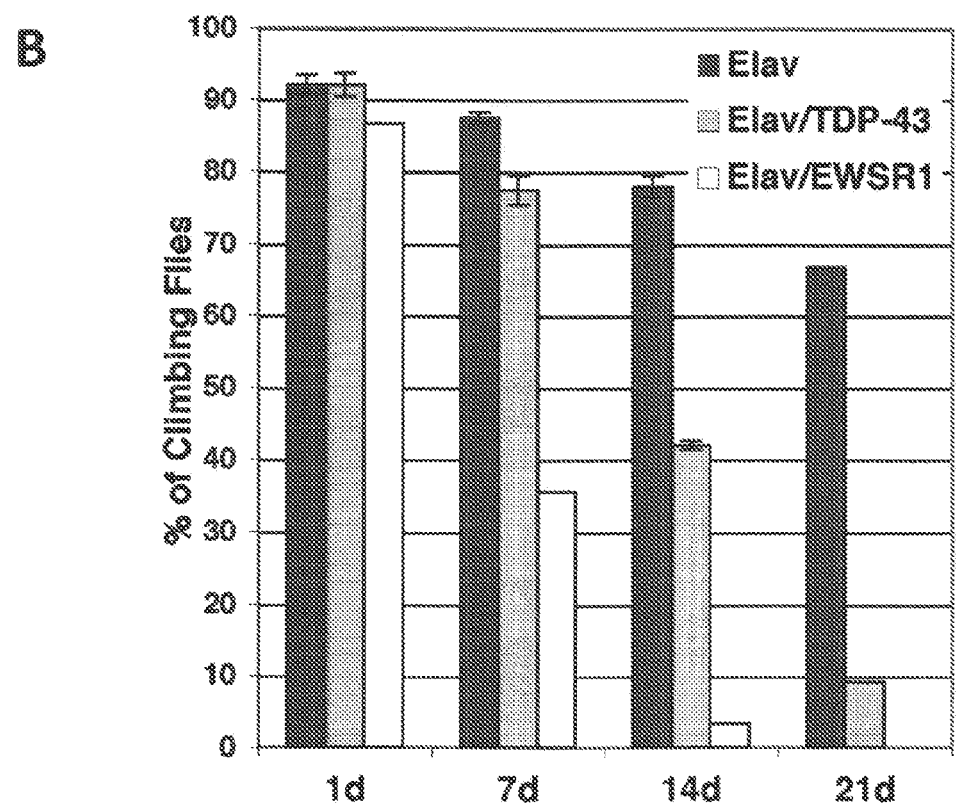
Figure 4:
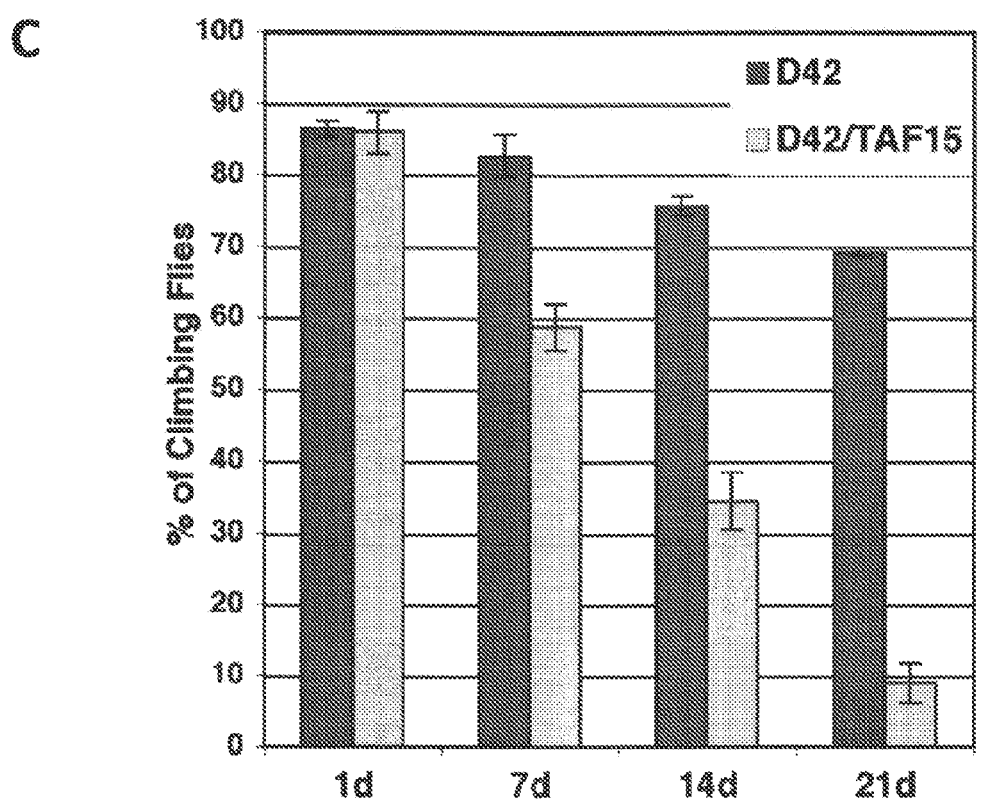

To analyze the effects of these proteins in the nervous system, we used Drosophila. We and others have previously shown that directing TDP-43 expression to the fly nervous system causes neurodegeneration (Elden et al., 2010; Hanson et al., 2010; Li et al., 2010a; Lu et al., 2009; Ritson et al., 2010). A series of transgenic lines were generated that expressed wild type (WT) human EWSR1 and TAF15. Directing expression of these proteins to the eye of the fly caused degeneration of the structure (FIG. 4a) and led to progressive loss of motility when directed to motor neurons (FIG. 4b). As for the in vitro aggregation assay, the effect was specific because two other unrelated RRM proteins, the human counterparts of which did not aggregate and are not toxic in yeast, did not confer neurodegeneration when upregulated in Drosophila (FIG. 4d). Thus, EWSR1 and TAF15 possess activity sufficient to confer neurodegeneration in the nervous system, in a manner similar to that of TDP-43. Importantly, these experiments do not indicate per se that these molecules cause disease. Rather, they provide evidence that they have similar properties as the known ALS disease-causing genes TDP-43 and FUS.

The preceding experiments provide evidence that the wild type versions of EWSR1 and TAF15 have similar properties as TDP-43 and FUS; they aggregate in vitro, confer toxicity in yeast and neurodegeneration in Drosophila. This aggregation and toxicity in yeast and flies that we observe with the WT protein may or may not be directly disease-related; the key point is that, in addition to sharing similar structural features to TDP-43 and FUS, EWSR1 and TAF15 also share similar functional features. To provide evidence that these variants might be pathogenic, we next asked if and how they affected the protein.

Figure 5A:
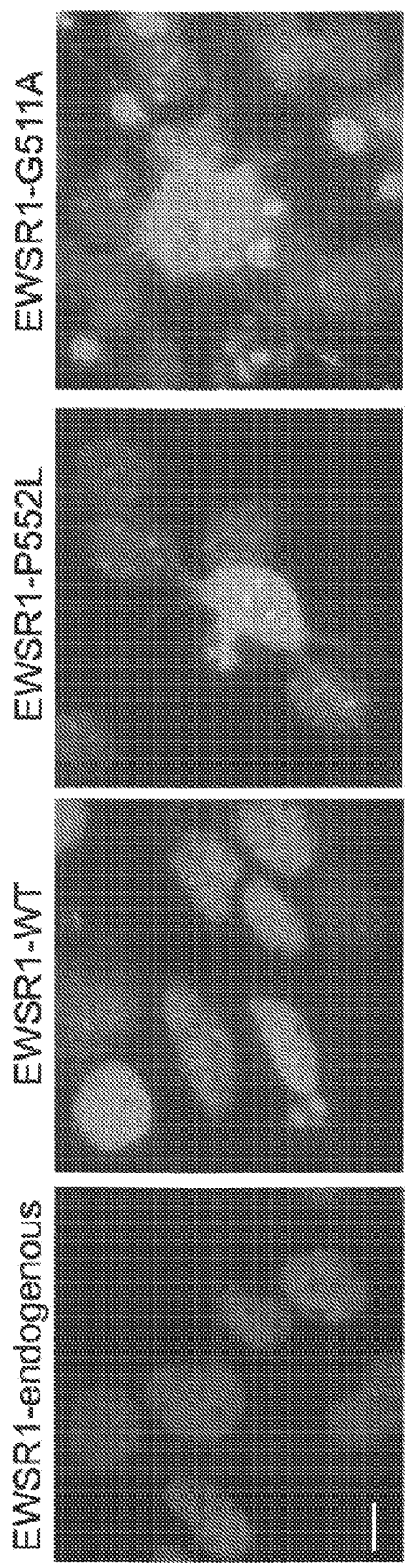
FIG. 5. ALS-linked EWSR1 and TAF15 mutations promote cytoplasmic localization in motor neurons. Embryonic stem cell derived neurons were transduced with doxycycline (Dox) inducible lentiviruses expressing wild-type (WT) or ALS-linked mutants of EWSR1 (a-c) or TAF15 (d-f), each carrying FLAG and myc epitope tags in their amino- and carboxy-termini, respectively. Five days after induction of expression by Dox, the localization of the proteins was visualized by immunofluorescence microscopy with anti-FLAG antibody (red); nuclei were visualized by DAPI staining (blue). The localization of endogenous EWSR1 and TAF15 was performed with anti-EWSR1 and anti-TAF15 specific antibodies (red) in non-transduced neurons. Induced expression of WT EWSR1 (a) or TAF15 (d) led to a slight increase in the accumulation of proteins in the cytoplasm and neuronal processes of transduced cells. The ALS-linked patient mutations (a,d) resulted in an increase in the mislocalization of EWSR1 and TAF15 to the cytoplasm and processes. Percentage of cells showing staining in the cytoplasm and processes are indicated in c (EWSR1 endogenous and transduced WT and mutants) and f (TAF15 endogenous and transduced WT and mutants). For EWSR1: *, P<0.005; **, P<0.01 (localization of EWSR1 variants compared to WT, Student's t test). For TAF15: *, P<0.004 (localization of TAF15 variants compared to WT, Student's t test). At least 100 cells were counted for each sample, with the observer blinded to the identity of the sample and each experiment was performed three independent times. Expression levels of transduced proteins were determined by immunoblots with anti-FLAG antibodies of cell lysates from EWSR1 WT and mutants (b) and TAF15 WT and mutants (e) five days after Dox induction. Vector indicates transduction of cells with empty lentivirus. Immunoblots for GAPDH were used as loading controls. The expression levels of transduced proteins were comparable between WT and mutants. (g,h) Mutant EWSR1 is mislocalized to the neurites of primary neurons cultured from mouse spinal cord. Primary mouse neuron cultures were transfected with WT or mutant EWSR1, stained with α-EWSR1 (red) and α-doublecortin (green). g) Endogenous EWSR1 is almost exclusively localized within the nucleus of neurons. Overexpression of WT EWSR1 shows primarily localization within the nucleus or cytoplasm of neurons, with rare neurites containing EWSR1. In contrast, the ALS-linked mutant forms of EWSR1 showed increased mislocalization into the neurites, including dendrites and axons. h) Quantitation of mislocalization of endogenous transfected WT or mutant EWSR1 into neuronal processes. A variant that was also identified in both an ALS case and a healthy control, G584S, does not affect localization in this assay. #, $P<0.002$ (localization of EWSR1 variants compared to WT, Student's t test). Error bars=mean±S.E.M. Scale bar, 5 µm for a and d; 10 µm for g.
Figure 5:
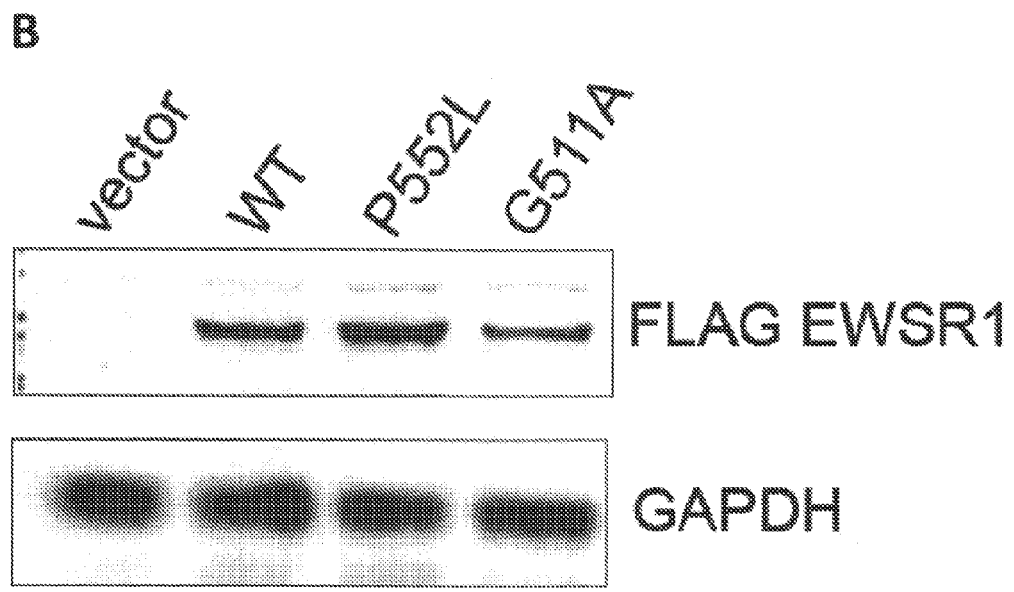
Figure 5:
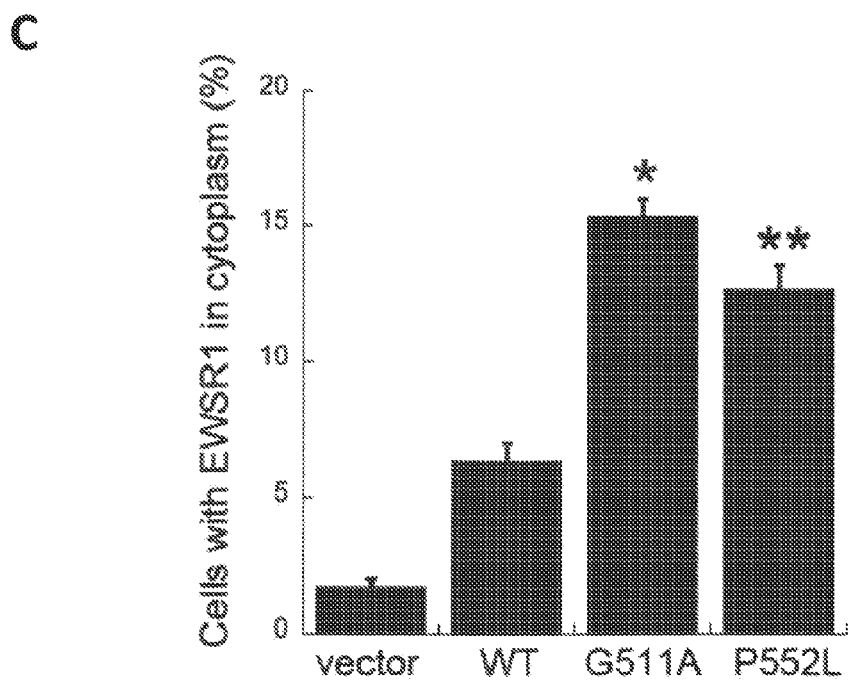
Figure 5D:
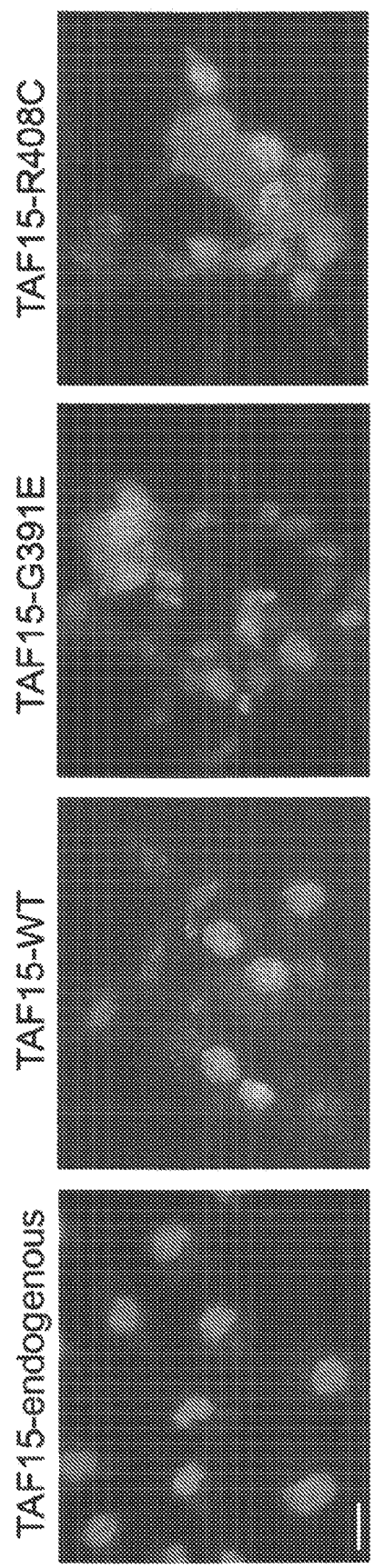
Figure 5:
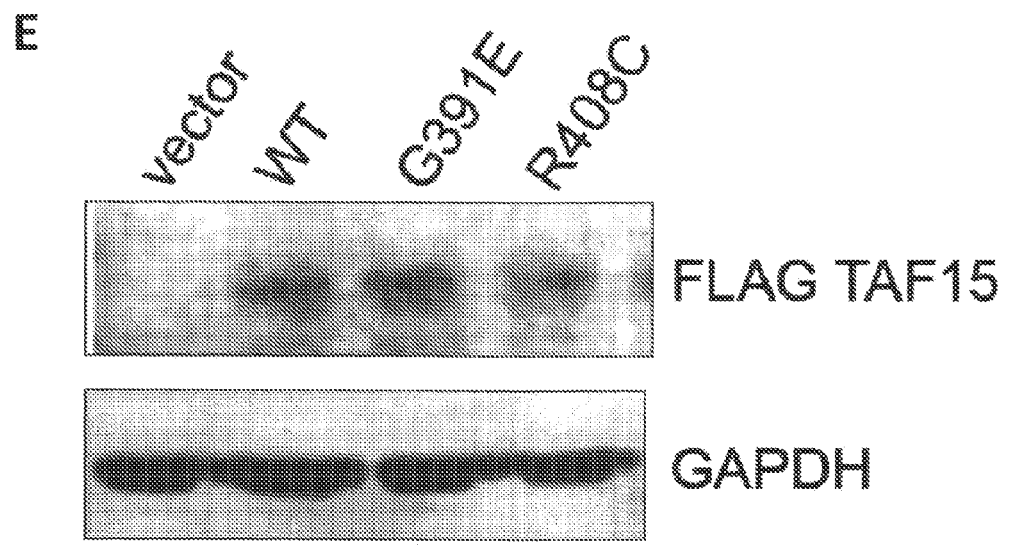
Figure 5:
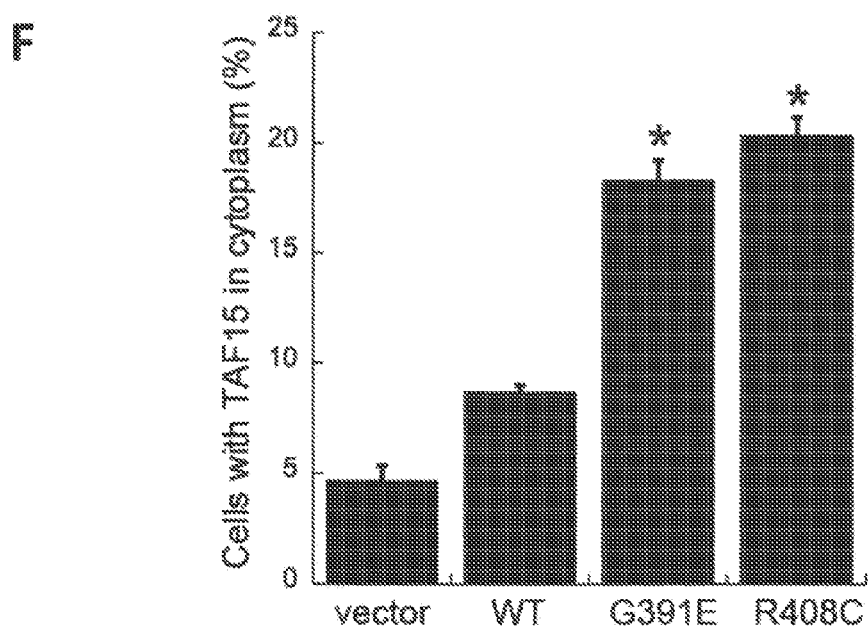
Figure 5G:
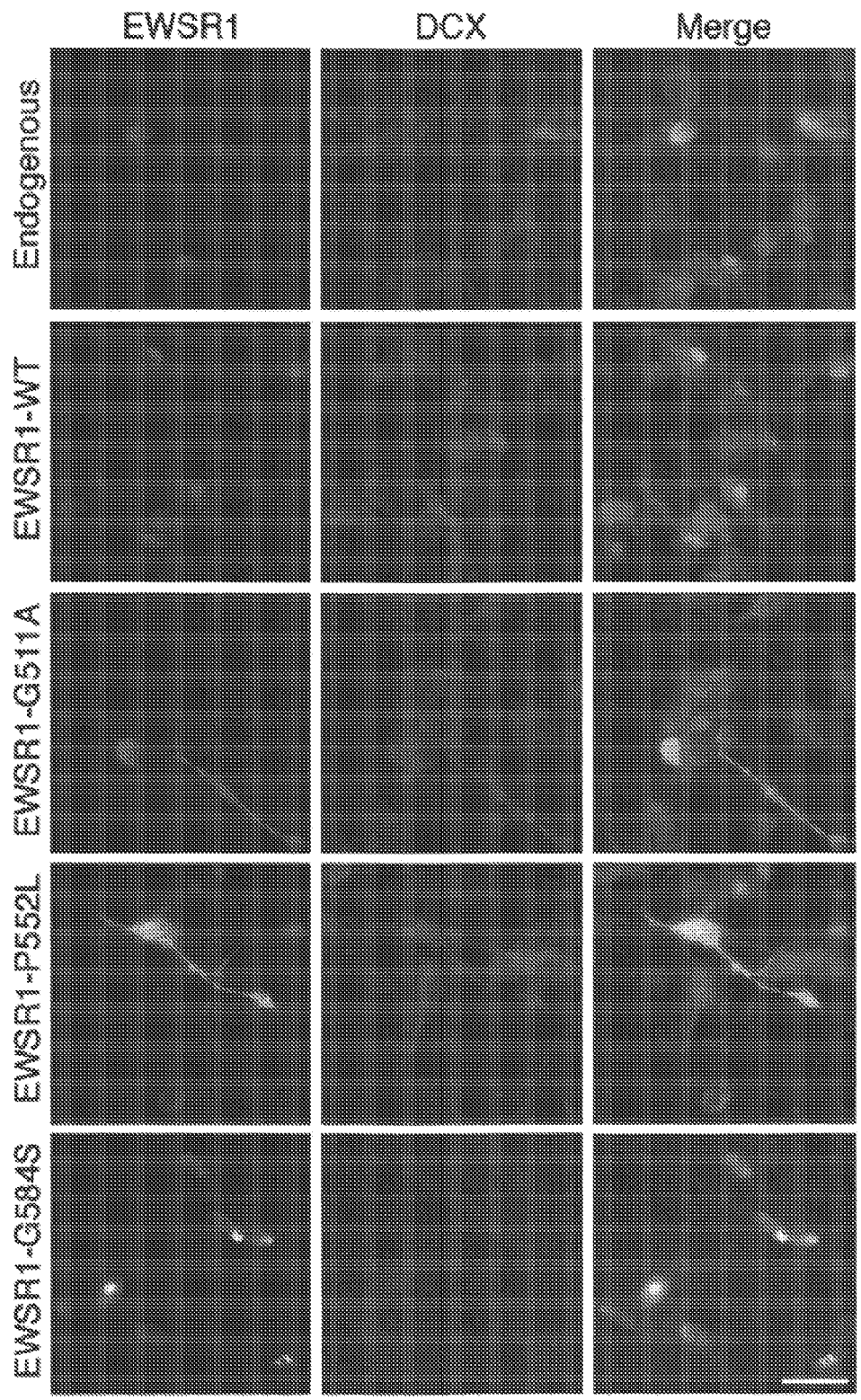
Figure 5H:
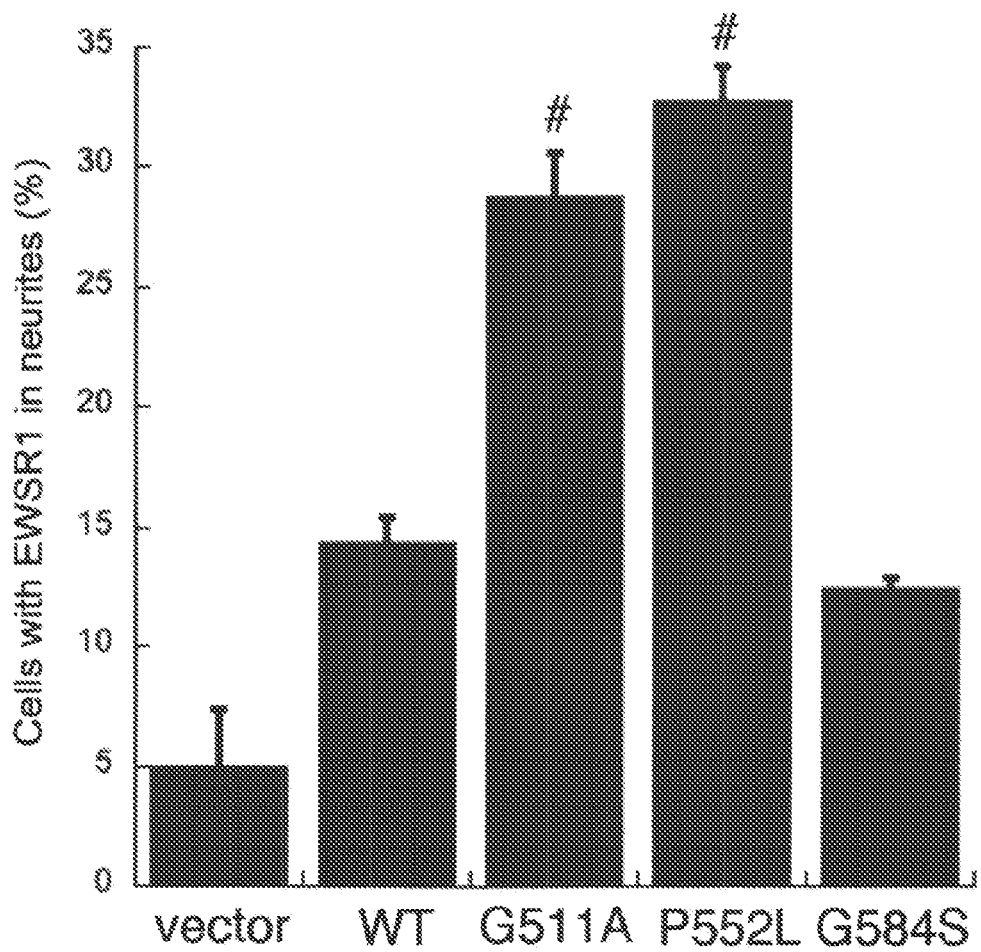

We had previously found that some ALS-linked TDP-43 mutations increase aggregation and toxicity in vitro and in yeast cells (Johnson et al., 2009) and enhance neurodegeneration in Drosophila (Elden et al., 2010). On the other hand, in recent experiments with FUS, we find that ALS-linked FUS mutants do not aggregate more rapidly than WT in vitro and in yeast, and are not more toxic than WT in yeast (Sun et al., 2010). Moreover, ALS-linked mutations located in the C-terminal PY-motif of FUS have been shown to disrupt nuclear localization rather than affecting aggregation propensity in mammalian cells (Dormann et al., 2010). As with FUS, we found that the ALS-linked variants in EWSR1 and TAF15 did not increase aggregation or toxicity in yeast and also did not enhance neurodegeneration compared to WT when upregulated in Drosophila (data not shown). However, ALS-linked mutations in TDP-43 and FUS have been shown to disrupt protein localization, leading to enhanced cytoplasmic accumulation of ALS-linked variants (Barmada et al., 2010; Dormann et al., 2010; Kabashi et al., 2010; Kwiatkowski et al., 2009; Vance et al., 2009). Given this common feature, we assessed the effects of the EWSR1 and TAF15 variants on subcellular localization. We used cell cultures of embryonic stem (ES) cell-derived neurons and primary motor neurons isolated from mouse embryos. Transduction of WT EWSR1 and TAF15 in the ES-derived neuronal cultures resulted in a mostly nuclear pattern, with occasional localization to the cytoplasm (FIG. 5a). Strikingly, all four patient specific EWSR1 and TAF15 variants analyzed resulted in a significant increase in cytoplasmic accumulation, as well as a pattern of coarse neuritic staining that was less prevalent with the WT proteins (FIG. 5 a,b,d,e). Immunoblotting confirmed that the transduced WT and variant proteins were expressed at similar levels (FIG. 5 c,f).

We observed similar effects on the localization of EWSR1 when WT or the mutant forms were transfected into primary motor neurons cultured from mouse embryos. WT EWSR1 primarily localized to the nucleus, whereas the ALS-specific variants resulted in increased cytoplasmic and neuritic accumulation (FIG. 5 g,h). We also tested EWSR1 variant G584S, which was found in both ALS patients and controls (1/817 ALS patients and 1/5,690 controls). Importantly, in contrast to the patient-specific variants, EWSR1G584S did not enhance cytoplasmic or neuritic accumulation in this assay, providing additional evidence that this variant is not likely to be pathogenic (FIG. 5 g,h). As additional variants in EWSR1 and TAF15 are identified, this functional assay will be useful for assessing their potential pathogenicity. Thus, like ALS-linked TDP-43 and FUS mutations, the ALS-linked variants of EWSR1 and TAF15 can also promote cytoplasmic accumulation of the protein in motor neurons, a disease relevant cell type, providing further evidence in support of the pathogenicity of these variants. Interestingly, in addition to the PY-motif, which can function as a NLS (Zakaryan and Gehring, 2006), sequences in the last RGG domain of EWSR1 have also been shown to be required for proper nuclear localization (Shaw et al., 2009). Notably, one of the two EWSR1 variants found is located in this domain, as are all three TAF15 variants (FIG. 2a), suggesting that perhaps these mutations perturb the function of this RGG domain in a way that decreases its ability to interact efficiently with the nuclear localization machinery, resulting in the enhanced cytoplasmic localization observed in the cell cultures (FIG. 5). While the other EWSR1 variant, G511A, is located in a RGG domain that has been suggested not to be required for nuclear localization (Shaw et al., 2009), in other contexts this domain has been shown to also contribute to nuclear localization (Araya et al., 2003).

Discussion

In an effort to streamline the identification of new ALS disease genes, we devised a simple yeast functional screen to define additional RRM proteins with properties shared by the known ALS disease genes FUS and TDP-43. This screen resulted in the enrichment of 35 proteins that behave like FUS and TDP-43 in yeast (cytoplasmic inclusions and toxicity), ten of which contain a predicted prion domain (see Table 1). Indeed, the combination of yeast screen and prion prediction algorithm enabled us to significantly focus our list of candidate genes ~13-fold. As evidence of the usefulness of this approach to define genes with a role in ALS, we identified two patient-specific missense variants in one of these genes, EWSR1, in unrelated ALS patients and three patient-specific missense variants in a homologous gene, TAF15, in three additional ALS patients. Further, we provide in vitro and in vivo evidence that these proteins have functional properties similar to those of TDP-43 and FUS: they can confer neurodegeneration in *Drosophila*, and the ALS-linked mutations can alter protein subcellular localization in motor neurons. While familial segregation could not be assessed, the absence of the variants in a very large number of healthy controls, as well as the shared structural evidence with known ALS genes, and functional in vitro data strongly support the notion that these variants in EWSR1 and TAF15 represent pathogenic disease mutations for ALS. Thus, we suggest that EWSR1 and TAF15 now join FUS and TDP-43 as RNA-binding proteins linked to ALS, further underscoring a central role for perturbations in RNA metabolism as fundamental to ALS pathogenesis. In a broader sense, these findings suggest that there may be a delicate balance in RNA processing within motor neurons such that slight perturbations from any one of several different aggregation-prone RNA-binding proteins could lead to neurodegeneration. Indeed, select ALS-linked mutations in TDP-43 increase aggregation of the protein (Johnson et al., 2009); ALS-linked mutations in FUS, EWSR1, and TAF15 might do so as well, although it is possible that these mutations could contribute to disease by distinct mechanisms (Dormann et al., 2010; Ling et al., 2010).

These findings predict that additional aggregation-prone RRM or other RNA binding proteins, like EWSR1, TAF15, FUS, and TDP-43, contribute to ALS. Notably, the prion domain algorithm ranked FUS, TAF15, and EWSR1 1st, $2^{nd}$, and $3^{rd}$ out of 213 RRM proteins, respectively, and ranked TDP-43 $10^{th}$. We suggest that genes ranked $4^{th}$ through $9^{th}$ should now be given top priority for genetic analysis in ALS patient populations. Next generation sequencing and exon capture approaches will eventually become routine in personalized medicine, (Biesecker, 2010; Ng et al., 2009a; Ng et al., 2009b) and promises to identify all genetic contributors to ALS; this approach, coupled with functional biochemical and functional studies shown, will empower elucidation of all of the genetic contributors to ALS. Meanwhile, the list of ALS candidate genes that we provide here (Table 1 and Table 2), generated by the combination of the yeast functional screen and prion domain prediction, will be a powerful resource, which promises to facilitate efforts to identify new ALS disease genes and spur innovative new diagnostic and therapeutic approaches.

EXAMPLE II

Diagnostic Assays for Detecting Increased Risk of Developing ALS

The information herein above can be applied clinically to patients for diagnosing an increased susceptibility for developing ALS, and for therapeutic intervention. Diagnostic compositions, including microarrays, and methods can be designed to identify the mutation containing EWSR1 and TAF15 genes described herein in nucleic acids from a patient to assess susceptibility for developing ALS. This can occur after a patient arrives in the clinic; the patient has blood drawn, and using the diagnostic methods described herein, a clinician can detect the aberrant nucleic acids associated with ALS if present. The nucleic acid obtained from the patient sample, which can optionally be amplified prior to assessment, will be used to diagnose a patient with an increased or decreased susceptibility for developing ALS. Kits for performing the diagnostic method of the invention are also provided herein. Such kits comprise a microarray comprising at least one probe or primer provided herein in and the necessary reagents for assessing the patient samples as described above. As discussed at length in Example I, the presence of particular mutations in the EWSR1 and TAF15 genes respectively is significantly associated with ALS, in certain instances early onset ALS. The identification of these mutations in a patient sample serves to identify those that possess an altered risk for developing ALS. The information provided herein allows for therapeutic intervention at earlier times in disease progression that previously possible.

EXAMPLE III

Screening Assays for the Identification of Agents which Modulate Pathological TDP-43-EWSR1 and/or TAF15 Complex Formation Certain aspects of the present disclosure provide methods of screening for a candidate drug (agent or compound) or a genetic factor that modulates TDP-43-EWSR1-TAF-15-RNA interactions and associated pathology. Various types of candidate drugs may be screened by the methods described herein and the effects on the function or activity or localization of the molecules assessed alone or in combination. Compounds to be screened include nucleic acids, polypeptides, small molecule compounds, and peptidomimetics. In some cases, genetic agents can be screened by contacting the yeast cell with a nucleic acid construct coding for a gene. For example, one may screen cDNA libraries expressing a variety of genes, to identify other genes that modulate these interactions. For example, the identified drugs may modulate TDP-43-EWSR1-TAF15-RNA complex formation, subcellular localization and/or neuronal cell morphology or viability. Accordingly, irrespective of the exact mechanism of action, drugs identified by the screening methods described herein are expected to provide therapeutic benefit to patients suffering from ALS.

Screening methods described herein use may employ the yeast cells or the *drosophila* cells described in Example I. Candidate drugs can be screened from large libraries of synthetic or natural compounds. One example is an FDA approved library of compounds that can be used by humans.

In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Combinatorial libraries are available and can be prepared. Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

For example, the yeast or *drosophila* cells in Example 1 can be incubated in the presence and absence of a test compound the effect of the compound on TDP-43/EWSR1/TAF15/RNA complex formation and associated cellular toxicity assessed. Agents so identified could then be tested in whole animal models of ALS to assess in vivo efficacy.

Agents identified using the screening assays described herein are also encompassed by the present invention References Aguzzi, A., and Rajendran, L. (2009). The transcellular spread of cytosolic amyloids, prions, and prionoids. Neuron 64, 783-790.

Alberti, S., Gitler, A. D., and Lindquist, S. (2007). A suite of Gateway((R)) cloning vectors for high-throughput genetic analysis in *Saccharomyces cerevisiae*. Yeast (Chichester, England) 24, 913-919.

Alberti, S., Halfmann, R., King, O., Kapila, A., and Lindquist, S. (2009). A systematic survey identifies prions and illuminates sequence features of prionogenic proteins. Cell 137, 146-158.

Araya, N., Hirota, K., Shimamoto, Y., Miyagishi, M., Yoshida, E., Ishida, J., Kaneko, S., Kaneko, M., Nakajima, T., and Fukamizu, A. (2003). Cooperative interaction of EWS with CREB-binding protein selectively activates hepatocyte nuclear factor 4-mediated transcription. J Biol Chem 278, 5427-5432.

Barmada, S. J., Skibinski, G., Korb, E., Rao, E. J., Wu, J. Y., and Finkbeiner, S. (2010). Cytoplasmic mislocalization of TDP-43 is toxic to neurons and enhanced by a mutation associated with familial amyotrophic lateral sclerosis. J Neurosci 30, 639-649.

Biesecker, L. G. (2010). Exome sequencing makes medical genomics a reality. Nat Genet. 42, 13-14.

Cleveland, D. W., and Rothstein, J. D. (2001). From Charcot to Lou Gehrig: deciphering selective motor neuron death in ALS. Nat Rev Neurosci 2, 806-819.

Cushman, M., Johnson, B. S., King, O. D., Gitler, A. D., and Shorter, J. (2010). Prion-like disorders: blurring the divide between transmissibility and infectivity. J Cell Sci 123, 1191-1201.

Dormann, D., Rodde, R., Edbauer, D., Bentmann, E., Fischer, I., Hruscha, A., Than, M. E., Mackenzie, I. R., Capell, A., Schmid, B., et al. (2010). ALS-associated fused in sarcoma (FUS) mutations disrupt Transportin-mediated nuclear import. EMBO J.

Elden, A. C., Kim, H. J., Hart, M. P., Chen-Plotkin, A. S., Johnson, B. S., Fang, X., Armakola, M., Geser, F., Greene, R., Lu, M. M., et al. (2010). Ataxin-2 intermediate-length polyglutamine expansions are associated with increased risk for ALS. Nature 466, 1069-1075.

Guthrie, C., and Fink, G. R. (2002). Methods in Ezymology: Guide to Yeast Genetics and Molecular and Cell Biology. Academic Press 169.

Hanson, K. A., Kim, S. H., Wassarman, D. A., and Tibbetts, R. S. (2010). Ubiquilin modifies TDP-43 toxicity in a *Drosophila* model of amyotrophic lateral sclerosis (ALS). J Biol Chem 285, 11068-11072.

Ito, H., Fukuda, Y., Murata, K., and Kimura, A. (1983). Transformation of intact yeast cells treated with alkali cations. J Bacteriol 153, 163-168.

Johnson, B. S., McCaffery, J. M., Lindquist, S., and Gitler, A. D. (2008). A yeast TDP-43 proteinopathy model: Exploring the molecular determinants of TDP-43 aggregation and cellular toxicity. Proc Natl Acad Sci USA 105, 6439-6444.

Johnson, B. S., Snead, D., Lee, J. J., McCaffery, J. M., Shorter, J., and Gitler, A. D. (2009). TDP-43 is intrinsically aggregation-prone, and amyotrophic lateral sclerosis-linked mutations accelerate aggregation and increase toxicity. J Biol Chem 284, 20329-20339.

Kabashi, E., Lin, L., Tradewell, M. L., Dion, P. A., Bercier, V., Bourgouin, P., Rochefort, D., Bel Hadj, S., Durham, H. D., Vande Velde, C., et al. (2010). Gain and loss of function of ALS-related mutations of TARDBP (TDP-43) cause motor deficits in vivo. Hum Mol Genet. 19, 671-683.

Kwiatkowski, T. J., Jr., Bosco, D. A., Leclerc, A. L., Tamrazian, E., Vanderburg, C. R., Russ, C., Davis, A., Gilchrist, J., Kasarskis, E. J., Munsat, T., et al. (2009). Mutations in the FUS/TLS gene on chromosome 16 cause familial amyotrophic lateral sclerosis. Science 323, 1205-1208.

Lagier-Tourenne, C., and Cleveland, D. W. (2009). Rethinking ALS: the FUS about TDP-43. Cell 136, 1001-1004.

Lagier-Tourenne, C., Polymenidou, M., and Cleveland, D. W. (2010). TDP-43 and FUS/TLS: emerging roles in RNA processing and neurodegeneration. Hum Mol. Genet.

Li, Y., Ray, P., Rao, E. J., Shi, C., Guo, W., Chen, X., Woodruff, E. A., 3rd, Fushimi, K., and Wu, J. Y. (2010a). A *Drosophila* model for TDP-43 proteinopathy. Proc Natl Acad Sci USA 107, 3169-3174.

Li, Y., Sun, L., Cai, T., Zhang, Y., Lv, S., Wang, Y., and Ye, L. (2010b). alpha-Synuclein overexpression during manganese-induced apoptosis in SH-SY5Y neuroblastoma cells. Brain Res Bull 81, 428-433.

Ling, S. C., Albuquerque, C. P., Han, J. S., Lagier-Tourenne, C., Tokunaga, S., Zhou, H., and Cleveland, D. W. (2010). ALS-associated mutations in TDP-43 increase its stability and promote TDP-43 complexes with FUS/TLS. Proc Natl Acad Sci USA.

Lu, Y., Ferris, J., and Gao, F. B. (2009). Frontotemporal dementia and amyotrophic lateral sclerosis-associated disease protein TDP-43 promotes dendritic branching. Mol Brain 2, 30.

Neumann, M., Sampathu, D. M., Kwong, L. K., Truax, A. C., Micsenyi, M. C., Chou, T. T., Bruce, J., Schuck, T., Grossman, M., Clark, C. M., et al. (2006). Ubiquitinated TDP-43 in frontotemporal lobar degeneration and amyotrophic lateral sclerosis. Science 314, 130-133.

Ng, S. B., Buckingham, K. J., Lee, C., Bigham, A. W., Tabor, H. K., Dent, K. M., Huff, C. D., Shannon, P. T., Jabs, E. W., Nickerson, D. A., et al. (2009a). Exome sequencing identifies the cause of a mendelian disorder. Nat Genet. 42, 30-35.

Ng, S. B., Turner, E. H., Robertson, P. D., Flygare, S. D., Bigham, A. W., Lee, C., Shaffer, T., Wong, M., Bhattacharjee, A., Eichler, E. E., et al. (2009b). Targeted capture and massively parallel sequencing of 12 human exomes. Nature 461, 272-276.

Ritson, G. P., Custer, S. K., Freibaum, B. D., Guinto, J. B., Geffel, D., Moore, J., Tang, W., Winton, M. J., Neumann, M., Trojanowski, J. Q., et al. (2010). TDP-43 mediates degeneration in a novel *Drosophila* model of disease caused by mutations in VCP/p 97. J Neurosci 30, 7729-7739.

Shaw, D. J., Morse, R., Todd, A. G., Eggleton, P., Lorson, C. L., and Young, P. J. (2009). Identification of a tripartite import signal in the Ewing Sarcoma protein (EWS). Biochem Biophys Res Commun 390, 1197-1201.

Sun, Z., Diaz, Z., Chesi, A., Ramos, D., Shorter, J., and Gitler, A. D. (2010). Defining pathogenic features of the ALS disease protein FUS/TLS. Manuscript submitted.

Tan, A. Y., and Manley, J. L. (2009). The TET family of proteins: functions and roles in disease. J Mol Cell Biol 1, 82-92.

Van Damme, P., and Robberecht, W. (2009). Recent advances in motor neuron disease. Curr Opin Neurol 22, 486-492.

Vance, C., Rogelj, B., Hortobagyi, T., De Vos, K. J., Nishimura, A. L., Sreedharan, J., Hu, X., Smith, B., Ruddy, D., Wright, P., et al. (2009). Mutations in FUS, an RNA processing protein, cause familial amyotrophic lateral sclerosis type 6. Science 323, 1208-1211.

Wichterle, H., Peljto, M., and Nedelec, S. (2009). Xenotransplantation of embryonic stem cell-derived motor neurons into the developing chick spinal cord. Methods Mol Biol 482, 171-183.

Zakaryan, R. P., and Gehring, H. (2006). Identification and characterization of the nuclear localization/retention signal in the EWS proto-oncoprotein. J Mol Biol 363, 27-38.

While the invention has been described in detail and with reference to specific examples thereof, it will be apparent to one skilled in the art that various changes and modifications can be made therein without departing from the spirit and scope thereof.

---

What is claimed is:

1. A diagnostic kit for predicting an increased risk of an individual for developing amyotrophic lateral sclerosis (ALS) disease, consisting of an isolated detectably labeled nucleic acid that specifically hybridizes to a mutated TAF15 encoding nucleic acid, wherein the mutated TAF15 encoding nucleic acid comprises a mutation selected from the group consisting of:
   i. a missense G>A mutation in exon 14 causing a Gly391Glu alteration; and
   ii. a missense C>T mutation in exon 15 causing a Arg408Cys alteration relative to wild-type TAF15 encoding nucleic acids;
wherein said label is selected from the group consisting of an antibody, a product that produces a reporter signal, and a marker, each being suitable for detecting said mutated TAF 15 encoding nucleic acid.

2. An isolated nucleic acid encoding an altered TAF15 protein comprising a genetic alteration selected from the group consisting of a
   i) a missense G>A mutation in exon 14 causing a Gly391Glu alteration; and
   ii) a missense C>T mutation in exon 15 causing a Arg408Cys alteration, wherein said nucleic acid is a cDNA.

3. The nucleic acid of claim 2 affixed to a solid support.
4. A vector comprising the nucleic acid of claim 2.
5. A host cell comprising the vector of claim 4.
6. The host cell of claim 5 which is a drosophila cell or a yeast cell.

* * * * *